US010208286B2

(12) United States Patent
Bernstein

(10) Patent No.: US 10,208,286 B2
(45) Date of Patent: Feb. 19, 2019

(54) EXPANSION AND ENGRAFTMENT OF STEM CELLS USING NOTCH 1 AND/OR NOTCH 2 AGONISTS

(71) Applicant: FRED HUTCHINSON CANCER RESEARCH CENTER, Seattle, WA (US)

(72) Inventor: Irwin D. Bernstein, Seattle, WA (US)

(73) Assignee: Fred Hutchinson Cancer Research Center, Seattle, WA (US)

(*) Notice: Subject to any disclaimer, the term of this patent is extended or adjusted under 35 U.S.C. 154(b) by 0 days.

(21) Appl. No.: 15/315,660

(22) PCT Filed: Jun. 3, 2015

(86) PCT No.: PCT/US2015/033959
§ 371 (c)(1),
(2) Date: Dec. 1, 2016

(87) PCT Pub. No.: WO2015/187815
PCT Pub. Date: Dec. 10, 2015

(65) Prior Publication Data
US 2017/0107493 A1 Apr. 20, 2017

Related U.S. Application Data

(60) Provisional application No. 62/007,848, filed on Jun. 4, 2014.

(51) Int. Cl.
*C12N 5/0789* (2010.01)

(52) U.S. Cl.
CPC ........ *C12N 5/0647* (2013.01); *C12N 2501/42* (2013.01)

(58) Field of Classification Search
None
See application file for complete search history.

(56) References Cited

U.S. PATENT DOCUMENTS

| 5,648,464 | A | 7/1997 | Artavanis-Tsakonas et al. |
| 5,780,300 | A | 7/1998 | Artavanis-Tsakonas et al. |
| 5,849,869 | A | 12/1998 | Artavanis-Tsakonas et al. |
| 5,856,441 | A | 1/1999 | Artavanis-Tsakonas et al. |
| 6,149,902 | A | 11/2000 | Artavanis-Tsakonas et al. |

FOREIGN PATENT DOCUMENTS

| WO | WO2011127472 A1 | 10/2011 |
| WO | WO2013086436 A1 | 6/2013 |

OTHER PUBLICATIONS

Kojika, Saturo; Griffin, James D; "Notch receptors and hematopoiesis" Experimental Hematology, 29, 1041-1052, 2001 (Year: 2001).*
Bigas, et al., "Notch1 and Notch2 Inhibit Myeloid Differentiation in Response to Different Cytokines," J. Mol. Cell. Biol., vol. 18, No. 4, 1998, pp. 2324-2333.
Carlesso, et al., "Notch1-induced delay of human hematopoietic progenitor cell differentiation is associated with altered cell cycle kinetics," Blood, vol. 93, No. 3, 1999, pp. 838-848.
Dallas, et al., "Density of the Notch ligand Delta1 determines generation of B and T cell precursors from hematopoietic stem cells," J. Exp. Med., vol. 201, 2005, pp. 1361-1366.
Dao, et al., "Adhesion to fibronectin maintains regenerative capacity during ex vivo culture and transduction of human hematopoietic stem and progenitor cells," Blood, vol. 92, No. 12, 1998, pp. 4612-4621.
Deftos, et al., "Correlating notch signaling with thymocyte maturation," Immunity, vol. 9, No. 6, 1998, pp. 777-786.
Delaney, et al., "Dose-dependent effects of the Notch ligand Delta1 on ex vivo differentiation and in vivo marrow repopulating ability of cord blood cells," Blood, vol. 106, No. 8, 2005, pp. 2693-2699.
Delaney, et al., "Notch-mediated expansion of human cord blood progenitor cells capable of rapid myeloid reconstitution," Nature Med., vol. 16, No. 2, 2010, pp. 232-236.
Glen, et al., "Production of erythrocytes from directly isolated or Delta1 Notch ligand expanded CD34+ hematopoietic progenitor cells: process characterization, monitoring and implications for manufacture", Cytotherapy, vol. 15, No. 9, 2013, pp. 1106-1117.
Jehn, et al., "Cutting edge: protective effects of notch-1 on TCR-induced apoptosis," J. Immunol., vol. 162, No. 2, 1999, pp. 635-638.
Jones, et al., "Stromal expression of Jagged 1 promotes colony formation by fetal hematopoietic progenitor cells," Blood, vol. 92, No. 5, 1998, pp. 1505-1511.
Luca, et al., "Structural biology. Structural basis for Notch1 engagement of Delta-like 4," Science, vol. 347, No. 6224, 2015, pp. 847-853.
Milner et al., "Inhibition of granulocytic differentiation by mNotch1," Proc. Natl. Acad. Sci. U.S.A., vol. 93, 1996, pp. 13014-13019.
Ohishi, et al. "Monocytes express high amounts of Notch and undergo cytokine specific apoptosis following interaction with the Notch ligand, Delta-1," Blood, vol. 95, No. 9, 2000, pp. 2847-2854.
Pui, et al., "Notch1 expression in early lymphopoiesis influences B versus T lineage determination," Immunity, vol. 11, No. 3, 1999, pp. 299-308.

(Continued)

Primary Examiner — David W Berke-Schlessel
(74) Attorney, Agent, or Firm — Lee & Hayes PC; C. Rachal Winger; Thu Nguyen

(57) ABSTRACT

The present disclosure provides methods for immortalizing precursor cells that are non-terminally differentiated cells such as stem cells, the methods comprising culturing the precursor cells in the presence of a Notch 1 agonist, Notch 2 agonist or Notch 1 agonist and Notch 2 agonist (and, in particular embodiments, one or more growth factors) that support the proliferation but not differentiation of the non-terminally differentiated cells. The present disclosure further provides methods to induce the differentiation of immortalized cells, comprising growing the cells in the presence of a Notch 1 agonist, Notch 2 agonist or Notch 1 agonist and Notch 2 agonist and at least one growth factor which supports the differentiation of the cell into a more specialized cell type. The immortalized and/or differentiated cells of the disclosure can be used to repopulate cell populations that have been diminished, for example as a result of infection or exposure to certain drugs. The disclosure further provides a cell culture comprising a population of non-terminally differentiated cells immortalized by the methods of the present disclosure and kits comprising reagents that promote the immortalization of precursor cells.

18 Claims, 42 Drawing Sheets

(56) References Cited

OTHER PUBLICATIONS

Radtke, et al., "Deficient T Cell Fate Specification in Mice with an Induced Inactivation of Notch1," Immunity, vol. 10, No. 5, 1999, pp. 547-558.
Robey, et al., "An activated form of Notch influences the choice between CD4 and CD8 T cell lineages," Cell, vol. 87, No. 3, 1996, pp. 483-492.
Sprinzak, et al., "Cis-interactions between Notch and Delta generate mutually exclusive signalling states," Nature, vol. 465, No. 7294, 2010, pp. 86-90.
Search Report and Written Opinion dated Oct. 21, 2015 in International Application No. PCT/US15/33959.
Tomita, et al., "The bHLH gene Hes1 is essential for expansion of early T cell precursors," Genes Dev., vol. 13, No. 9, 1999, pp. 1203-1210.
Varnum-Finney, et al., "The Notch ligand, Jagged-1, influences the development of primitive hematopoietic precursor cells," Blood, vol. 91, No. 11, 1998, pp. 4084-4991.
Walker, et al., "The Notch/Jagged pathway inhibits proliferation of human hematopoietic progenitors in vitro," Stem Cells, vol. 17, No. 3, 1999, pp. 162-171.
Washburn, et al., "Notch activity influences the alphabeta versus gammadelta T cell lineage decision," Cell, vol. 88, No. 6, 1997, pp. 833-843.
Office Action dated May 18, 2018 for Australian Patent Application No. 2015271689, 4 pages.
Office Action dated Mar. 19, 2018 for European Application No. 15729698.9.

\* cited by examiner

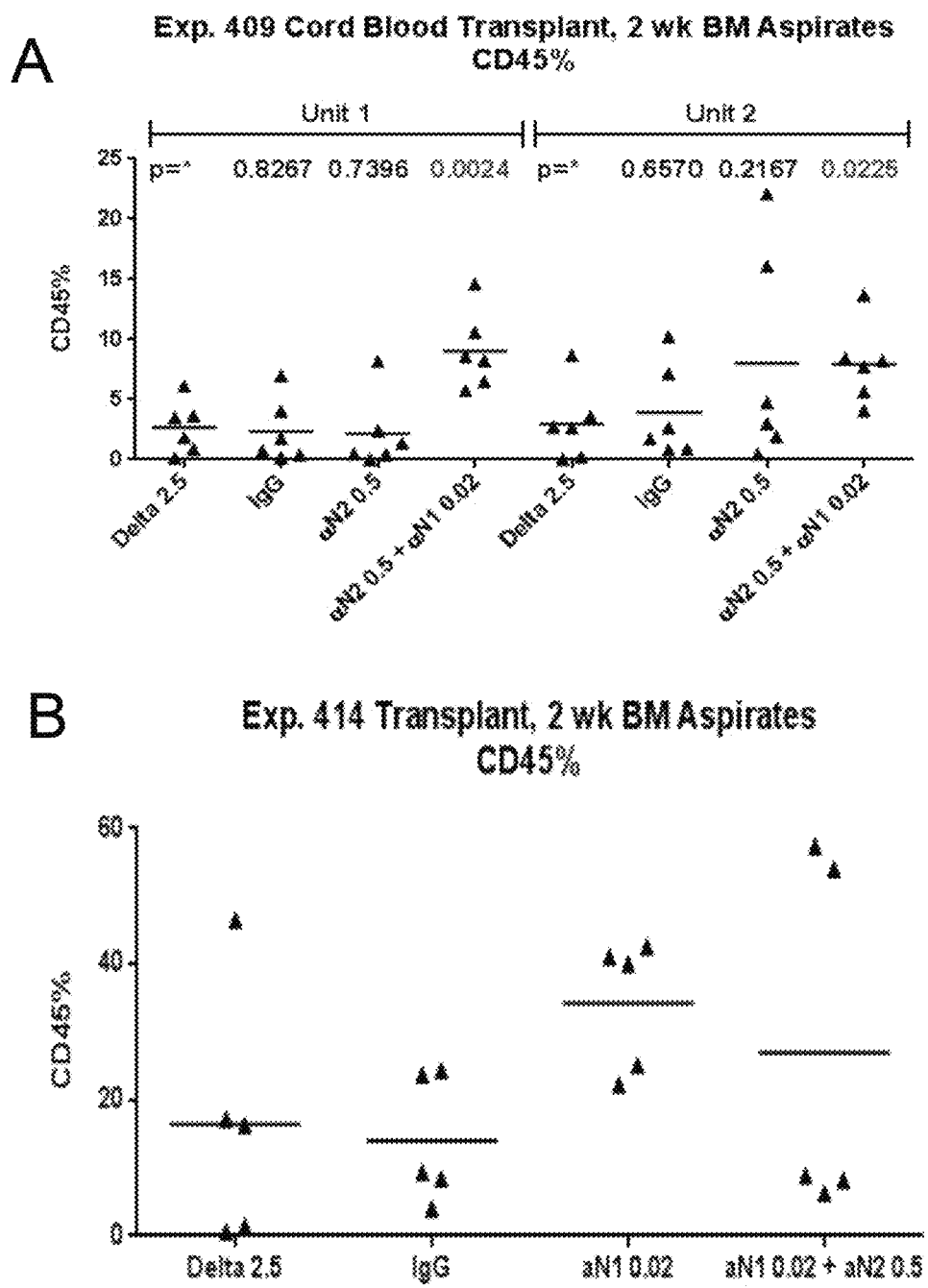
FIG. 7A-B

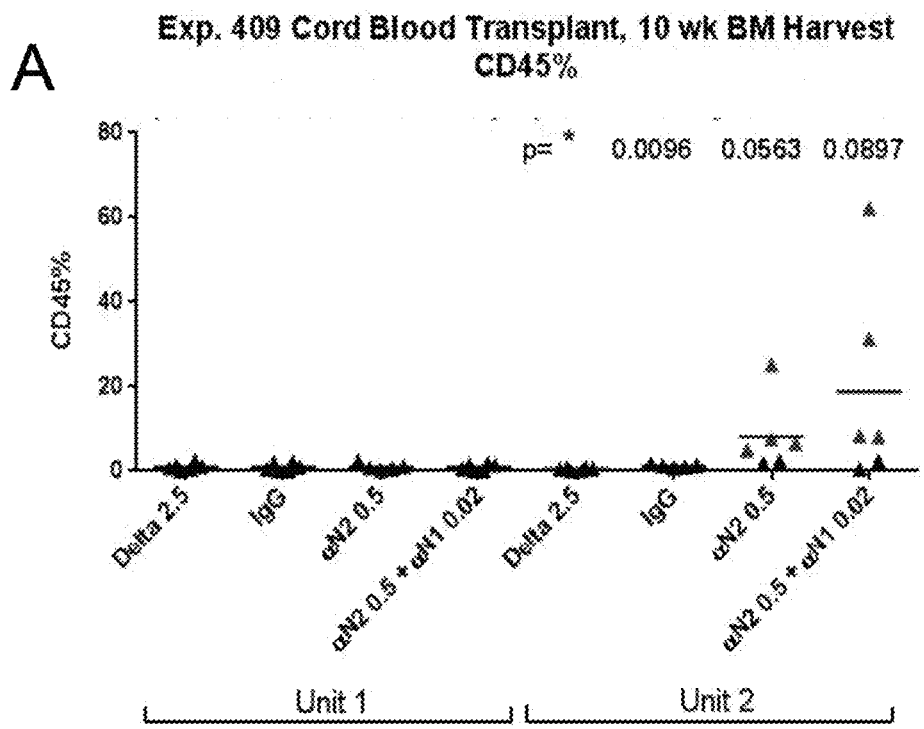
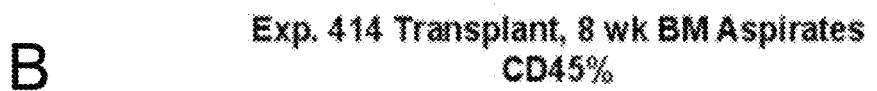
FIG. 8A-B

Figure 12:
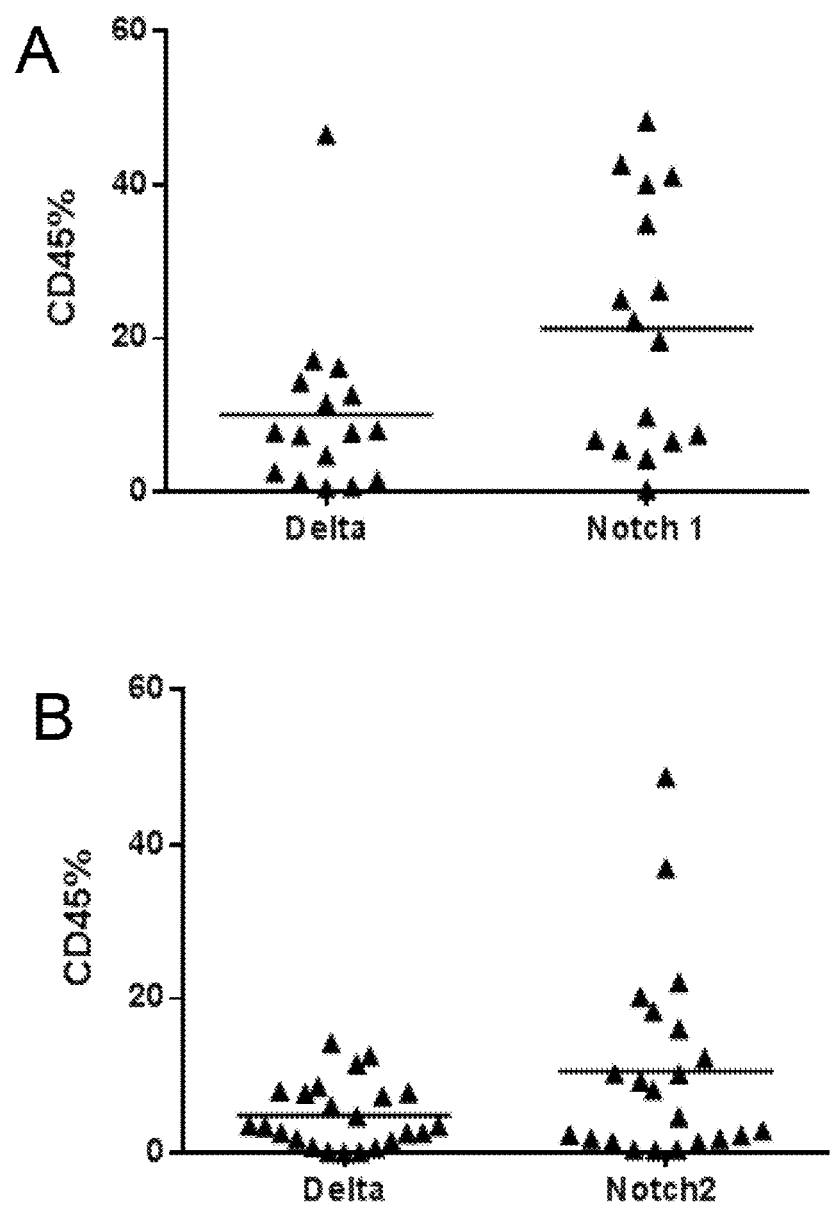

FIG. 12A-B

EXPANSION AND ENGRAFTMENT OF STEM CELLS USING NOTCH 1 AND/OR NOTCH 2 AGONISTS This application is a U.S. national phase application based on International Application No. PCT/US2015/033959, filed on Jun. 3, 2015, which claims the benefit of U.S. Provisional Application No. 62/007,848, filed on Jun. 4, 2014, each of which is incorporated herein by reference in its entirety.

STATEMENT OF GOVERNMENT SUPPORT

This invention was made with government support under HL100395 awarded by National Institutes of Health. The government has certain rights in the invention.

1. FIELD OF THE DISCLOSURE

The present disclosure provides methods for producing immortalized precursor cell populations, the methods comprising culturing non-immortalized precursor cells in the presence of a Notch 1 agonist and/or a Notch 2 agonist and one or more proliferation-promoting growth factors for a time period beyond which cells of the precursor cell type stop proliferating and differentiate or die. The disclosure further provides methods for producing immortalized and differentiated cell types comprising exposing precursor cells prior or following immortalization to conditions that promote their differentiation. The immortalized cells derived therefrom can be used for cell therapy.

2. BACKGROUND OF THE DISCLOSURE 2.1 The Notch Signaling Pathway

Members of the Notch family encode large transmembrane proteins that play central roles in cell-cell interactions and cell-fate decisions during early development in a number of invertebrate systems. The Notch receptor is part of a highly conserved pathway that enables a variety of cell types to choose between alternative differentiation pathways based on those taken by immediately neighboring cells. This receptor appears to act through a common step that controls the progression of uncommitted cells toward the differentiated state by inhibiting their competence to adopt one of two alternative fates, thereby allowing the cell either to delay differentiation, or in the presence of the appropriate developmental signal, to commit to differentiate along the non-inhibited pathway.

Genetic and molecular studies have led to the identification of a group of genes which define distinct elements of the Notch signaling pathway. While the initial identification of these various elements has came exclusively from *Drosophila* using genetic tools as the initial guide, subsequent analyses have lead to the identification of homologous proteins in vertebrate species including humans. The molecular relationships between the known Notch pathway elements as well as their subcellular localization are depicted in Artavanis-Tsakonas et al., 1995, Science 268: 225-232) and Artvanis-Tsakonas et al., 1999, Science 284: 770-776.

2.1.1. Members of the Notch Signaling Pathway

Several members of the Notch signaling pathway have been cloned and sequenced in invertebrate and vertebrate organisms. Non-mammalian Notch genes include those identified in *Drosophila* (Wharton et al., 1985, Cell 43:567-581); *Xenopus* (Coffman et al., 1990, Science 249:1438-1441); and zebrafish (Bierkamp et al., 1993, Mech. Dev. 43:87-100). At least four mammalian Notch homologs have been identified (Notch-1, -2, -3, and -4; Weinmaster et al., 1991, Development 113:199-205; Ellisen et al., 1991, Cell 66:523-534; Weinmaster et al., 1992, Development 116:931-941; Franco del Amo et al., 1993, Genomics 15:259-264; Lardelli and Lendahl, 1993, Exp. Cell. Res. 204:364-372; Milner et al., 1994, Blood. 83:2057-62; Lardelli et al., 1994, Mech Dev. 46: 123-136; Uyttendaele et al., 1996, Development 122:2251-9). Other members of the Notch pathway include the ligands Delta and Serrate/Jagged, the cytoplasmic protein Deltex, the transcriptional activator RBP-Jκ, also known as CBF1, downstream targets including but not limited to the Enhancer of Split family of bHLH transcription factors, and, Fringe (Panin et al., 1997, Nature 387: 908-912), which acts in the Golgi as a glycosyltransferase enzyme that modifies the epidermal growth factor (EGF) modules of Notch and alters the ability of Notch to bind its ligand Delta. The following non-exhaustive list of articles describes the gene and protein sequences, as well as functional roles, of key members of the Notch signaling pathway:

Invertebrate Ligands: (i) Delta (Kopczynski et al., 1988, Genes Dev. 2:1723-1735; Henrique et al., 1995, Nature 375:787-790; Chitnis et al., 1995, Nature 375:761-766); and (ii) Serrate (Fleming et al., 1990, Genes Dev. 1:2188-2201; Lindsell et al., 1995, Cell 80:909-917; Thomas et al., 1991, Development 111:749-761; Tax et al., 1994, Nature 368: 150-154).

Vertebrate Ligands: (i) Serrate (Thomas, 1991, Development 111: 749-761; Lindsell et al., 1995, Cell 80:909-917); and (ii) Delta (Chitnis et al., 1995, Nature 375:761; Henrique et al., 1995, Nature 375:787-790; Bettenhausen et al., 1995, Development 121:2407).

Other Invertebrate Notch Pathway Members: (i) the cytoplasmic protein Deltex (Busseau et al., 1994, Genetics 136:585-596); (ii) the nuclear proteins Mastermind, Hairless, the Enhancer of Split Complex (Smoller et al., 1990, Genes Dev. 4:1688-1700; Bang and Posakony, 1992, Genes Dev. 6:1752-1769; Maier et al., 1992, Mech. Dev. 38:143-156; Delidakis et al., 1991, Genetics 129:803-823; Schrons et al., 1992, Genetics 132:481-503; and Fortini and Artavanis-Tsakonas, 1994, Cell 79:273-282); (iii) Suppressor of Hairless (Furukawa et al., 1991, J. Biol. Chem. 266:23334-23340; Furukawa et al., 1992, Cell 69:1191-1197; and Schweisguth and Posakony, 1992, Cell 69:1199-1212); and (iv) Fringe (Irvine and Wieschaus, 1994, Cell 79:595-606).

Other Vertebrate Notch Pathway Members: (i) RBP-Jκ (Matsunami et al., 1989, Nature 342:934-937; Kawaichi et al., 1992, J. Biol. Chem. 267:4016-4022); (ii) Deltex (Matsunami et al., 1998, Nat. Genet. 19:74-78); (iii) Fringe, including Lunatic, Manic and Radical Fringe (Wu et al., 1996, Science 273:355-358; Moran et al., 1999, Mamm. Genome 10:535-541).

2.1.2. Notch Family Members Encode Surface Receptors that Mediate Inhibitory Signals via the Cytoplasmic Domain Extensive genetic and molecular studies in *Drosophila* and *C. elegans* have shown that the proteins encoded by Notch homologs act as cell surface receptors which can activate inhibitory signal transduction pathways (Greenwald and Rubin, 1992, Cell. 68:271-281; Heitzler and Simpson, 1991, Cell 64:1083-1092; Yochem and Greenwald, 1989, Cell 58:553-63; Fehon et al., 1991, J. Cell Biol. 113:657-669; Rebay et al., 1993, Cell 74:319-329).

Notch signaling is thought to be initiated by interaction with one of the Notch ligands (Delta-1, -2, -3, or Jagged-1 or -2) (Shawber et al., 1996, Developmental Biology 180: 370-76; Luo et al., 1997, Molecular and Cellular Biology 17:6057-6067; Henrique et al., 1997, Current Biology 7:661-70; Bettenhausen et al., 1995, Development 121: 2407-18; Dunwoodie et al., 1997, Development 124:3065-76). Each of the known ligands is characterized by an extracellular domain containing multiple EGF repeats and a highly conserved DSL domain found in *Drosophila, C. elegans*, and in vertebrates (Tax et al., 1994, Nature 368: 150-154). There is evidence that the ability of particular Notch ligands to induce Notch activation can be modified by the expression of other genes. For example, expression of Fringe prevents activation of Notch by Serrate (*Drosophila* homolog of Jagged), but enhances Delta activity (Fleming et al., 1997, Development 124:2973-81).

There is considerable evidence that cellular interactions mediated by the extracellular domain modulate signal transduction by the intracellular domain, resulting in regulation of differentiation (Yochem and Greenwald, 1989, Cell 58:553-563; Rebay et al., 1993, Cell 74:319-329). Data indicates that this occurs as a result of binding of the extracellular domain to one of its ligands, followed by a series of proteolytic cleavages which, in turn, leads to release of the intracellular domain of Notch (Struhl and Adachi, 1998, Cell. 93:649-660; Schroeter et al., 1998, Nature 393:382-386). Functional analyses involving the expression of truncated forms of the Notch receptor have indicated that receptor activation depends on the six cdc10/ankyrin repeats in the intracellular domain. Further, Notch activation requires that the cdc10/ankyrin repeats reach the nucleus—possibly after proteolytic cleavage from the remainder of the protein—and participate in transcriptional activation (Struhl and Adachi, 1998, Cell 93:649-660). Deltex and Suppressor of Hairless, whose over-expression results in an apparent activation of the pathway, associate with those repeats. Recent evidence suggests that the proteolytic cleavage step that releases the cdc10/ankyrin repeats for nuclear entry is dependent on Presenilin activity (De Strooper et al., 1999, Nature 398:518-522; Struhl and Greenwald, ibid.:522-525; Ye et al., ibid.:525-529).

The Notch pathway is dependent on protein processing events additional to the step that releases the ankyrin repeats of Notch to the nucleus. The Notch receptor present in the plasma membrane comprises a heterodimer of two Notch proteolytic cleavage products, one comprising an N-terminal fragment including a portion of the extracellular domain, the transmembrane domain and the intracellular domain, and the other including the majority of the extracellular domain (Blaumueller et al., 1997, Cell 0:281-291). The proteolytic cleavage step of Notch to activate the receptor occurs in the Golgi apparatus and is mediated by a furin-like convertase (Logeat et al., 1998, Proc. Natl. Acad. Sci. USA 95:8108-8112). The Notch ligand, Delta, additionally requires cleavage for activation. Delta is thought to be cleaved by ADAM disintegrin metalloprotease Kuzbanian at the cell surface to release a soluble and active form of Delta (Qi et al., 1999, Science 283:91-94).

The intracellular domain of Notch has been shown to act as a constitutively active receptor, because forced expression of this domain prevents myocyte fusion in C2 myoblasts (Kopan et al., 1994, Development 120:2385-2396), blocks muscle conversion of 3T3 cells by MyoD and Myf-5 (Kopan et al., 1994, Development 120:2385-2396), prevents muscle differentiation of DMSO-induced P19 embryonal carcinoma cells, and inhibits neurogenesis while permitting glial differentiation of P19 cells (Nye et al., 1994, Development 120:2421-2430).

The intracellular domain is thought to be transported to the nucleus where it appears to regulate transcription by interacting with a number of molecular targets, including CBF1/RBP-Jκ (Struhl and Adachi, 1998, Cell 93:649-660; Schroeter et al., 1998, Nature 393:382-386 Fortini et al., 1993, Nature 365:555-7). The downstream targets are not completely determined, but RBP-JK is known to activate expression of Hairy Enhancer of Split (HES) which functions as an inhibitor of transcriptional activity (Jarriault et al., 1998, Mol Cell Biol. 18:2230-9). RBP-Jκ, (as stated, also known as CBF1, the homolog of the *Drosophila* gene Suppressor of Hairless), is a mammalian DNA binding protein involved in the Epstein-Barr virus-induced immortalization of B cells. It has been demonstrated that, at least in cultured cells, Suppressor of Hairless associates with the cdc10/ankyrin repeats in the cytoplasm and translocates into the nucleus upon the interaction of the Notch receptor with its ligand Delta on adjacent cells (Fortini and Artavanis, 1994, Cell 79:273-282). The association of Hairless, a nuclear protein, with Suppressor of Hairless has been documented using the yeast two hybrid system therefore, it is believed that the involvement of Suppressor of Hairless in transcription is modulated by Hairless (Brou et al., 1994, Genes Dev. 8:2491; Knust et al. 1992, Genetics 129:803). It is known that Notch signaling results in the activation of at least certain bHLH genes within the Enhancer of split complex (Delidakis et al., 1991, Genetics 129:803). Mastermind encodes a novel ubiquitous nuclear protein whose relationship to Notch signaling remains unclear but is involved in the Notch pathway as shown by genetic analysis (Smoller et al., 1990, Genes Dev. 4:1688).

There is also evidence that Notch signaling is mediated by an alternative, HES independent pathway, that involves signaling through Deltex and results in repression of E protein activity, e.g. in a B-cell system, it has also been shown that Deltex and not RBP-Jκ, is responsible for inhibiting E47 function (Ordentlich et al., 1998, Mol Cell Biol 18:2230-9). Deltex is a cytoplasmic protein which contains a ring zinc finger and interacts with the ankyrin repeats of Notch (Matsuno et al., 1995, Development 121: 2633-2644).

2.1.3. Roles of Notch Family Members

U.S. Pat. No. 5,780,300 describes the roles of Notch proteins in differentiation processes. Briefly, Notch regulates the competence of many different cell types to respond to differentiation/proliferation/apoptosis signals, with the particular cell fates chosen depending upon the developmental history of each cell type and the specific signaling pathways operating within it. In *Drosophila* and *C. elegans*, members of the Notch/lin-12 family are required at multiple steps during the differentiation of a variety of tissues when specific cell fates are being determined. In *C. elegans*, the Notch-related genes lin-12 and glp-1 function in a wide variety of cell-cell interactions that result in the inhibition or expression of one or more potential cell fates (Greenwald and Rubin, 1992, Cell 68:271-81; Greenwald et al., 1983, Cell 34:435-444; Austin and Kimble, 1987, Cell 51:589-99; Yochem and Greenwald, 1989, Cell 58:553-563; Wilkinson et al., 1994, Cell 79:1187-1198). One particularly clear example is in the interactions involved in specifying cell fates in the developing vulva, wherein two equivalent multipotent precursors always form one anchor cell (AC) and one ventral uterine precursor (VU) cell (Greenwald and Rubin, 1992, Cell 68:271-81; Greenwald et al., 1983, Cell 34:435-44; Austin and Kimble, 1987, Cell 51:589-99; Yochem and Greenwald, 1989, Cell 58:553-63; Wilkinson et al., 1994, Cell 79:1187-98). If one of the stem cells is eliminated, the remaining cell always becomes an AC; if lin-12 activity is lacking, both become an AC; and if lin-12 activity is elevated, both cells express the VU fate. Further evidence indicates that a relative increase in expression of the ligand for lin-12, lag-2, in the cell committing to AC differentiation induces, via direct cell-cell interaction, an increase in lin-12 activity, which is inhibitory to AC differentiation but permissive for VU differentiation.

In *Drosophila*, Notch has been shown to be required for appropriate cell-fate decisions in numerous tissues, including the nervous system, eye, mesoderm, ovaries and other areas where multipotent progenitors are making cell-fate decisions (Artavanis-Tsakonas et al., 1999, Science 284: 770-776; Go et al., 1998, Development 125:2031-2040; Doherty et al., 1996, Genes Dev. 10:421-434; Artavanis-Tsakonis et al., 1995, Science 268:225-232; Greenwald and Rubin, 1992, Cell 68:271-81; Heitzler and Simpson, 1991, Cell 64:1083-1092; Artavanis-Tsakonas and Simpson, 1991, Trends Genet. 7:403-408; Cagan and Ready, 1989, Genes Dev. 3:1099-1112). In the neurogenic region, for example, the differential expression of Notch appears to mediate a lateral inhibition in which a single cell within a cluster of equivalent cells adopts a neural fate while adjacent cells adopt epidermal fates. Similarly, in embryos with a homozygous null mutation of the Notch gene, all cells in the neurogenic region become neuroblasts and not epidermal precursors.

In *Xenopus*, the expression of mutant forms of Notch in developing embryos interferes profoundly with normal development (Coffman et al., 1993, Cell 73:659).

Studies of the expression of Notch-1, one of three known vertebrate homologs of Notch, in zebrafish and *Xenopus*, have shown that the general patterns are similar; with Notch expression associated in general with non-terminally differentiated, proliferative cell populations. Tissues with high expression levels include the developing brain, eye and neural tube (Coffman et al., 1990, Science 249:1438-1441; Bierkamp et al., 1993, Mech. Dev. 43:87-100). While studies in mammals have shown the expression of the corresponding Notch homologs to begin later in development, the proteins are expressed in dynamic patterns in tissues undergoing cell fate determination or rapid proliferation (Weinmaster et al., 1991, Development 113:199-205; Reaume et al., 1992, Dev. Biol. 154:377-387; Stifani et al., 1992, Nature Genet. 2:119-127; Weinmaster et al., 1992, Development 116:931-941; Kopan et al., 1993, J. Cell Biol. 121:631-641; Lardelli et al., 1993, Exp. Cell Res. 204:364-372; Lardelli et al., 1994, Mech. Dev. 46:123-136; Henrique et al., 1995, Nature 375:787-790; Horvitz et al., 1991, Nature 351:535-541; Franco del Amo et al., 1992, Development 115:737-744). Among the tissues in which mammalian Notch homologs are first expressed are the pre-somitic mesoderm and the developing neuroepithelium of the embryo. In the pre-somitic mesoderm, expression of Notch-1 is seen in all of the migrated mesoderm, and a particularly dense band is seen at the anterior edge of pre-somitic mesoderm. This expression has been shown to decrease once the somites have formed, indicating a role for Notch in the differentiation of somatic precursor cells (Reaume et al., 1992, Dev. Biol. 154:377-387; Horvitz et al., 1991, Nature 351:535-541). Similar expression patterns are seen for mouse Delta (Simske et al., 1995, Nature 375: 142-145).

Within the developing mammalian nervous system, expression patterns of Notch homolog have been shown to be prominent in particular regions of the ventricular zone of the spinal cord, as well as in components of the peripheral nervous system, in an overlapping but non-identical pattern. Notch expression in the nervous system appears to be limited to regions of cellular proliferation, and is absent from nearby populations of recently differentiated cells (Weinmster et al., 1991, Development 113:199-205; Reaume et al., 1992, Dev. Biol. 154:377-387; Weinmaster et al., 1992, Development 116:931-941; Kopan et al., 1993, J. Cell Biol. 121:631-641; Lardelli et al., 1993, Exp. Cell Res. 204:364-372; Lardelli et al., 1994, Mech. Dev. 46:123-136; Henrique et al., 1995, Nature 375:787-790; Horvitz et al., 1991, Nature 351:535-541). A rat Notch ligand is also expressed within the developing spinal cord, in distinct bands of the ventricular zone that overlap with the expression domains of the Notch genes. The spatio-temporal expression pattern of this ligand correlates well with the patterns of cells committing to spinal cord neuronal fates, which demonstrates the usefulness of Notch as a marker of populations of cells for neuronal fates (Henrique et al., 1995, Nature 375:787-790). This has also been suggested for vertebrate Delta homologs, whose expression domains also overlap with those of Notch-1 (Larsson et al., 1994, Genomics 24:253-258; Fortini et al., 1993, Nature 365:555-557; Simske et al., 1995, Nature 375: 142-145). In the cases of the *Xenopus* and chicken homologs, Delta is actually expressed only in scattered cells within the Notch-1 expression domain, as would be expected from the lateral specification model, and these patterns "foreshadow" future patterns of neuronal differentiation (Larsson et al., 1994, Genomics 24:253-258; Fortini et al., 1993, Nature 365:555-557).

Other vertebrate studies of particular interest have focused on the expression of Notch homologs in developing sensory structures, including the retina, hair follicles and tooth buds. In the case of the *Xenopus* retina, Notch-1 is expressed in the undifferentiated cells of the central marginal zone and central retina (Coffman et al., 1990, Science 249:1439-1441; Mango et al., 1991, Nature 352:811-815). Studies in the rat have also demonstrated an association of Notch-1 with differentiating cells in the developing retina and have been interpreted to suggest that Notch-1 plays a role in successive cell fate choices in this tissue (Lyman et al., 1993, Proc. Natl. Acad. Sci. USA 90:10395-10399).

A detailed analysis of mouse Notch-1 expression in the regenerating matrix cells of hair follicles was undertaken to examine the potential participation of Notch proteins in epithelial/mesenchymal inductive interactions (Franco del Amo et al., 1992, Development 115:737-744). Such a role had originally been suggested for Notch-1 based on its expression in rat whiskers and tooth buds (Weinmaster et al., 1991, Development 113:199-205). Notch-1 expression was instead found to be limited to subsets of non-mitotic, differentiating cells that are not subject to epithelial/mesenchymal interactions, a finding that is consistent with Notch expression elsewhere.

The human homolog of Notch-1 (TAN-1) was initially cloned from a T-cell leukemia with a translocation involving this gene and subsequently found in a variety of adult tissues, but in greatest amounts in thymus and lymph node (Ellisen et al., 1991, Cell 66:649-661; Zhong et al., 1997, Development 124:1887-1897; Vargesson et al., 1998, Mech Dev. 77:197-9; Lewis et al., 1998, Mech Dev. 78:159-163; Lindsell et al., 1996, Mol. Cell. Neurosci. 8:14-27; Hasserjian et al., 1996, Blood. 88:970-976). A homolog of Notch/TAN-1 is expressed in human CD34+ hematopoietic precursors (Milner et al., 1994, Blood 83:2057-2062) as well as CD34− bone marrow cells (Milner et al., 1994, Blood 83:2057-2062; Varnum-Finney et al., 1998, Blood 91:4084-4091). Subsequent studies demonstrated widespread expression of Notch-1 and Notch-2 protein during hematopoietic development, as well as the Notch ligand, Jagged-1, in hematopoietic stroma (Varnum-Finney et al., 1998, Blood 91:4084-4091; Li et al., 1998, Immunity 8:43-55). The preferential expression of vertebrate Notch homologs in tissues undergoing cellular proliferation and differentiation suggests that these molecules are involved in mediating cell-fate decisions in vertebrates as they do in invertebrates. This persistence in tissues that are mitotically active also suggests that Notch may be involved in regulating cell proliferation. Consistent with this notion is the oncogenic phenotype associated with deregulated expression of the cytoplasmic domain of Notch-1 and, in mice, of the Notch-related int-3 locus which is a common integration site for mouse mammary tumor viruses in virus-induced tumors (Jhappan et al., 1992, Genes Dev. 6:345-355; Robbins et al., 1992, J. Virol. 66:2594-2599).

Additional studies of human Notch-1 and Notch-2 expression have been performed on adult tissue sections including both normal and neoplastic cervical and colon tissue. Notch-1 and Notch-2 appear to be expressed in overlapping patterns in differentiating populations of cells within squamous epithelia of normal tissues that have been examined and are clearly not expressed in normal columnar epithelia, except in some of the precursor cells. Both proteins are expressed in neoplasias, in cases ranging from relatively benign squamous metaplasias to cancerous invasive adenocarcinomas in which columnar epithelia are replaced by these tumors (Gray et al., 1999, Am. J. Pathol. 154:785-794; Zagouras et al., 1995, Proc. Natl. Acad. Sci. USA 92:6414-6418).

2.1.4. Notch Functions in Hematopoiesis

Evidence of Notch-1 mRNA expression in human CD34+ precursors has led to speculation for a role for Notch signaling in hematopoiesis (Milner et al., 1994, Blood 3:2057-62). This is further supported by the demonstration that Notch-1 and -2 proteins are present in hematopoietic precursors and, in higher amounts, in T cells, B cells, and monocytes, and by the demonstration of Jagged-1 protein in hematopoietic stroma (Ohishi et al., 2000, Blood 95:2847-2854; Varnum-Finney et al., 1998, Blood 91:4084-91; Li et al., 1998, Immunity 8:43-55).

The clearest evidence for a physiologic role of Notch signaling has come from studies of T cell development which showed that activated Notch-1 inhibited B cell maturation but permitted T cell maturation (Pui et al., 1999, Immunity 11:299-308). In contrast, inactivation of Notch-1 or inhibition of Notch-mediated signaling by knocking out HES-1 inhibited T cell development but permitted B cell maturation (Radtke et al., 1999, Immunity 10: 47-58; Tomita et al., 1999, Genes Dev. 13:1203-10). These opposing effects of Notch-1 on B and T cell development raise the possibility that Notch-1 regulates fate decisions by a common lymphoid progenitor cell.

Other studies in transgenic mice have shown that activated Notch-1 affects the proportion of cells assuming a CD4 vs. CD8 phenotype as well as an αβ vs. γΔ cell-fate (Robey et al., 1996, Cell 87:483-92; Washburn et al., 1997, Cell 88:833-43). Although this may reflect an effect on fate decisions by a common precursor, more recent studies have suggested that these effects may result from an anti-apoptotic effect of Notch-1 that enables the survival of differentiating T cells that would otherwise die (Deftos et al., 1998, Immunity 9:777-86; Jehn et al., 1999, J. Immunol. 162:635-8).

Evidence supporting a critical role for Notch signaling in myelopoiesis is less clear. In vivo studies involving overexpression or inactivation of Notch-1 have not identified significant effects of Notch-1 signaling on the development of mature myeloid elements, despite profound effects on T and B cell development (Pui et al., 1999, Immunity 11:299-308; Radtke et al., 1999, Immunity 10:547-58). However, in vitro studies have demonstrated effects of constitutively active Notch-1 forms on myelopoiesis. Constitutive overexpression of an activated form of Notch-1 inhibited G-CSF-induced granulocytic differentiation of murine 32D cells (Milner et al., 1996, Proc Natl Acad Sci U.S.A. 93:13014-9). More recent studies suggest that overexpression of the constitutively active intracellular domain of Notch-1 inhibits the differentiation of isolated murine hematopoietic precursors and enhances the generation of early precursor cells, including in vivo repopulating cells (Milner et al., 1996, Proc. Natl. Acad. Sci. U.S.A. 93:13014-13019; Bigas et al., 1998, J. Mol. Cell. Biol. 18:2324-2333). Thus, the lack of identifiable effects of Notch-1 on the in vivo generation of mature myeloid elements may result from compensatory effects due to other factors such as cytokines which may mask the effects of Notch activation in less mature precursors.

Studies have also shown that the differentiation of isolated hematopoietic precursor cells can be inhibited by ligand-induced Notch signaling. Coculture of murine marrow precursor cells (lin-Sca-1+ c-kit+) with 3T3 cells expressing human Jagged-1 led to a 2 to 3 fold increase in the formation of primitive precursor cell populations (Varnum-Finney et al., 1998, Blood 91:4084-4991; Jones et al., 1998, Blood 92:1505-11). Incubation of sorted precursors with beads coated with the purified extracellular domain of human Jagged-1 also led to enhanced generation of precursor cells (Varnum-Finney et al., 1998, Blood 91:4084-91).

In a study of human CD34+ cells, expression of the intracellular domain of Notch-1 or exposure to cells that overexpressed Jagged-2 also led to enhanced generation of precursor cells and prolonged maintenance of CD34 expression (Carlesso et al., 1999, Blood 93:838-48). In another study, the effects of Jagged-1-expressing cells on CD34+ cells were influenced by the cytokines present in the cultures; in the absence of added growth factors, the interaction with cell-bound Jagged-1 led to maintenance of CD34+ cells in a non-proliferating, undifferentiated state, whereas the addition of c-kit ligand led to a 2-fold increase in erythroid colony-forming cells (Walker et al., 1999, Stem Cells 17:162-71).

Studies of more mature myeloid elements have also indicated a potential role for Notch signaling in regulating their cell-fate decisions. In those studies, immobilized, truncated Delta-1 inhibited the differentiation of CD14+monocytes into macrophages and induced apoptosis in the presence of specific cytokines (Ohishi et al., 2000, Blood 95:2847-2854). Further, ligand-induced Notch signaling is permissive for differentiation of monocytes into dendritic cells in the context of appropriate cytokine stimulation. Thus, as observed in other developing systems, Notch signaling appears to inhibit differentiation along a particular pathway, allowing cells to remain undifferentiated or to differentiate along the uninhibited, default pathway.

Notch signaling has been shown to play a central role in cell fate decisions in numerous developmental systems. The evolutionarily conserved Notch transmembrane receptors are known to play roles in differentiation, proliferation, and apoptotic events. In general, Notch signaling inhibits differentiation along a particular pathway, allowing the cell to remain undifferentiated or differentiate along an alternate pathway in response to specific environmental cues. Notch signaling is induced following receptor ligand interaction, causing proteolytic cleavage and release of an active intracellular domain which is transported to the nucleus and interacts with a number of downstream targets, including the transcriptional regulator, RBP-Jκ. At present, four paralogs of the Notch gene have been identified in vertebrates (Notch-1-4). The ligands for Notch are also transmembrane proteins and include Jagged-1 and -2, and Delta-1, -2, and -3. Evidence of expression of Notch-1 mRNA in human CD34+ precursors has led to speculation for a role for Notch signaling in hematopoiesis. Further studies have demonstrated Notch-1 and -2 protein in hematopoietic precursors and, in higher amounts, in T cells, B cells, and monocytes, as well as showing Jagged-1 to be expressed in hematopoietic stroma. The clearest evidence for a physiologic role of Notch signaling has come from studies of T cell development where Notch-1 mediated signaling is required for T cell development and affects CD4/CD8 and $\alpha\beta/\gamma\Delta$ cell fate decisions, and constitutively active forms of Notch-1 induce T cell lymphomas. In addition, overexpression of a constitutively active Notch-1 form inhibits B cell maturation, suggesting that Notch-1 may regulate fate decisions by a common lymphoid progenitor cell. Evidence supporting a critical role for Notch signaling in myelopoiesis is less clear. Constitutive overexpression of an activated Notch-1 form inhibits G-CSF-induced granulocytic differentiation of 32D cells, and the differentiation of isolated hematopoietic precursors. The differentiation of precursor cells is also inhibited by ligand-induced Notch signaling. Coculture of murine marrow precursor cells (sca-1+ lin– c-kit+) with a 3T3 cell layer that expresses human Jagged-1 or incubating sorted precursors with beads coated with the purified extracellular domain of human Jagged-1 leads to a 2-3 fold increase in the formation of primitive precursor cell populations. Immobilized, truncated forms of the Notch ligand, Delta-1, were found to inhibit the differentiation of isolated precursors, allowing a substantial increase in the number of sca-1+lin– cells.

2.2 Cellular Differentiation During Development

The developmental processes that govern the ontogeny of multicellular organisms, including humans, depend on the interplay between signaling pathways, which gradually narrow the developmental potential of cells from the original totipotent stem cell to the terminally differentiated mature cell, which performs a specialized function, such as a heart cell or a nerve cell.

The fertilized egg is the cell from which all other cell lineages derive, i.e., the ultimate stem cell. As development proceeds, early embryonic cells respond to growth and differentiation signals which gradually narrow the cells' developmental potential, until the cells reach developmental maturity, i.e., are terminally differentiated. These terminally differentiated cells have specialized functions and characteristics, and represent the last step in a multi-step process of precursor cell differentiation into a particular cell.

The transition from one step to the next in cell differentiation is governed by specific biochemical mechanisms which gradually control the progression until maturity is reached. It is clear that the differentiation of tissues and cells is a gradual process which follows specific steps until a terminally differentiated state is reached.

Gastrulation, the morphogenic movement of the early embryonic cell mass, results in the formation of three distinct germ cell layers, the ectoderm, the mesoderm, and the endoderm. As cells in each germ cell layer respond to various developmental signals, specific organs are generated which are composed of specific differentiated cells. For example, the epidermis and the nervous system develop from ectoderm-derived cells, the respiratory system and the digestive tract are developed from endoderm-derived cells, and mesoderm-derived cells develop into the connective tissues, the hematopoietic system, the urogenital system, muscle, and parts of most internal organs.

The neural crest derives from the ectoderm and is the cell mass from which an extraordinary large and complex number of differentiated cell types are produced, including the peripheral nervous system, pigment cells, adrenal medulla and certain areas of the head cartilage.

The pluripotentiality of neural crest cells is well established (LeDouarin et al., 1975, Proc. Natl. Acad. Sci. USA 72:728-732). A single neural crest cell can differentiate into several different cell types.

The epidermis consists of several cellular layers which define a differentiation lineage starting from the undifferentiated, mitotically active basal cells to the terminally differentiated non-dividing keratinocytes.

The endoderm is the source of the tissues that line two tubes within the adult body. The digestive tube extends throughout the length of the body. The digestive tube gives rise not only to the digestive tract but also to, for example, the liver, the gallbladder and the pancreas. The second tube, the respiratory tube, forms the lungs and part of the pharynx. The pharynx gives rise to the tonsils, thyroid, thymus, and parathyroid glands.

The genesis of the mesoderm which has also been referred to as the mesengenic process gives rise to a very large number of internal tissues which cover all the organs between the ectodermal wall and the digestive and respiratory tubes.

Embryonic development produces the fully formed organism. The morphologic processes that define the cellular boundaries of each organ include not only proliferation and differentiation, but also apoptosis (programmed cell death). For example, in the nervous system, approximately 50% of neurons undergo programmed cell death during embryogenesis.

In the juvenile or adult individual, the maintenance of tissues, whether during normal life or in response to injury and disease, depends on the replenishing of the organs from precursor cells that are capable of responding to specific developmental signals.

The best known example of adult cell renewal via the differentiation of immature cells is the hematopoietic system. Here, developmentally immature precursors (hematopoietic stem and progenitor cells) respond to molecular signals to gradually form the varied blood and lymphoid cell types.

During hematopoietic development, the progeny of pluripotent stem cells progressively lose their proliferative potential and capacity for self-renewal, and display greater commitment to a given differentiation pathway. The factors that regulate this commitment to the various hematopoietic lineages are not understood, but are thought to include stochastic processes and interactions with soluble and cell-bound cytokines (Fairbairn et al., 1993, Cell 4:823-32; Ogawa, 1993, Blood 81:2844-53; Metcalf, 1989, Nature 339:27-30; Metcalf, 1993, Blood. 82:3515-23; Goldsmith et al., 1998, Proc. Natl. Acad. Sci. USA. 95:7006-11; Socolovsky et al., 1997, J. Biol. Chem. 272:14009-12).

While the hematopoietic system is the best understood self renewing adult cellular system it is believed that most, perhaps all, adult organs harbor precursor cells that under the right circumstances, can be triggered to replenish the adult tissue. For example, the pluripotentiality of neural crest cells has been described above. The adult gut contains immature precursors which replenish the differentiated tissue. Liver has the capacity to regenerate because it contains hepatic immature precursors; skin renews itself, etc. Through the mesengenic process, most mesodermal derivatives are continuously replenished by the differentiation of precursors. Such repair recapitulates the embryonic lineages and entails differentiation paths which involve pluripotent progenitor cells.

Mesenchymal progenitor cells are pluripotent cells that respond to specific signals and adopt specific lineages. For example, in response to bone morphogenic factors, mesenchymal progenitor cells adopt a bone forming lineage. For example, in response to injury, mesodermal progenitor cells can migrate to the appropriate site, multiply and react to local differentiation factors, consequently adopting a distinct differentiation path.

It has been suggested that the reason that only a limited tissue repair is observed in adults is because there are too few progenitor cells which can adopt specific differentiation lineages. It is clear that if these cells can be expanded by immortalizing them in culture, then tissue repair could be facilitated by transplantation of the cultured cells. However, diploid cells generally have a limited proliferative capacity in vitro. Following initial culturing, the cells undergo a series of rapid cycling, which slows down until the population undergoes a growth arrest, which is a result of a block at the G1/S or G2/M phases of mitosis (Derventz et al., 1996, Anticancer Res. 16:2901-2910). For example, after a limited number of divisions, human fibroblasts enter a nonreplicative state as a result of cellular senescence. When certain viral oncogenes are expressed in the fibroblasts, the replicative life span is extended, but the cells still enter a nonreplicative state termed a "crisis" state (Wei and Sedivy, 1999, Exp Cell Res 253:519-522). The number of cell cycles a cell undergoes before reaching the growth arrest phase depends on the cell type; for human cells, the number is generally between 30 and 60 (Derventz et al., 1996, Anticancer Res. 16:2901-2910 and reference cited therein). Therefore, the process of immortalizing pluripotent or multipotent cells, such as stem or progenitor cells of a desired type, ex vivo would give rise to more rapid proliferation of the desired cell type and allow for more rapid treatment injuries or traumas. Additionally, the ability would give rise to the potential for treating many human diseases and could circumvent tissue rejection without the need for immunosuppressive agents.

3. SUMMARY OF THE DISCLOSURE

Described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody, or an immobilized antigen binding fragment thereof, that binds to Notch 1; and the Notch 2 agonist is an immobilized antibody, or an immobilized antigen binding fragment thereof, that binds to Notch 2. In certain embodiments, the one or more agonists are in an amount that maintains Notch signaling pathway activation levels at sub-maximal levels in the hematopoietic precursor cells.

Described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises before said culturing step a first step of detecting or measuring Notch 1 expression and/or Notch 2 expression by the hematopoietic precursor cells, wherein the one or more agonists used in said culturing step are agonists of the Notch paralog shown to be detected or expressed in said first step.

Described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly detecting or measuring Notch 1 and Notch 2 expression by said hematopoietic precursor cells during said culturing step, and using the one or more agonists in said culturing step that are agonists of the Notch paralog shown to be expressed by said hematopoietic precursor cells by the immediately preceding detecting or measuring step.

In certain embodiments, the culturing is for a time period beyond which hematopoietic precursor cells not cultured in the presence of (a)(i) the Notch 1 agonist, (ii) the Notch 2 agonist, or (iii) the Notch 1 agonist and the Notch 2 agonist, and (b) the growth factors, stop proliferating and differentiate or die.

In specific embodiments, the culturing is performed in the presence of a Notch 1 agonist and a Notch 2 agonist. In specific embodiments, the culturing is performed in the presence of a Notch 1 agonist. In specific embodiments, the culturing is performed in the presence of a Notch 2 agonist.

In certain embodiments, the hematopoietic precursor cells are obtained from bone marrow, umbilical cord blood, placental blood, or Wharton's jelly. In certain embodiments, the hematopoietic precursor cells are obtained from fetal or neonatal blood.

In certain embodiments, during the culturing, the weight ratio of the Notch 2 agonist to the Notch 1 agonist is 150:1; 140:1; 130:1; 120:1; 110:1; 100:1; 90:1; 80:1; 70:1; 60:1; 50:1; 40:1; 30:1; 25:1; 24:1; 23:1; 22:1; 21:1; 20:1; 19:1; 18:1; 17:1 16:1; 15:1; 14:1; 13:1; 12:1; 11:1; 10:1; 9:1; 8:1; 7:1; 6:1; 5:1; 4:1; 3:1; 2:1; 1.5:1; or 1.25:1. In specific embodiments, the Notch 2 agonist is at a concentration of 0.1 µg/ml to 50 µg/ml. In specific embodiments, the Notch 1 agonist is at a concentration of 0.005 µg/ml to 30 µg/ml. In specific embodiments, the Notch 2 agonist is at a concentration of 20 µg/ml. In specific embodiments, the Notch 1 agonist is at a concentration of 2.5 µg/ml, 10 µg/ml or 0.15 µg/ml. In specific embodiments, the Notch 2 agonist is at a concentration of 10 µg/ml. In specific embodiments, the Notch 1 agonist is at a concentration of 0.02 µg/ml.

In certain embodiments, the one or more growth factors are interleukin-3 (IL-3), interleukin-6 (IL-6), thrombopoietin (TPO), stem cell factor (SCF), and Flt-3 ligand. In specific embodiments, IL-3 is at a concentration of 10 ng/ml. In specific embodiments, one or more of IL-3, IL-6, TPO, SCF, and Flt-3 ligand are at a concentration of 50 ng/ml.

In certain embodiments, the culturing takes place over 7-8 days. In certain embodiments, the culturing takes place over at least five weeks. In certain embodiments, the culturing takes place over at least six weeks.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, and using the one or more agonists in said culturing step that are agonists of the Notch paralog shown to be expressed by said hematopoietic precursor cells in the first 24-72 hours of the culture period.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, and using the one or more agonists in said culturing step that are agonists of the Notch paralog shown to be expressed by said hematopoietic precursor cells in the middle 24-72 hours of the culture period.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, and using the one or more agonists in said culturing step that are agonists of the Notch paralog shown to be expressed by said hematopoietic precursor cells in the final 24-72 hours of the culture period.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, and using the one or more agonists in said culturing step that are agonists of the Notch paralog shown to be expressed by said hematopoietic precursor cells in the first third of the culture period.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, and using the one or more agonists in said culturing step that are agonists of the Notch paralog shown to be expressed by said hematopoietic precursor cells in the middle third of the culture period.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, and using the one or more agonists in said culturing step that are agonists of the Notch paralog shown to be expressed by said hematopoietic precursor cells in the final third of the culture period.

In certain embodiments, the methods disclosed herein further comprise measuring Notch signaling pathway activation in the hematopoietic precursor cells by assessing Hes1 expression.

In certain embodiments, the one or more agonists are each a monoclonal antibody. In certain embodiments, the one or more agonists are each an Fv, Fab, Fab', F(ab')2, Fc, or single chain Fv fragment (scFv). In specific embodiments, the antibody or antigen binding fragment thereof that binds to Notch 1 binds to the extracellular EGF repeat domain of Notch 1. In more specific embodiments, the antibody or antigen binding fragment thereof that binds to Notch 1 binds to EGF-like repeats 1-6 of Notch 1. In specific embodiments, the antibody or antigen binding fragment thereof that binds to Notch 2 binds to the extracellular EGF repeat domain of Notch 2. In certain embodiments, the one or more agonists are each a human, humanized, synthetic, or chimeric antibody.

In certain embodiments, wherein the culturing is performed in the presence of a Notch 1 agonist and a Notch 2 agonist, the Notch 1 agonist is immobilized on a first solid phase. In specific embodiments, wherein the culturing is performed in the presence of a Notch 1 agonist and a Notch 2 agonist, and the Notch 1 agonist is immobilized on a first solid phase, the Notch 2 agonist is immobilized on a second solid phase that is not the first solid phase. In specific embodiments, wherein the culturing is performed in the presence of a Notch 1 agonist and a Notch 2 agonist, and the Notch 1 agonist is immobilized on a first solid phase, the Notch 2 agonist is immobilized on the first solid phase. In specific embodiments, the first solid phase is the surface of a tissue culture dish or flask. In more specific embodiments, the first solid phase is the surface of a tissue culture dish or flask, and the second solid phase is a bead. In more specific embodiments, the first solid phase is a bead, and the second solid phase is the surface of a tissue culture dish or flask.

In certain embodiments, the Notch 1 agonist is capable of overcoming cis inhibition of Notch 1 in a cell line expressing Notch 1 and Delta. In certain embodiments, the Notch 1 agonist binds Notch 1 with a greater affinity than it binds to Notch 2. In certain embodiments, the Notch 1 agonist exhibits substantially no binding to Notch 2. In certain embodiments, the Notch 2 agonist binds Notch 2 with a greater affinity than it binds to Notch 1. In certain embodiments, the Notch 2 agonist exhibits substantially no binding to Notch 1.

In certain embodiments, described herein are methods for expanding hematopoietic precursor cells, comprising culturing the hematopoietic stem cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic stem cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises before said culturing step a first step of detecting or measuring Notch 1 expression and/or Notch 2 expression by the hematopoietic precursor cells, wherein the Notch 1 agonist is used in said culturing step if Notch 1 is expressed.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises before said culturing step a first step of detecting or measuring Notch 1 expression and/or Notch 2 expression by the hematopoietic precursor cells, wherein the Notch 2 agonist is used in said culturing step if Notch 2 is expressed.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises before said culturing step a first step of detecting or measuring Notch 1 expression and/or Notch 2 expression by the hematopoietic precursor cells, wherein the Notch 1 agonist and the Notch 2 agonist are used in said culturing step if both Notch 1 and Notch 2 are expressed.

In certain embodiments, described herein are methods for expanding hematopoietic precursor cells, comprising culturing the hematopoietic precursor cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic precursor cell population; wherein the Notch 1 agonist is an immobilized antibody that binds to Notch 1 or an antigen-binding fragment thereof, and the Notch 2 agonist is an immobilized antibody that binds to Notch 2 or an antigen-binding fragment thereof, which further comprises repeatedly measuring Notch 1 and Notch 2 expression by said hematopoietic precursor cells during said culturing step, wherein during said culturing step, an instance of the detecting or measuring step shows that the hematopoietic precursor cells substantially do not express Notch 2, and, after such instance, a Notch 1 agonist and not a Notch 2 agonist is used in said culturing.

In specific embodiments, the culturing is performed in the presence of a Notch 1 agonist, wherein the Notch 2 agonist is not present when the culturing is performed in the presence of a Notch 1 agonist. In specific embodiments, the culturing is performed in the presence of a Notch 2 agonist, wherein the Notch 1 agonist is not present when the culturing is performed in the presence of a Notch 2 agonist.

In specific embodiments, the hematopoietic precursor cells are human. In specific embodiments, the Notch 1 and Notch 2 are human Notch 1 and Notch 2. In specific embodiments, the growth factors are human growth factors.

In specific embodiments, the hematopoietic precursor cells are hematopoietic stem cells. In specific embodiments, the hematopoietic precursor cells are hematopoietic stem cells and hematopoietic progenitor cells. In specific embodiments, the hematopoietic precursor cells are hematopoietic progenitor cells. In specific embodiments, the hematopoietic precursor cells are short-term marrow engrafting cells. In specific embodiments, the methods described herein further produce early T cell precursors able to migrate to the thymus and generate mature T cells.

It has previously been shown that Notch signaling induced by immobilization of the extracellular domain of Delta1 (Delta1$^{ext-IgG}$) to a plastic surface generates increased numbers of hematopoietic progenitors following ex vivo culture of purified hematopoietic progenitors from murine bone marrow or human cord blood, including short term repopulating cells. Although this culture system has been used to generate a product that improves cord blood transplantation in a clinical setting, immobilized Delta1$^{ext-IgG}$ can activate to a high extent both Notch 1 and Notch 2 receptors expressed by cultured HSC, thereby also inducing differentiation programs likely inhibitory to stem cell self-renewal.

The present disclosure provides that maintenance of a low Notch signal strength leads to improved expansion and engraftment of stem cells. Because quantitative rather than qualitative differences in Notch signaling are indicated, activation of either Notch 1 and/or Notch 2 can be used to generate desired levels of Notch signaling. Further, because Notch 1 and Notch 2 receptor expression occurs independently of each other during culture, different Notch agonists can be chosen based on changing expression levels over time. In these embodiments, Notch signaling can be due to the presence of a Notch 1 agonist; a Notch 2 agonist; or a Notch 1 agonist and a Notch 2 agonist. Accordingly, and as described herein, a low level of Notch signal strength should be maintained, whether through activation of Notch 1, Notch 2 or Notch 1 and Notch 2.

The current disclosure also provides that maintenance of low Notch signal strength (which can be mediated by Notch 2 in stem cells), along with low activation of Notch 1 (whose expression increases during culture following Notch activation) leads to improved expansion and engraftment of stem cells. The results suggest careful titration of the Notch signal in stem cells by selective paralog activation is beneficial. The current disclosure shows that culture of murine bone marrow highly enriched stem (SK-SLAM) cells in wells with low amounts of Notch 1 agonist in combination with relatively higher amounts of Notch 2 agonist leads to 2-fold increased generation of SK-SLAM cells (Sca-1$^+$c-kit$^+$ CD150$^+$CD48$^-$CD11b$^-$) following 7-8 days of culture, compared to a less than 1-fold increase in cultures with Delta1$^{ext-IgG}$, Notch 2 agonist alone, or control ligands when monoclonal antibodies specific for either Notch 1 or Notch 2 receptors are immobilized to the plastic surface. Thus, Notch paralog specific activation by use of a Notch 1 agonist, a Notch 2 agonist or a Notch 1 agonist and a Notch 2 agonist provides a novel way to expand stem cells, including hematopoietic stem cells.

One particular embodiment includes a method for producing an immortalized precursor cell population comprising culturing a non-immortalized precursor cell in the presence of a Notch 1 agonist, a Notch 2 agonist, or a Notch 1 agonist and a Notch 2 agonist (and, in particular embodiments, one or more growth factors), for a time period beyond which cells of the precursor cell type not in the presence of the Notch 1 agonist, Notch 2 agonist, or Notch 1 and Notch 2 agonist (and, in particular embodiments, growth factors) stop proliferating and/or differentiate or die, such that the precursor cell proliferates but does not terminally differentiate during the time period, thereby producing an immortalized precursor cell population.

In another embodiment, during the culturing, a Notch 2 agonist is provided at a higher concentration than a Notch 1 agonist.

In another embodiment, during the culturing the ratio of Notch 2 agonist to Notch 1 agonist is 150:1; 140:1; 130:1; 120:1; 110:1; 100:1; 90:1; 80:1; 70:1; 60:1; 50:1; 40:1; 30:1; 25:1; 24:1; 23:1; 22:1; 21:1; 20:1; 19:1; 18:1; 17:1 16:1; 15:1; 14:1; 13:1; 12:1; 11:1; 10:1; 9:1; 8:1; 7:1; 6:1; 5:1; 4:1; 3:1; 2:1; 1.5:1; or 1.25:1. In a preferred embodiment, the ratio is a weight ratio.

In another embodiment, during the culturing the Notch 2 agonist is at a concentration of 0.1 µg/ml; 1 µg/ml; 5 µg/ml; 10 µg/ml; 15 µg/ml; 20 µg/ml; 25 µg/ml; 30 µg/ml; 35 µg/ml; 40 µg/ml; 45 µg/ml; 50 µg/ml; 55 µg/ml; 60 µg/ml; 65 µg/ml; 70 µg/ml; 75 µg/ml; 80 µg/ml; 85 µg/ml; 90 µg/ml; 95 µg/ml; or 100 µg/ml.

In another embodiment, during the culturing the Notch 1 agonist is at a concentration of 0.005 µg/ml; 0.05 µg/ml; 0.5 µg/ml; 1 µg/ml; 5 µg/ml; 10 µg/ml; 15 µg/ml; 20 µg/ml; 25 µg/ml; 30 µg/ml; 35 µg/ml; 40 µg/ml; 45 µg/ml; 50 µg/ml; 55 µg/ml; or 60 µg/ml.

In another embodiment, during the culturing the Notch 2 agonist is at a concentration of 20 µg/ml and the Notch 1 agonist is at a concentration of 2.5 µg/ml, 10 µg/ml or 0.15 µg/ml.

In another embodiment, during the culturing the Notch 2 agonist is at a concentration of 10 µg/ml and the Notch 1 agonist is at a concentration of 0.02 µg/ml.

In another embodiment, the one or more growth factors are IL-3; IL-6; TPO; SCF and Flt-3.

In another embodiment, during the culturing IL-3 is at a concentration of 10 ng/ml. In another embodiment, during the culturing, one or more of IL-6; TPO; SCF and Flt-3 are at a concentration of 50 ng/ml.

In another embodiment, the precursor cell population does not substantially differentiate during the time period.

In another embodiment, the precursor cell is a stem cell. In another embodiment, the precursor cell is a progenitor cell. In another embodiment, the stem cell is a hematopoietic stem cell (HSC). In another embodiment, the progenitor cell is a hematopoietic progenitor cell. In another embodiment, the hematopoietic stem or progenitor cell is obtained from bone marrow. In another embodiment, the hematopoietic stem or progenitor cell is obtained from fetal or neonatal blood.

In another embodiment, the time period is 7-8 days. In another embodiment, the time period is at least five weeks. In another embodiment, the time period is at least six weeks.

4. BRIEF DESCRIPTION OF THE FIGURES

Figure 1:
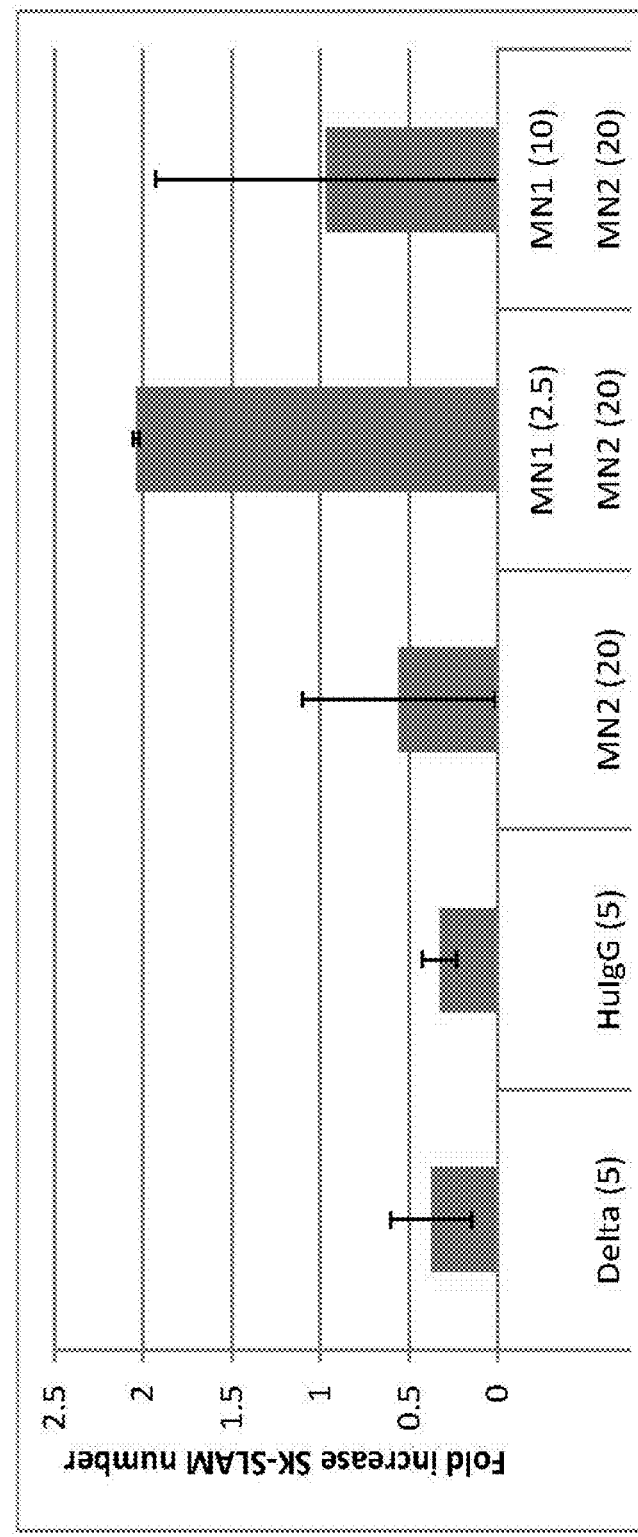
Figure 2A:
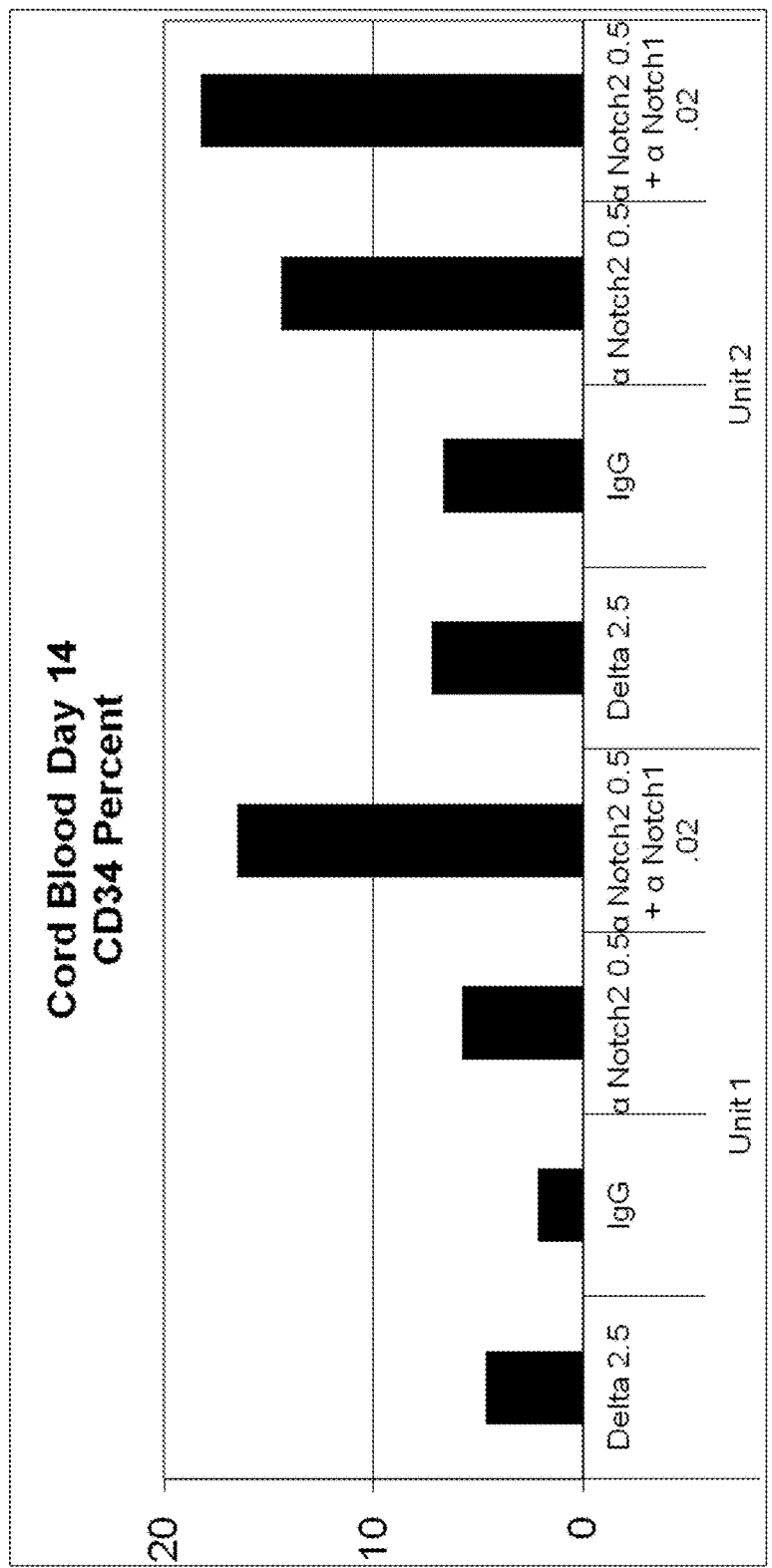
Figure 2B:
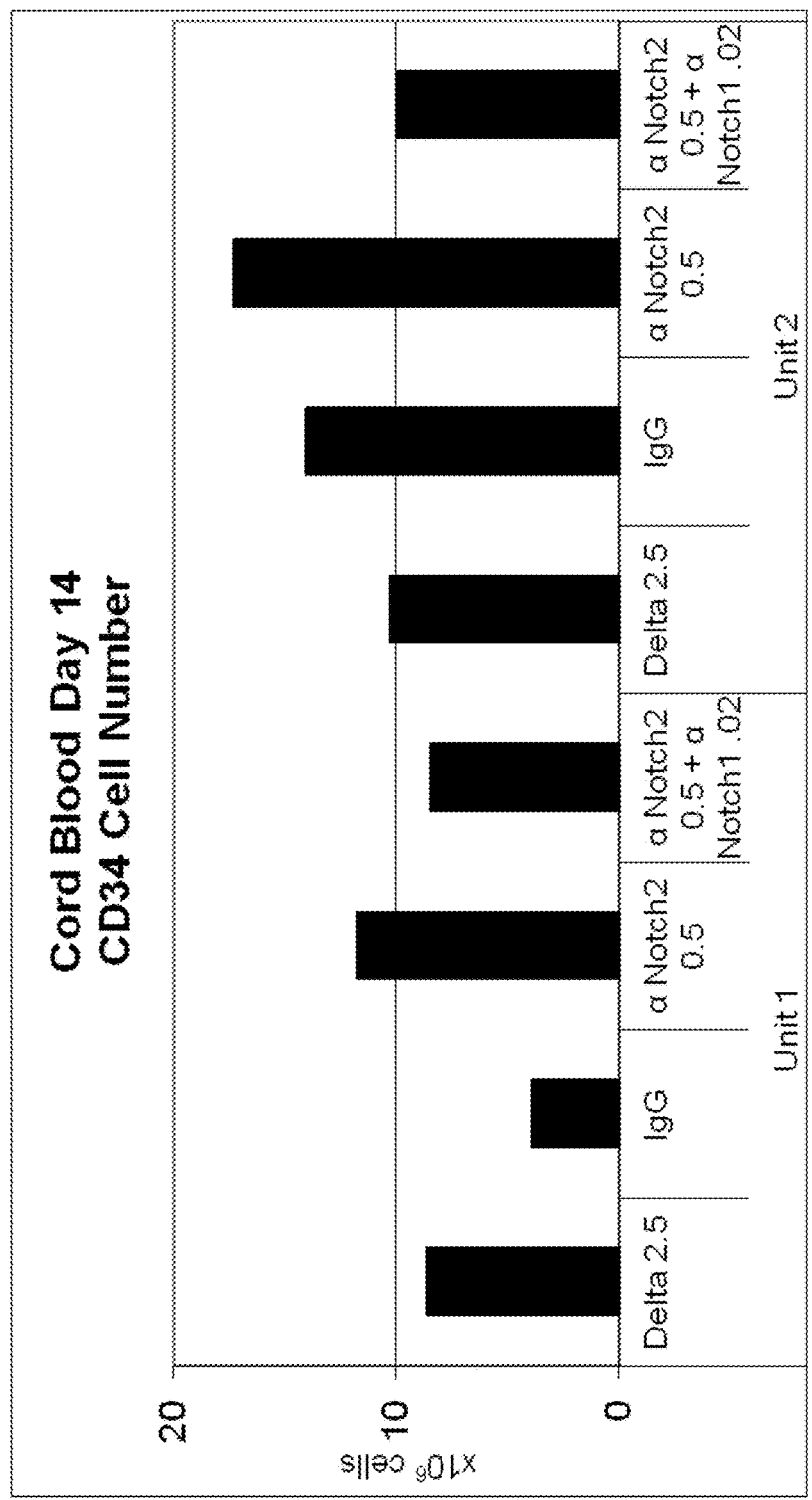
Figure 2C:
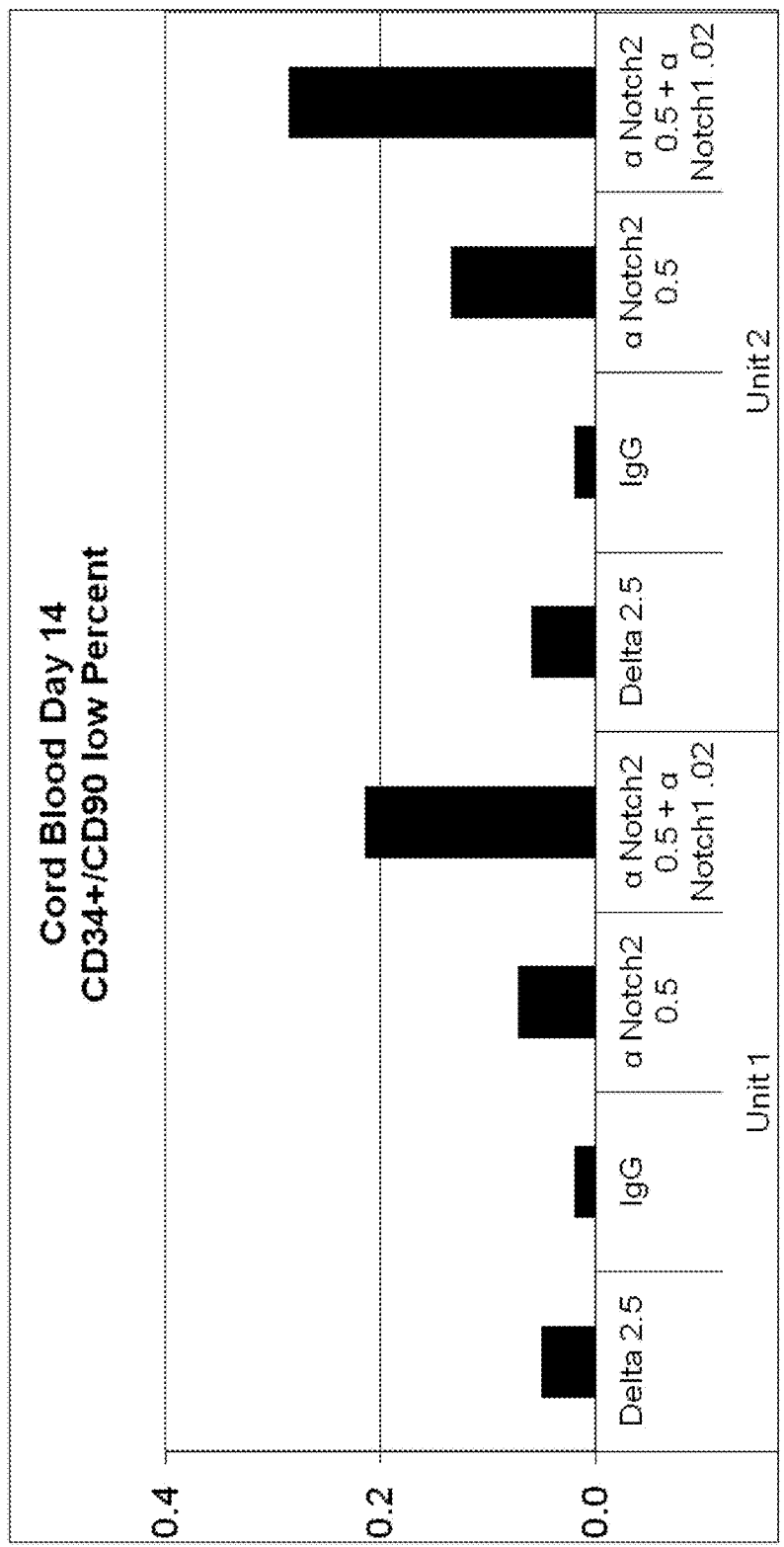
Figure 2D:
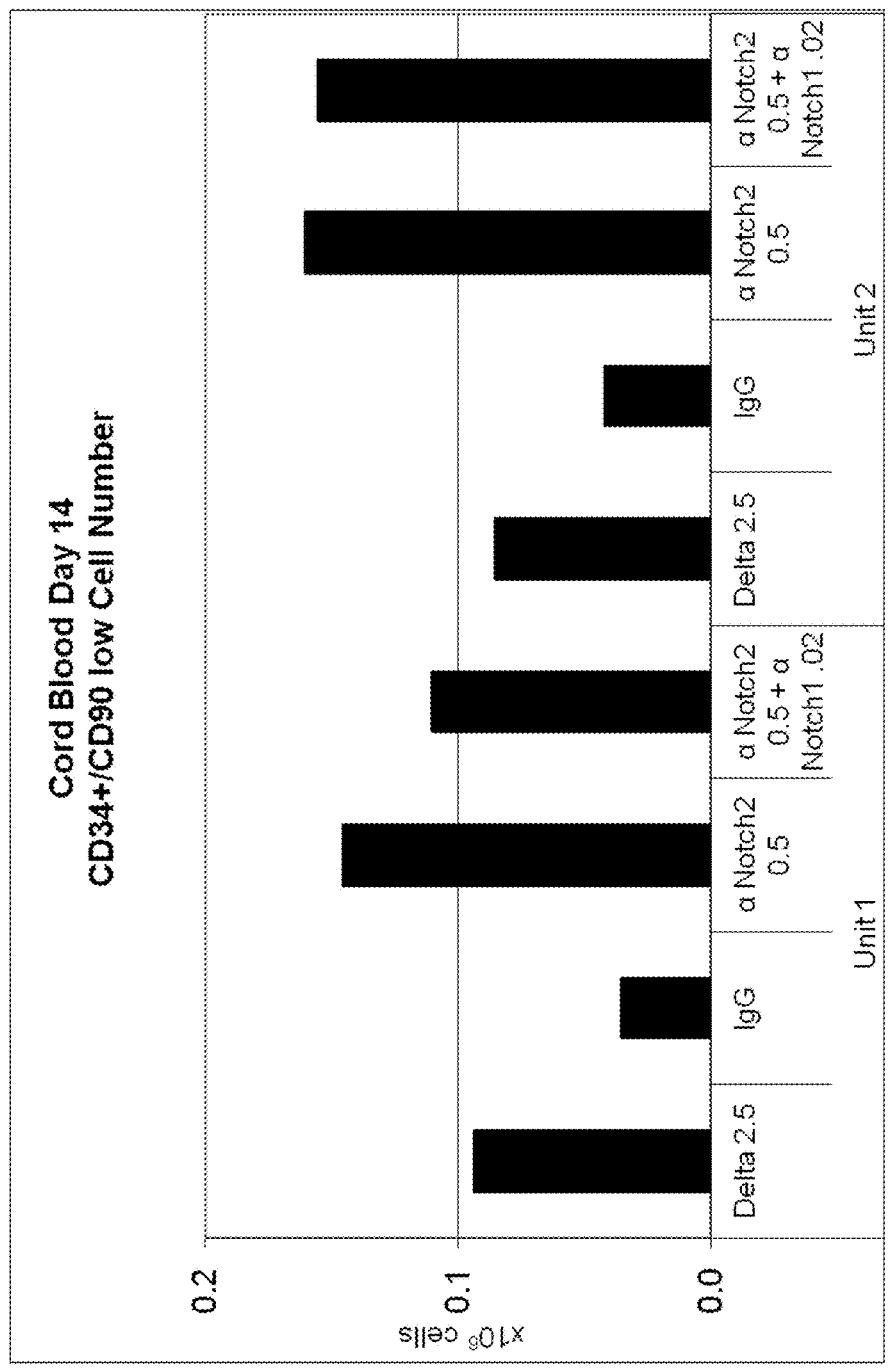

FIG. 1. Culture with specific Notch antibodies leads to increased generation of SK-SLAM (Sca-1$^+$c-kit$^+$CD150$^+$ CD48$^-$-CD11b$^-$) cells. Each bar represents the mean fold increased number of SK-SLAM cells in cultures with (i) immobilized Delta1$^{ext-IgG}$ (Delta) at 5 µg/ml, (ii) immobilized Human control IgG (HuIgG) at 5 µg/ml and indicated doses of immobilized monoclonal antibodies for (iii) Notch 2 antibodies [HMN2-35 (MN2)] or (iv) Notch 2 and Notch 1 antibodies [HMN1-12 (MN1)] (commercially available from Biolegend, San Diego, Calif.). Numbers in parentheses on x-axis are given in µg/ml. Bars are the mean fold increase compared to the initial number of SK-SLAM placed in the culture well of 2 separate experiments+/−range.

FIGS. 2A-D. Cord blood CD34$^+$ cells from two separate units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and (i) immobilized Delta1 (Delta, 2.5 µg/ml), (ii) immobilized anti-human Notch 2 (α Notch2, clone MHN2-25, 0.5 µg/ml (commercially available from Biolegend, San Diego, Calif.)), (iii) immobilized anti-human Notch 2 0.5 µg/ml combined with immobilized anti-human Notch 1 (α Notch1, clone MHN1-519 (commercially available from Biolegend, San Diego, Calif.)), or (iv) immobilized control IgG (IgG). The (A) percent and (B) number of CD34$^+$ progenitor cells was determined, as well as the (C) proportion and (D) number of the more primitive CD3$^+$/90 low cells. Numbers on x-axis are given in µg/ml.

Figure 3:
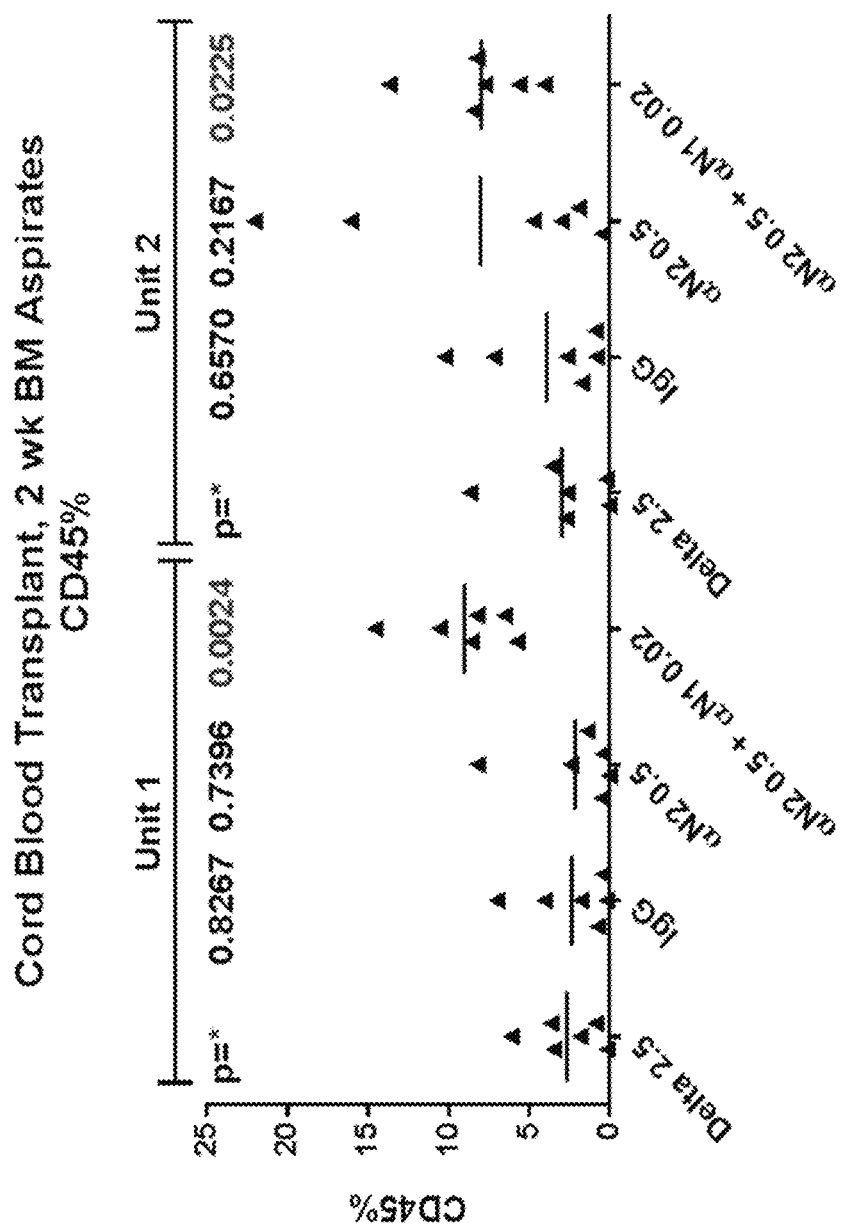
Figure 4A:
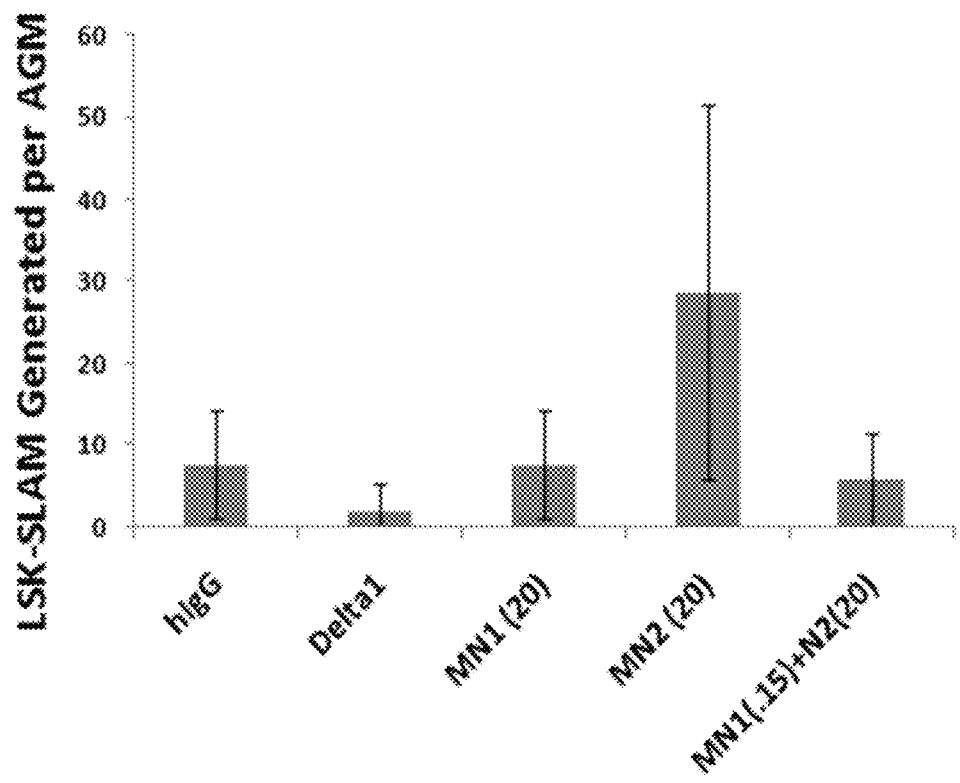
Figure 4B:
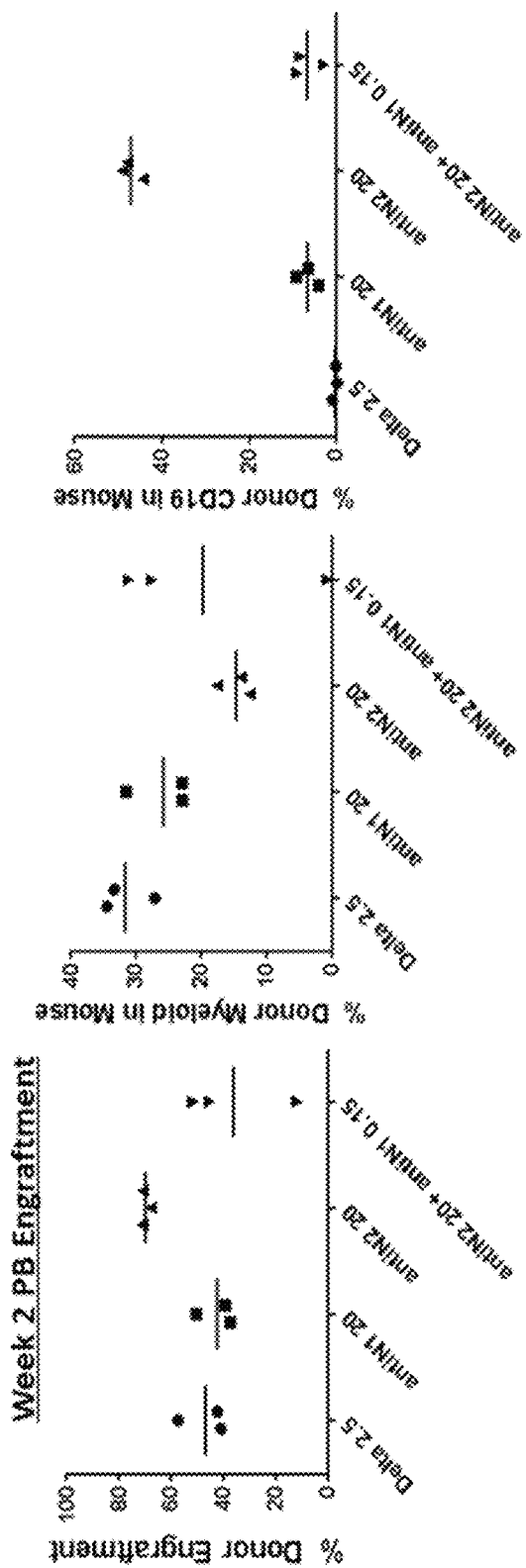
Figure 4C:
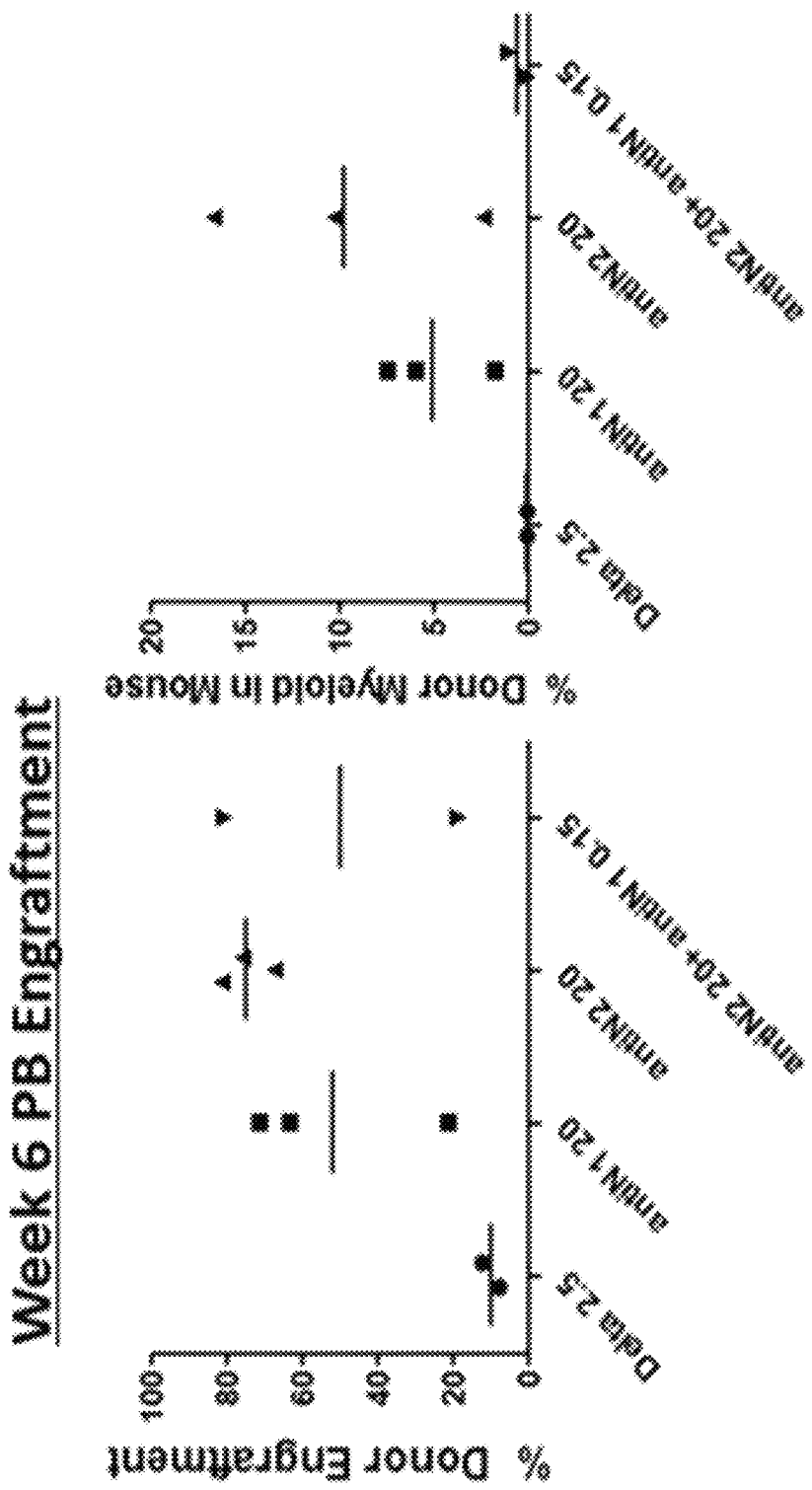
Figure 4D:
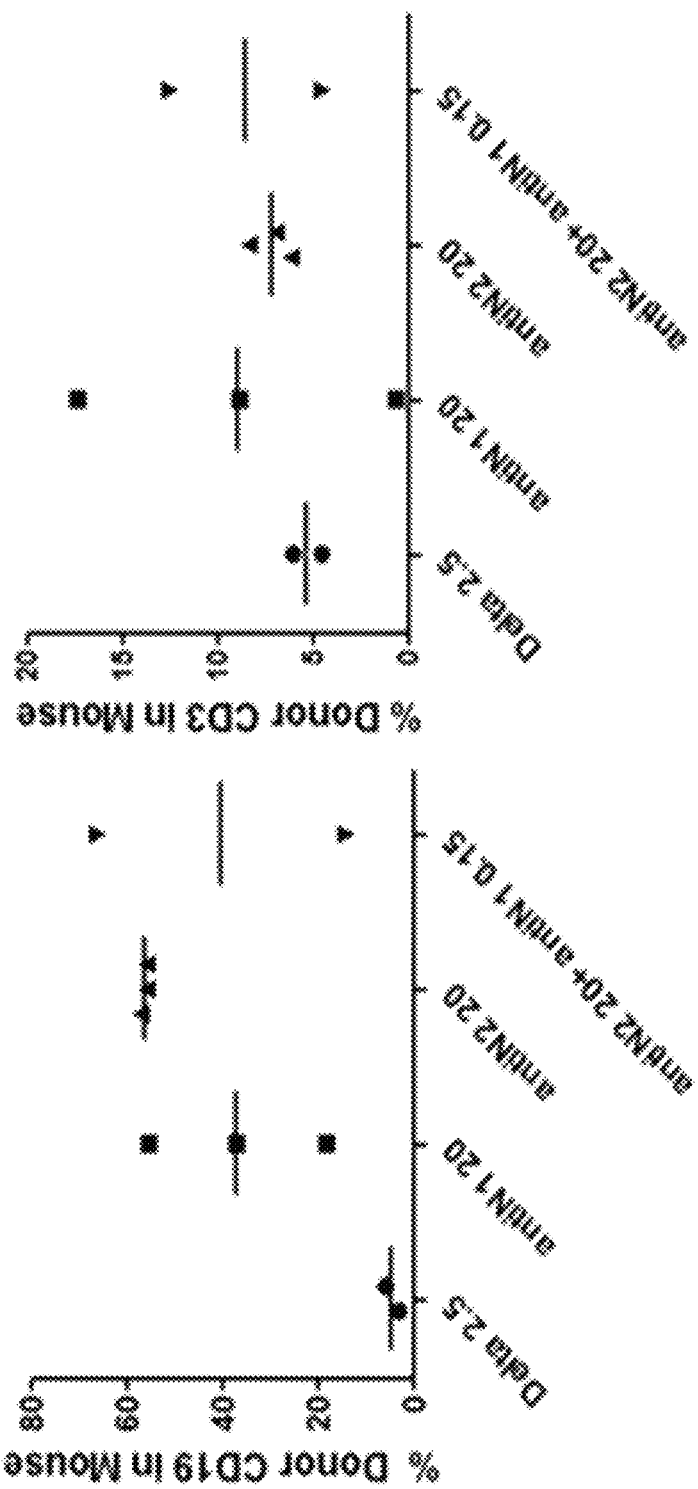
Figure 5A:
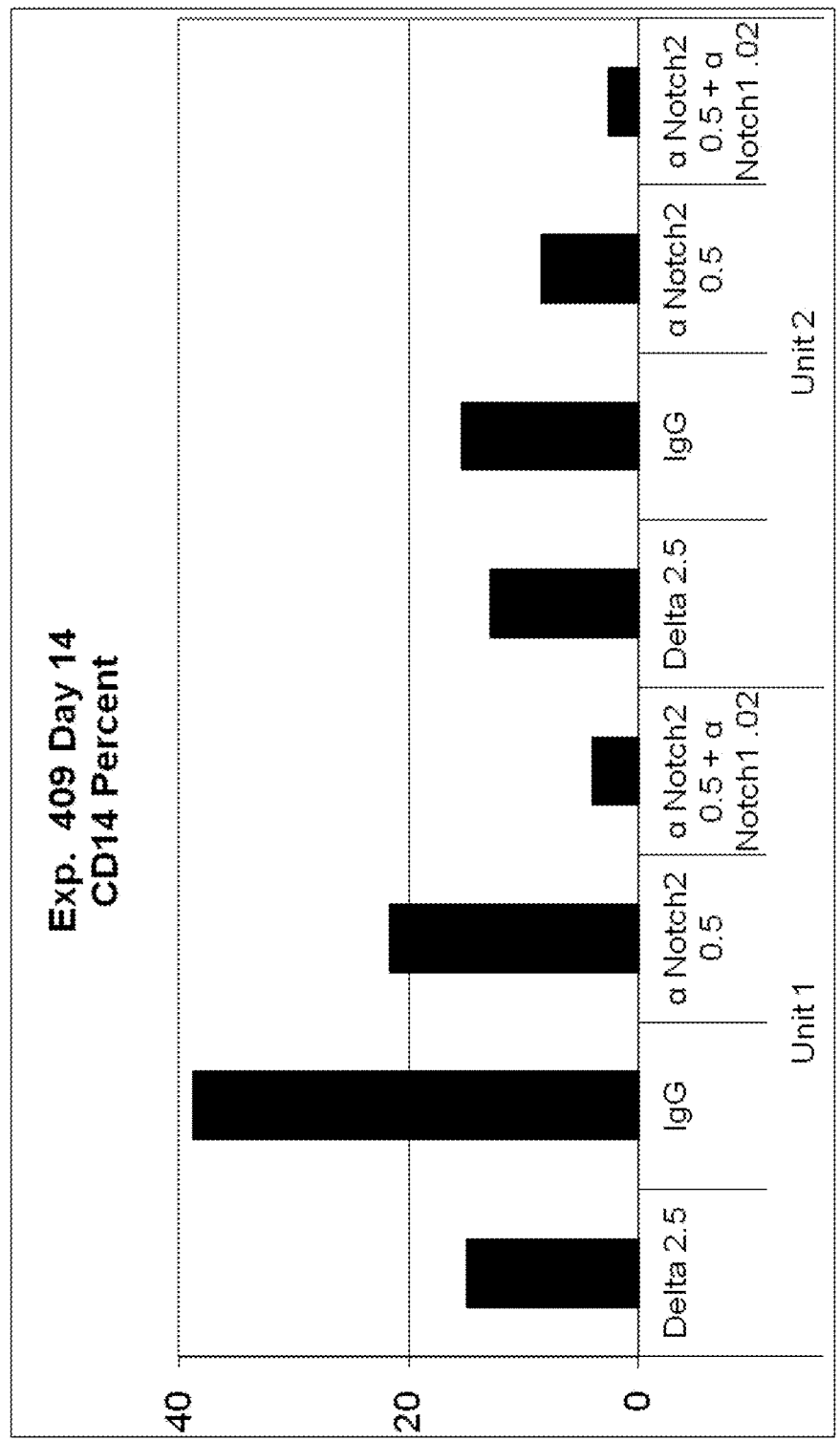
Figure 5B:
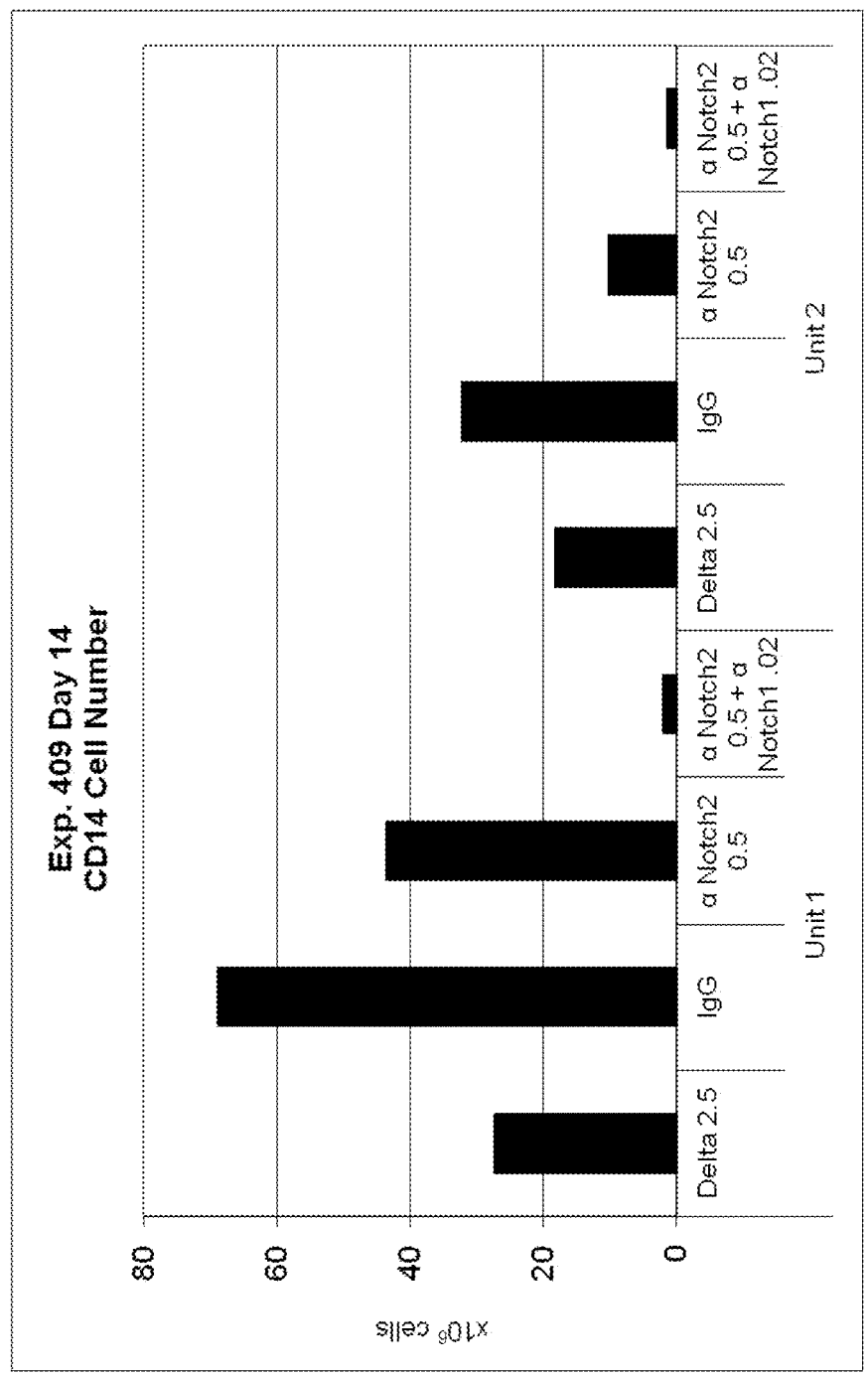
Figure 5C:
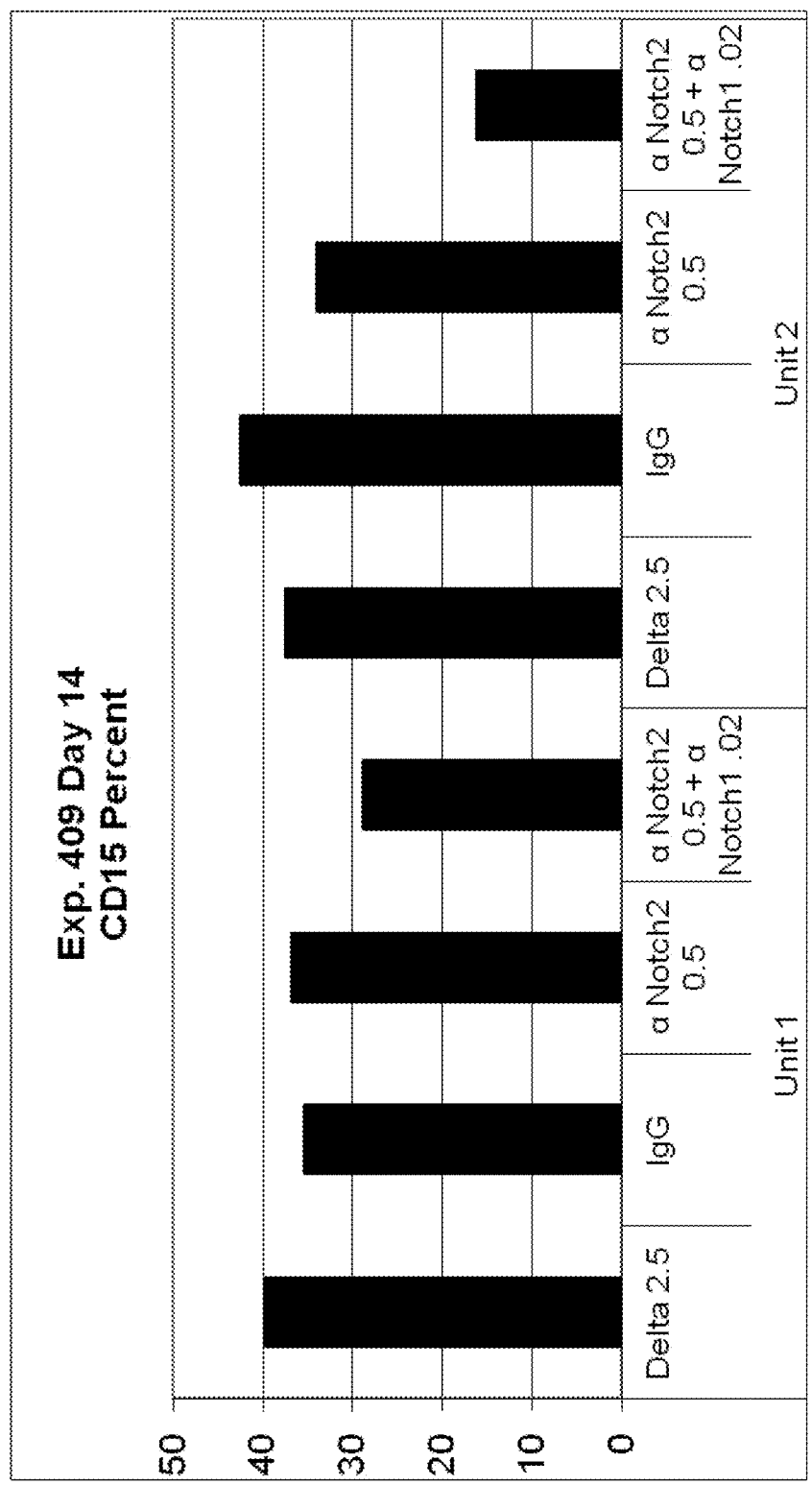
Figure 5D:
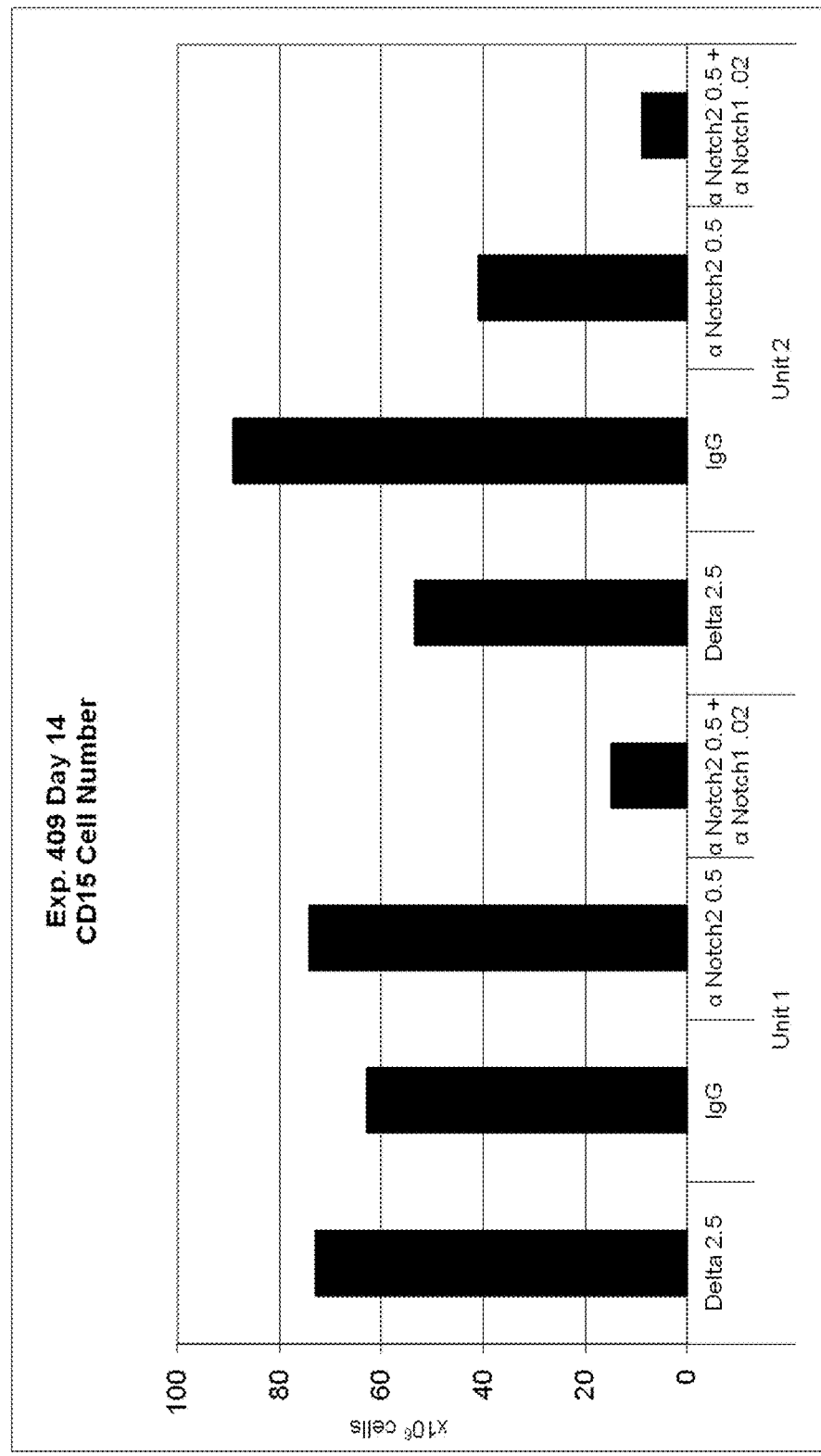

FIG. 3. After culture as in FIG. 2 for 14 days, the expanded progeny of 10,000 cord blood CD34$^+$ cells were transplanted into each of six NSG mice per group. Bone marrow aspirates from mice were analyzed for engraftment by flow cytometry two weeks post-transplant. The combination of Notch 1 antibody (αN1, clone MHN1-519 (commercially available from Biolegend, San Diego, Calif.)) and Notch 2 antibody (αN2, clone MHN2-25, 0.5 µg/ml (commercially available from Biolegend, San Diego, Calif.)) enabled significantly higher levels of human engraftment than Delta, IgG, or Notch 2 antibody alone (p=0.0024 and p=0.0225 respectively, for the two cord blood units), as shown by the percent CD4$^+$ cells (y-axis) in bone marrow aspirates at two weeks. Numbers on x-axis are given in µg/ml.

FIGS. 4A-D. Culture of AGM-derived CD45$^+$/VE-Cadherin$^+$ cells on specific Notch antibodies effects generation of LSK-SLAM cells and multilineage engraftment. (A) Numbers of LSK-SLAM (Sca1+c-kit+CD150+CD48−Gr1− F480−) cells by flow cytometry analysis generated following 5 days of cultures on Delta1$^{ext-IgG}$ (Delta) at 2.5 µg/ml, HuIgG at 2.5 µg/ml and indicated doses of immobilized monoclonal antibodies for Notch 1 antibody (MN1 or antiN1, clone HMN1-12 (commercially available from Biolegend, San Diego, Calif.)) or Notch 2 antibody (MN2 or antiN2, clone HMN2-35 (commercially available from Biolegend, San Diego, Calif.)). Cell numbers are expressed per one AGM equivalent of input starting CD45+/VE-Cadherin+ cells and error bars represent standard deviation of triplicate wells analyzed. (B) Week 2 and (C-D) Week 6 peripheral blood engraftment of cells cultured in panel A, transplanted at 0.5 AGM equivalent of starting cells (CD45.2) per mouse with 3×10$^4$ rescue CD45.1 bone marrow cells. Shown is % donor engraftment (CD45.2), donor myeloid engraftment (Gr1 and/or F480), and donor B lymphoid (CD19)/T lymphoid (CD3) engraftment as percentage of total CD45$^+$ cells in peripheral blood for each mouse analyzed. Numbers on x-axis are given in µg/ml.

FIGS. 5A-D. Cord blood CD34$^+$ cells from two separate units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and (i) immobilized Delta1 (Delta, 2.5 µg/ml), (ii) immobilized anti-human Notch 2 (α Notch2, clone MHN2-25 (commercially available from Biolegend, San Diego, Calif.)) 0.5 µg/ml, (iii) immobilized anti-human Notch 2 0.5 µg/ml combined with immobilized anti-human Notch 1 (α Notch1, clone MHN1-519 (commercially available from Biolegend, San Diego, Calif.)), or (iv) immobilized control IgG. Both the (A) percentage and (B) total number of CD1$^+$ cells was determined, as was the (C) percentage and (D) total number of CD15$^+$ cells. Numbers on x-axis are given in µg/ml.

Figure 6A:
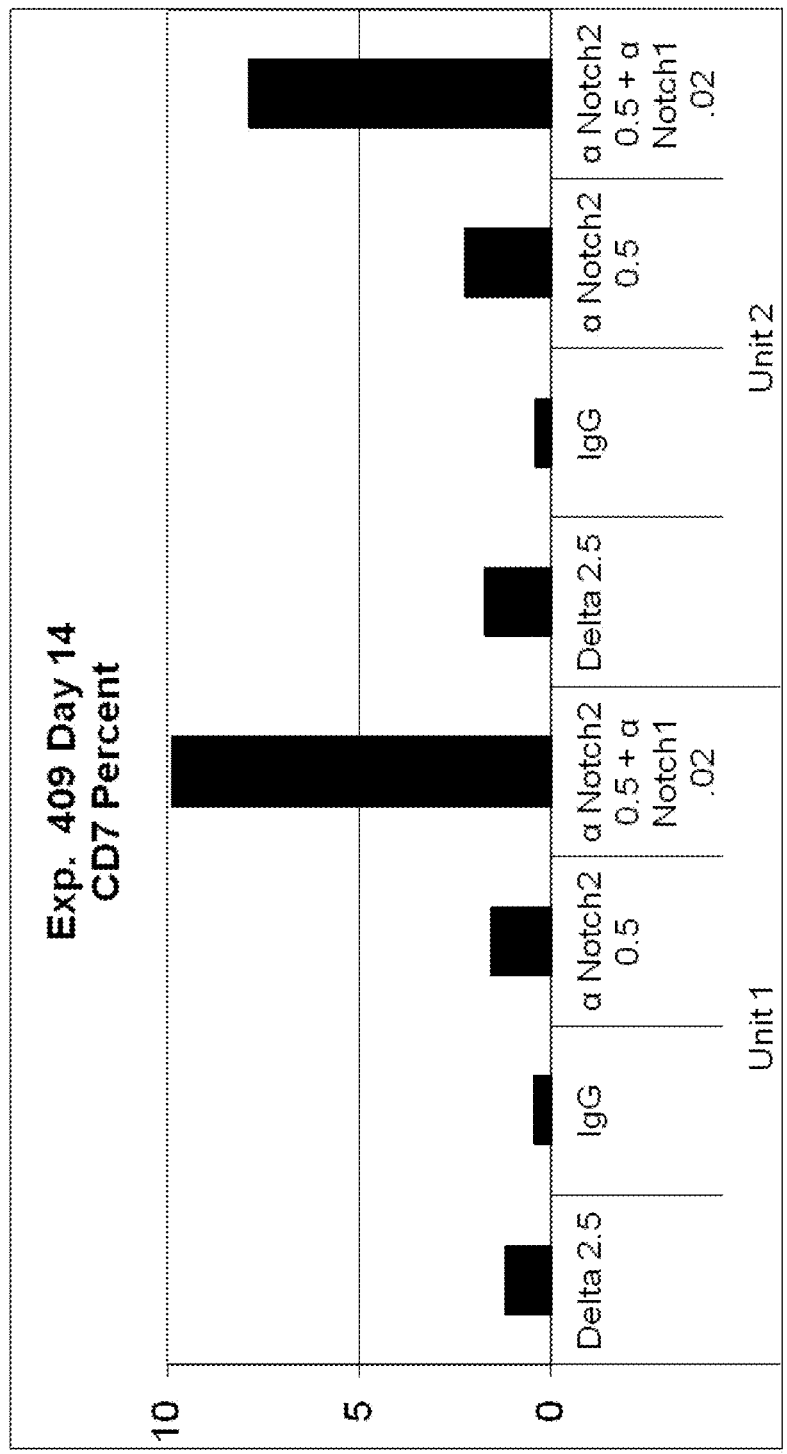
Figure 6B:
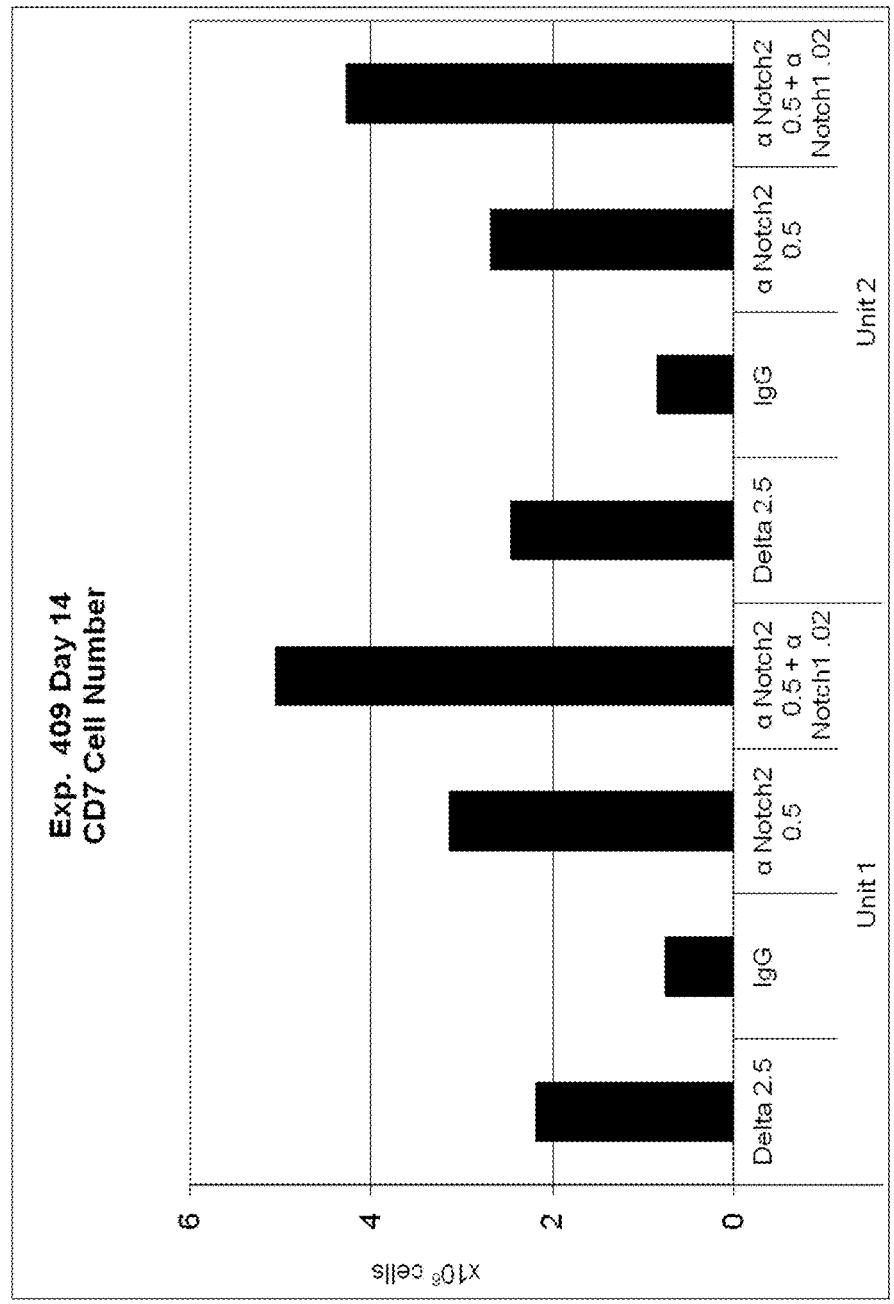

FIGS. 6A-B. Cord blood CD34$^+$ cells from two separate units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and (i) immobilized Delta1 (Delta, 2.5 µg/ml), (ii) immobilized anti-human Notch 2 (α Notch2, clone MHN2-25 (commercially available from Biolegend, San Diego, Calif.)) 0.5 µg/ml, (iii) immobilized anti-human Notch 2 0.5 µg/ml combined with immobilized anti-human Notch 1 (α Notch1, clone MHN1-519 (commercially available from Biolegend, San Diego, Calif.)), or (iv) immobilized control IgG (IgG). Both the (A) percentage and (B) total number of CD7$^+$ cells was determined. Numbers on x-axis are given in µg/ml.

FIGS. 7A-B. Cord blood CD34$^+$ cells from a pool of two units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and (i) immobilized Delta1 (Delta, 2.5 µg/ml), (ii) immobilized anti-human Notch 1 (aN1, clone MHN1-519 (commercially available from Biolegend, San Diego, Calif.)) 0.02 µg/ml, (iii) immobilized anti-human Notch 2 (αN2, clone MHN2-25 (commercially available from Biolegend, San Diego, Calif.)) 0.5 µg/ml combined with immobilized anti-human Notch 1 0.02 µg/ml, or (iv) immobilized control IgG. Expanded progeny of 10,000 cells were transplanted into each of five NSG mice per group. Bone marrow aspirates were analyzed by flow cytometry for total human (CD45), lymphoid (CD19) and myeloid two weeks post transplant and eight or ten weeks post transplant. Shown are (A) results for percentage of CD45$^+$ cells from Exp. 409 at two weeks, also shown in FIG. 3, and (B) results for percentage of CD45$^+$ cells from Exp. 414 at two weeks, for comparison. Numbers on x-axis are given in µg/ml.

FIGS. 8A-B. In two experiments ((A) Exp. 409 and (B) Exp. 414) Cord blood CD34$^+$ cells from a pool of two units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and (i) immobilized Delta1 (Delta, 2.5 µg/ml), (ii) immobilized anti-human Notch 1 (αN1, clone MHN1-519 (commercially available from Biolegend, San Diego, Calif.)), 0.02 µg/ml, (iii) immobilized anti-human Notch 2 (αN2, clone MHN2-25 (commercially available from Biolegend, San Diego, Calif.)) 0.5 µg/ml combined with immobilized anti-human Notch 1 0.02 µg/ml, or (iv) immobilized control IgG (IgG). Bone marrow aspirates were analyzed by flow cytometry for total human (CD45), lymphoid (CD19) and myeloid two weeks post transplant and eight or ten weeks post transplant. Shown are (A) results for percentage of CD45$^+$ cells from Exp. 409 at ten weeks, and (B) results for percentage of CD45$^+$ cells from Exp. 414 at eight weeks. Numbers on x-axis are given in µg/ml.

Figure 9A:
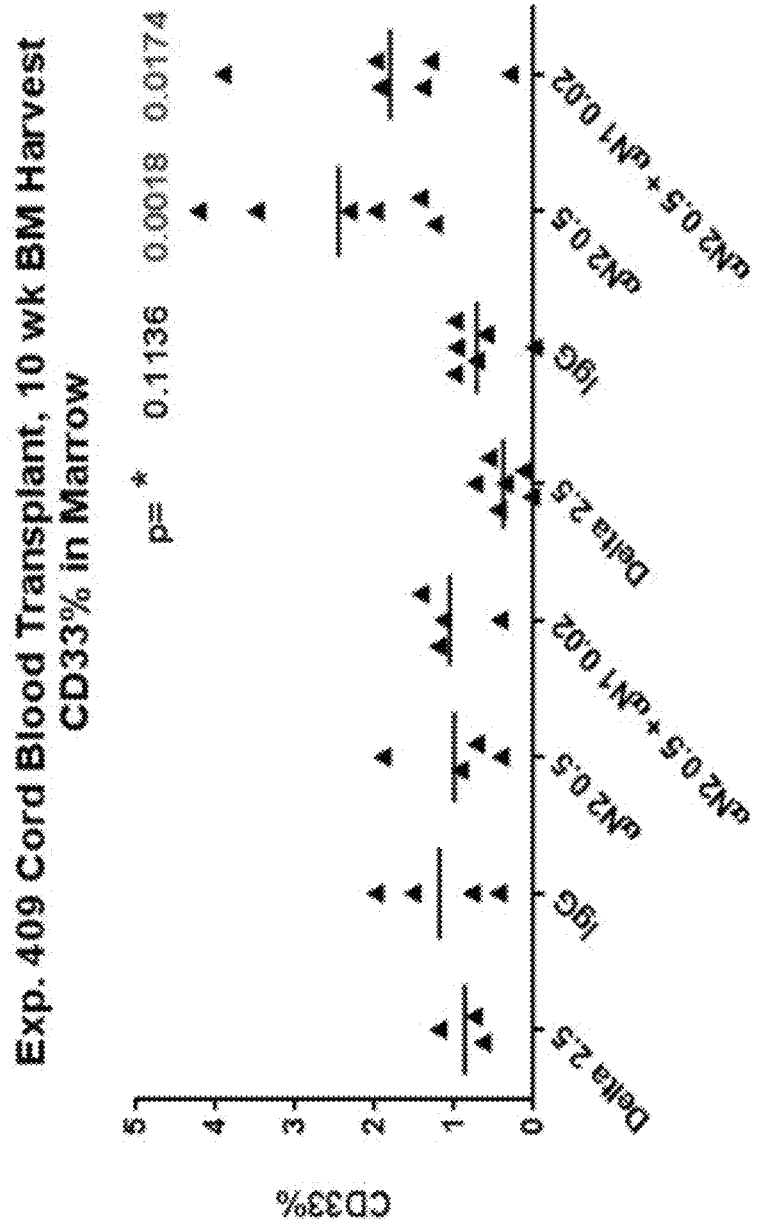
Figure 9B:
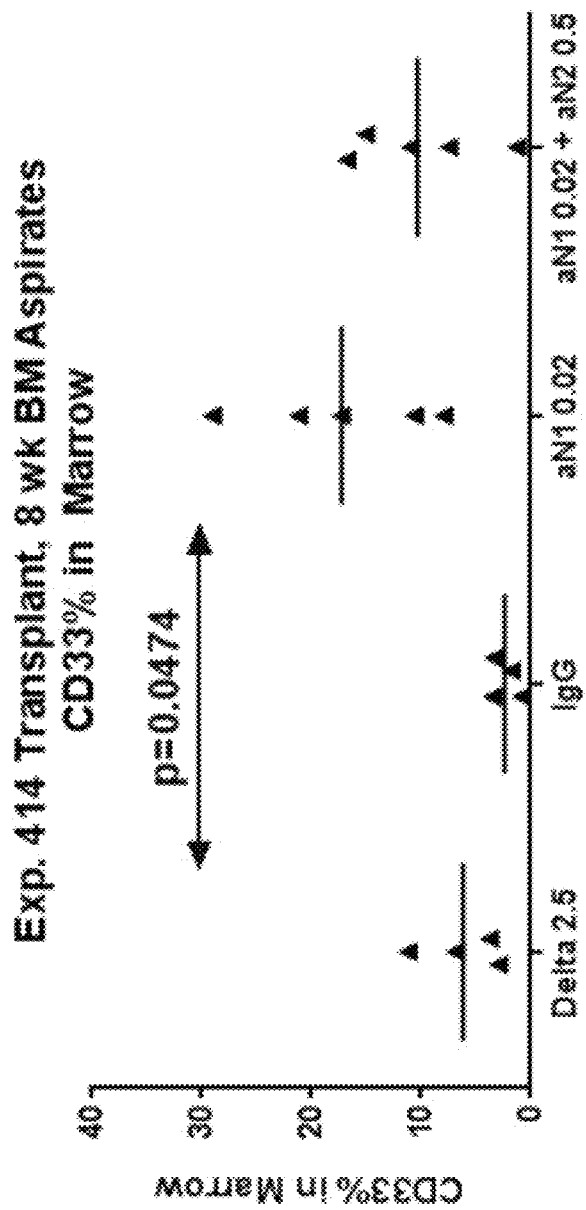
Figure 9C:
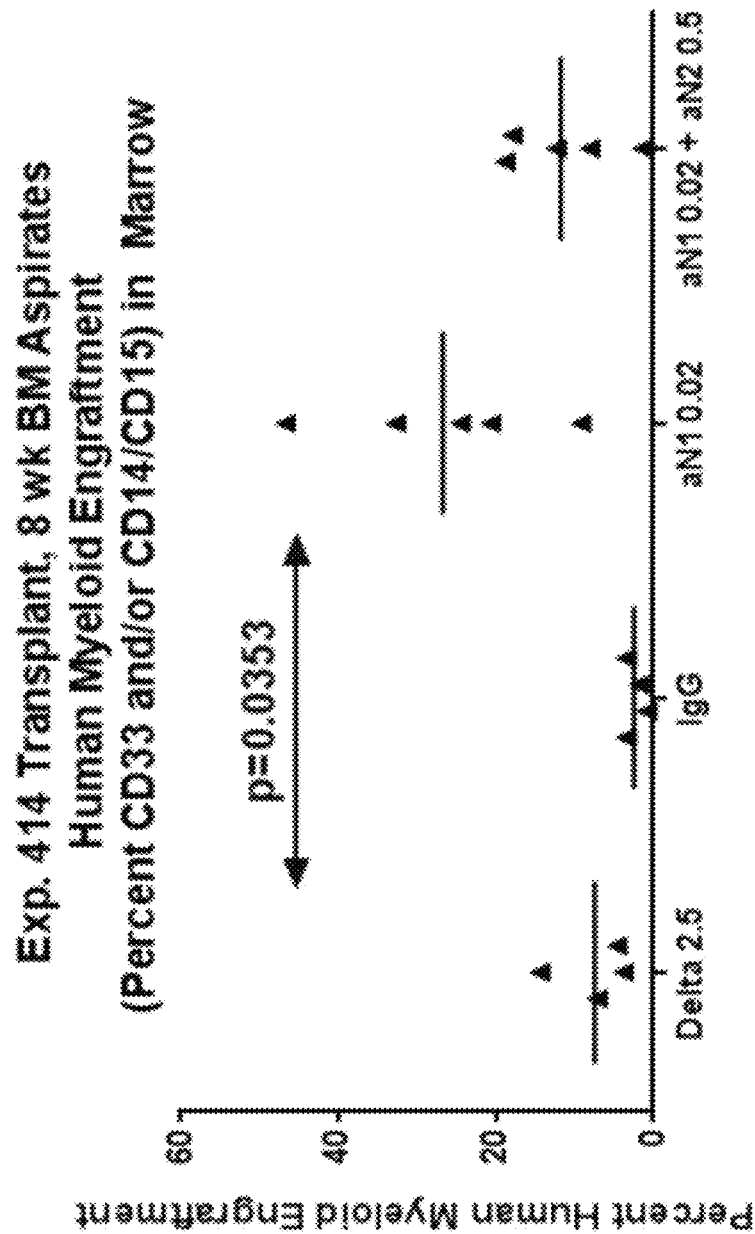

FIGS. 9A-C. Cord blood CD34$^+$ cells from a pool of two units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and (i) immobilized Delta1 (Delta, 2.5 µg/ml), (ii) immobilized anti-human Notch 1 (αN1 or aN1, clone MHN1-519 (commercially available from Biolegend, San Diego, Calif.)) 0.02 µg/ml, (iii) immobilized anti-human Notch 2 (αN2 or aN2, clone MHN2-25 (commercially available from Biolegend, San Diego, Calif.)) 0.5 µg/ml combined with immobilized anti-human Notch 1 0.02 µg/ml, or (iv) immobilized control IgG (IgG). Bone marrow aspirates were analyzed by flow cytometry for total human (CD45), lymphoid (CD19) and myeloid two weeks post transplant and eight or ten weeks post transplant. Shown are (A) results for percentage of CD33$^+$ cells in marrow after ten weeks for Exp. 409, (B) results for percentage of CD33$^+$ cells in marrow after eight weeks for Exp. 414, and (C) results for percentage of CD33$^+$ and/or CD14$^+$/CD15$^+$ cells in marrow after eight weeks for Exp. 414. Numbers on x-axis are given in µg/ml.

Figure 10A:
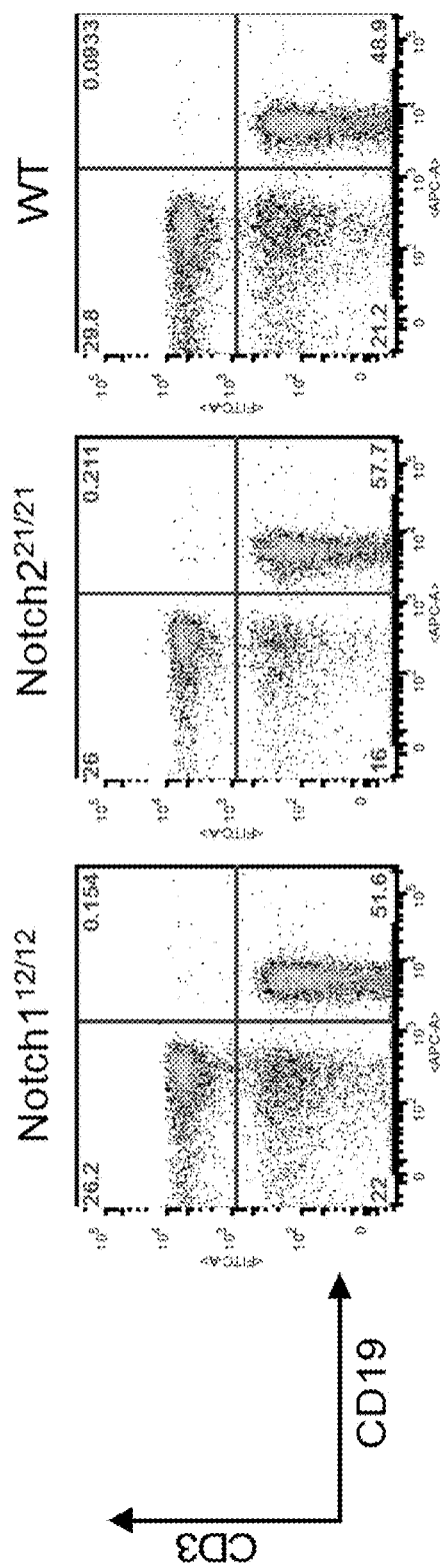
Figure 10B:
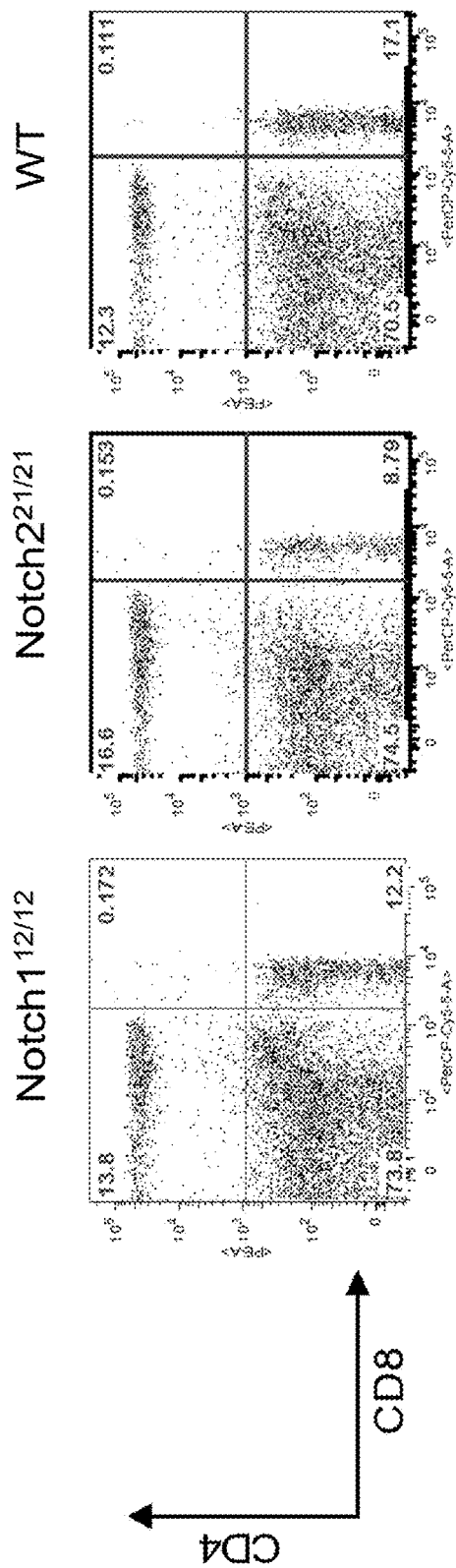
Figure 10C:
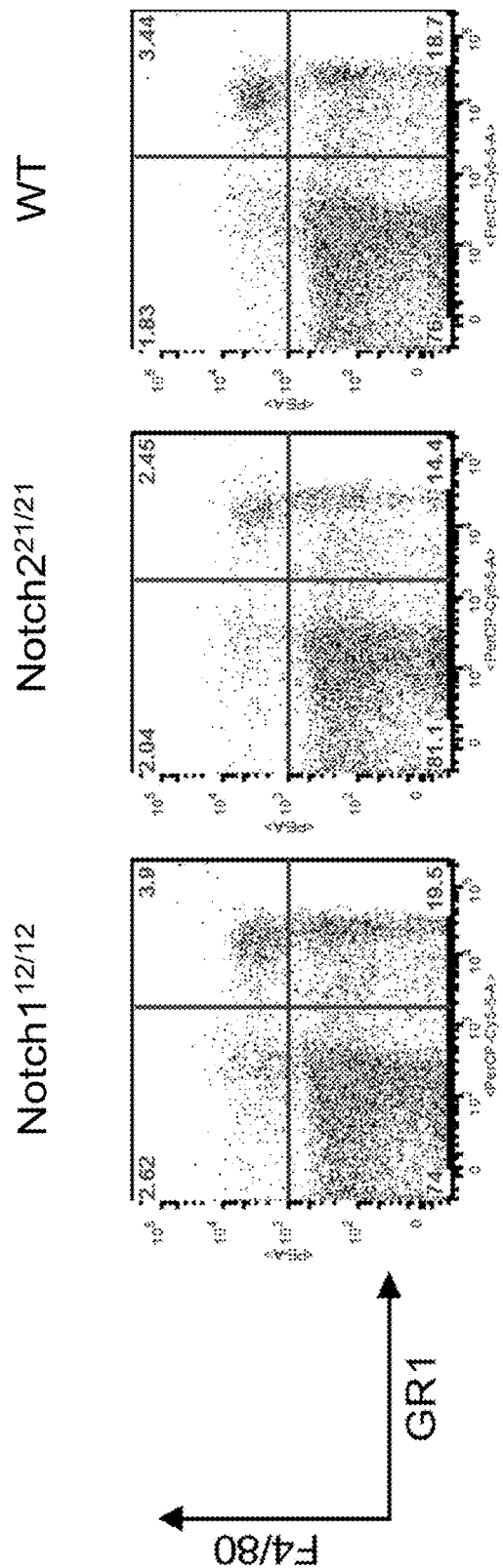

FIGS. 10A-C. Surface marker expression of normal murine peripheral blood (PB) hematopoietic lineages in which the genomic coding region for the entire Notch 2 intracellular domain (ICD) was swapped into the Notch 1 locus (Notch1$^{12/12}$) and the Notch 1 ICD was swapped into the Notch 2 locus (Notch 2$^{21/21}$). Dot plots show PB from designated mice stained with lineage antibodies CD3, CD4, CD8 (T cell), CD19 (B cell), and F4/80, GR1 (myeloid) and FACS analyzed. Results shown are for (A) CD3 and CD19 expression, (B) CD4 and CD8 expression, and (C) F4/80 and GR1 expression. Numbers in corners depict percentage of events within that quadrant.

Figure 11:
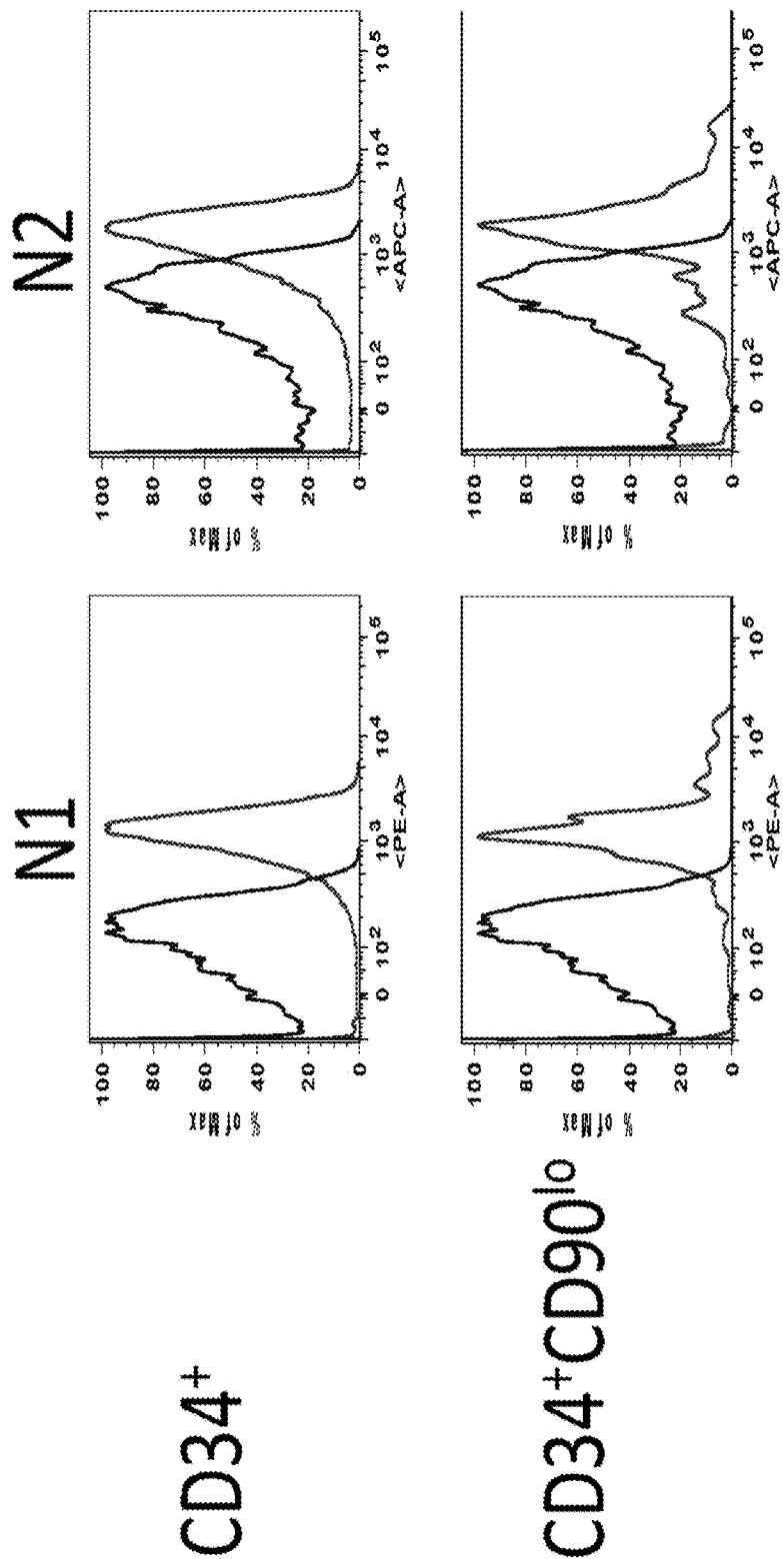

FIG. 11. Freshly isolated cord blood (CB) total CD34$^+$ or CD34$^+$CD90$^{lo}$ primitive subset were analyzed for the cell surface expression of Notch 1 (N1) and Notch 2 (N2). Histograms show relative amounts of Notch 1 or Notch 2 antibody staining (right-most peak in all graphs) compared to isotype control (left-most peak in all graphs).

FIGS. 12A-B. Cord blood CD34$^+$ cells were cultured for 14 days in the presence of immobilized Delta1 (Delta, 2.5 µg/ml) and (A) immobilized Notch 1 antibody (Notch 1, clone MHN1-519 (commercially available from Biolegend, San Diego, Calif.)) 0.02 µg/ml, or (B) immobilized Notch 2 antibody (Notch 2, clone MHN2-25 (commercially available from Biolegend, San Diego, Calif.)) 0.5 µg/ml. Expanded progeny of 10,000 cells were transplanted into each NSG mouse. Bone marrow (BM) aspirates (2-3 weeks) were analyzed for total human cells post-transplant. The y-axis denotes the percentage of CD45 positive cells, indicating the percentage of human cells.

Figure 13:
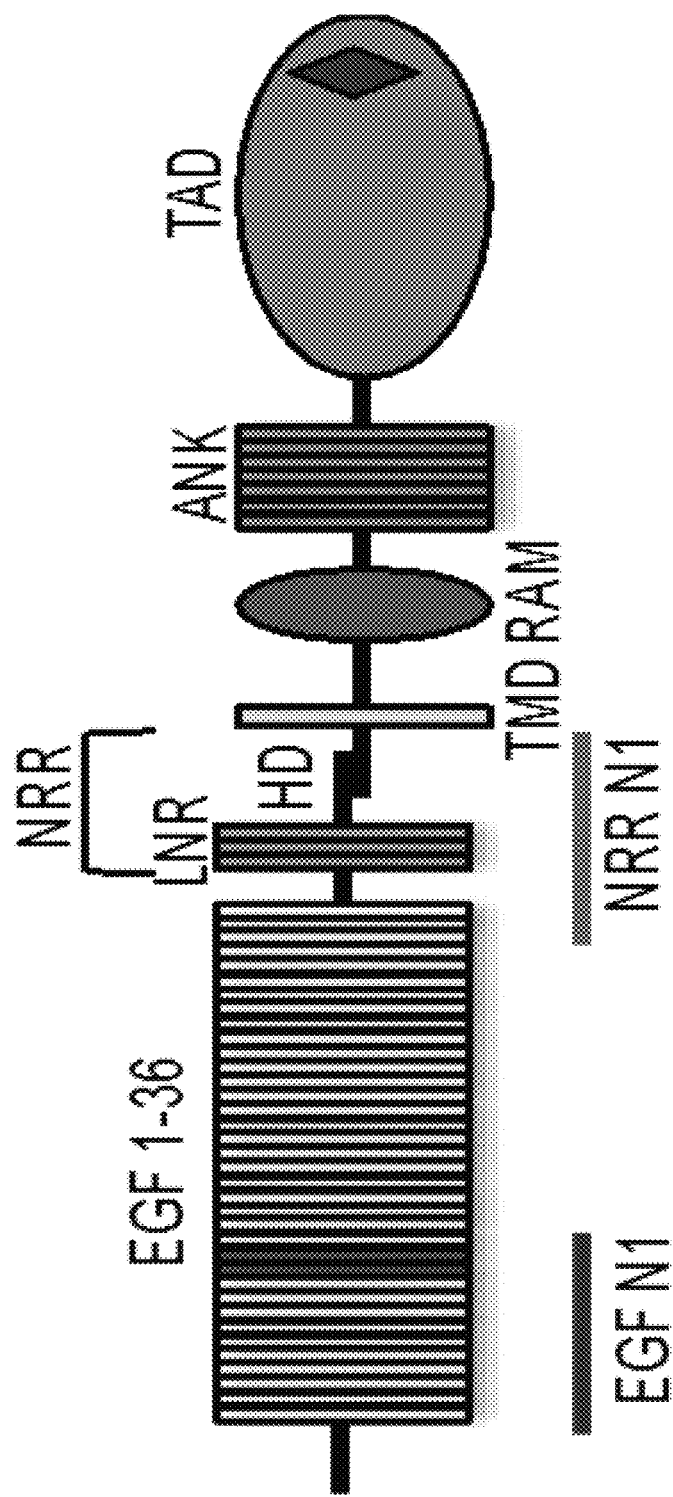

FIG. 13. Schematic representation of human Notch 1. The line labeled EGF-N1 represents the relative position of the peptide used to generate the Notch 1 antibody clone MHN1-519 (commercially available from Biolegend, San Diego, Calif.). The line labeled NRR-N1 represents the relative position of the peptide used to generate the NRR-N1 antibody.

Figure 14:
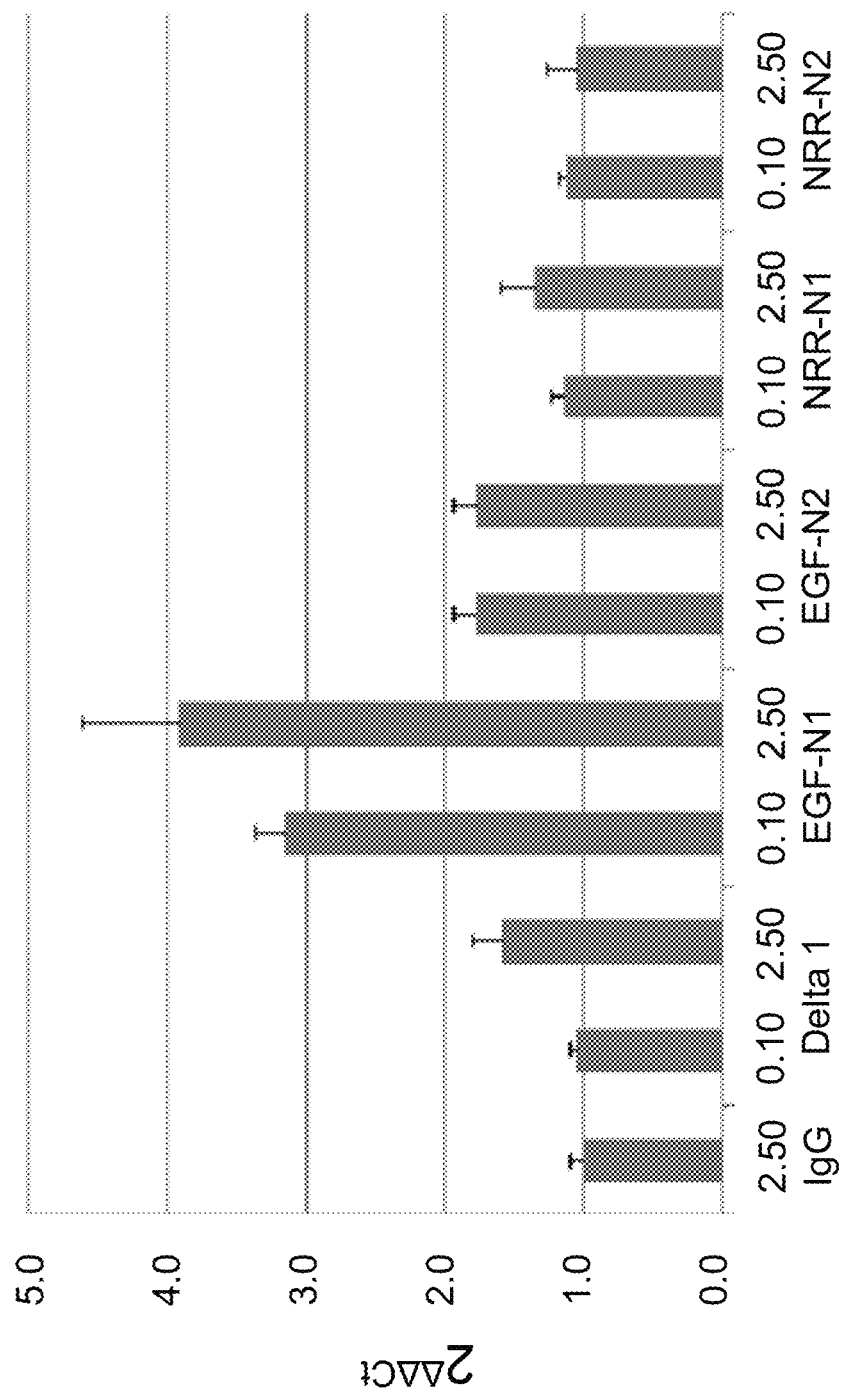

FIG. 14. CB-derived CD34$^+$ cells were incubated for 4 hrs on non-tissue culture wells coated with retronectin and (i) control (IgG), (ii) Delta1 (Delta), (iii) Notch 1 antibody clone MHN1-519 (EGF-N1), (iv) NRR-N1, (v) Notch 2 antibody clone MHN2-25 (EGF-N2), or (vi) NRR-N2 at 0.1 µg/ml or 2.5 µg/ml. cDNA was generated using RNA isolated from harvested cells. Relative expression of Hes1 (y-axis, $2^{\Delta\Delta C_t}$) is reported for each culture condition compared to control IgG. Numbers on x-axis are given in µg/ml.

Figure 15A:
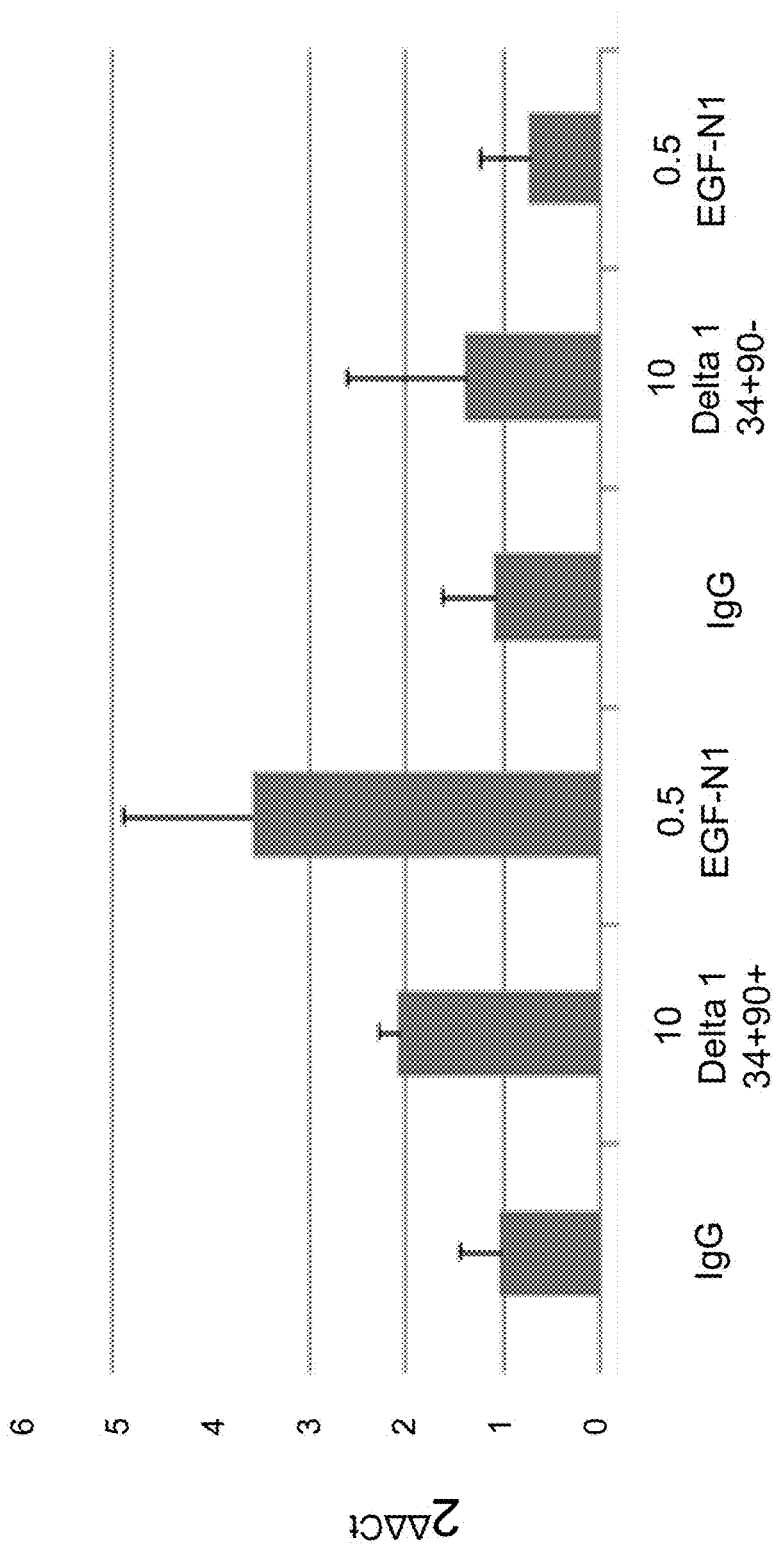
Figure 15B:
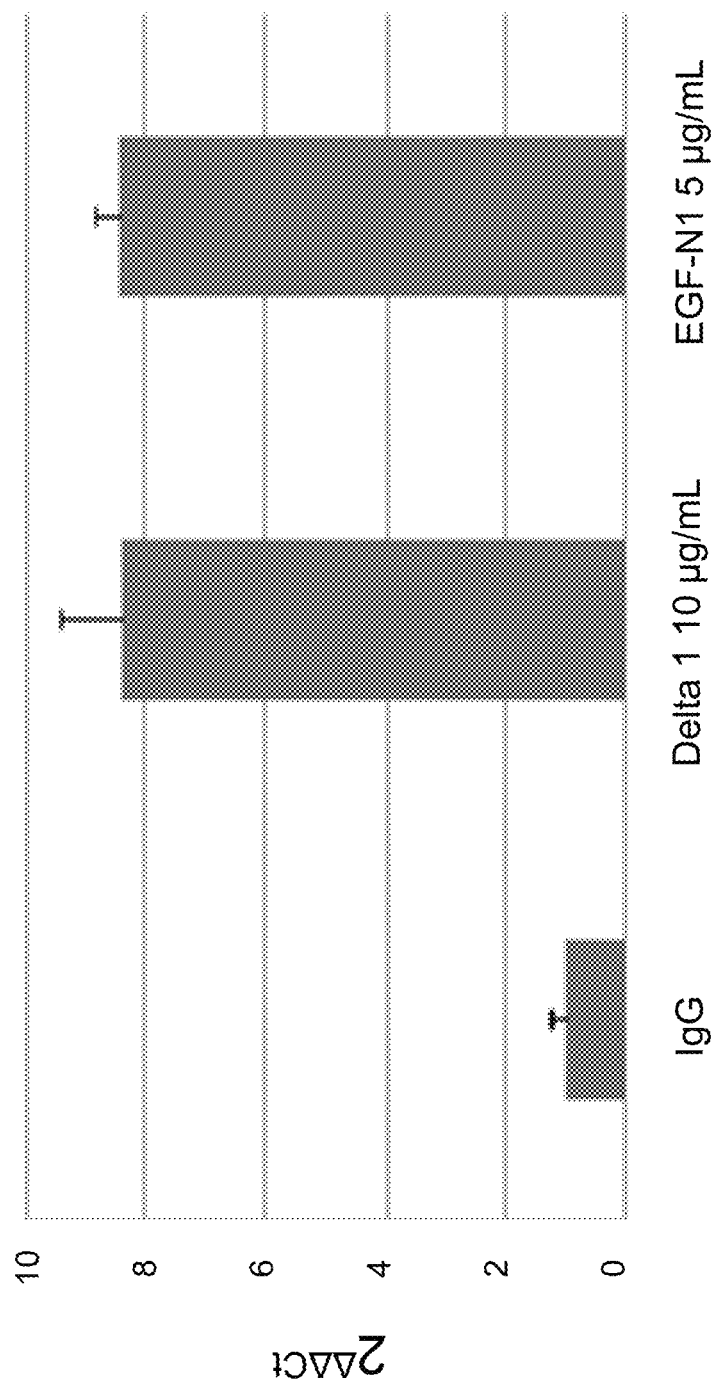

FIGS. 15A-B. (A) Cord blood CD34$^+$ cells were sorted to separate CD34$^+$CD90$^{lo}$ and CD34$^+$CD90$^-$ subsets. Equivalent numbers of cells were transferred to wells coated with retronectin and (i) Human IgG 2.5 µg/ml, (ii) Delta1 10 µg/ml, (iii) Notch 1 antibody clone MHN1-519 (EGF-N1) 0.02 µg/ml, or (iv) Notch 1 antibody clone MHN1-519, 5 µg/ml and incubated for 4 hrs in Stemspan with 5GF (IL-3 10 ng/ml, IL-6, SCF, Flt-3L, TPO all 50 ng/ml). Cells were harvested for Hes1 RT-PCR. Relative expression of Hes1 (y-axis, $2^{\Delta\Delta C_t}$) is reported for each culture condition compared to control IgG. Numbers on x-axis are given in µg/ml. (B) A portion of unsorted cord blood CD34$^+$ cells were cultured in Stemspan with 5GF for 15 days with immobilized Human IgG 2.5 µg/ml and retronectin 5 µg/ml. Cells were transferred to new wells coated with retronectin and (i) Human IgG 10 µg/ml, (ii) Delta1 10 µg/ml, or (iii) Notch 1 antibody clone MHN1-519 (EGF-N1) 5 µg/ml and incubated for 4 hrs. Cells were harvested for Hes1 RT-PCR. Relative expression of Hes1 (y-axis, $2^{\Delta\Delta C_t}$) is reported for each culture condition compared to control IgG.

Figure 16A:
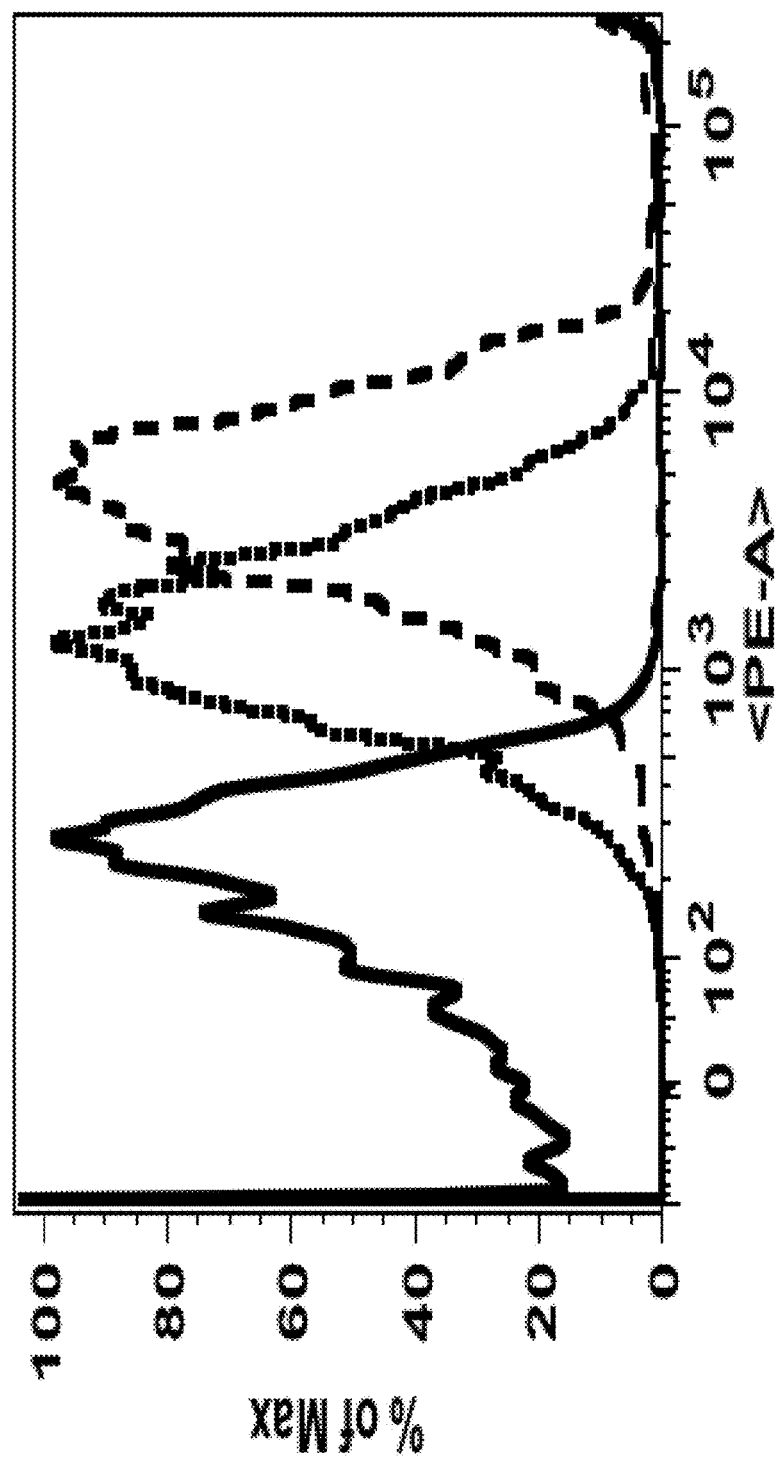
Figure 16B:
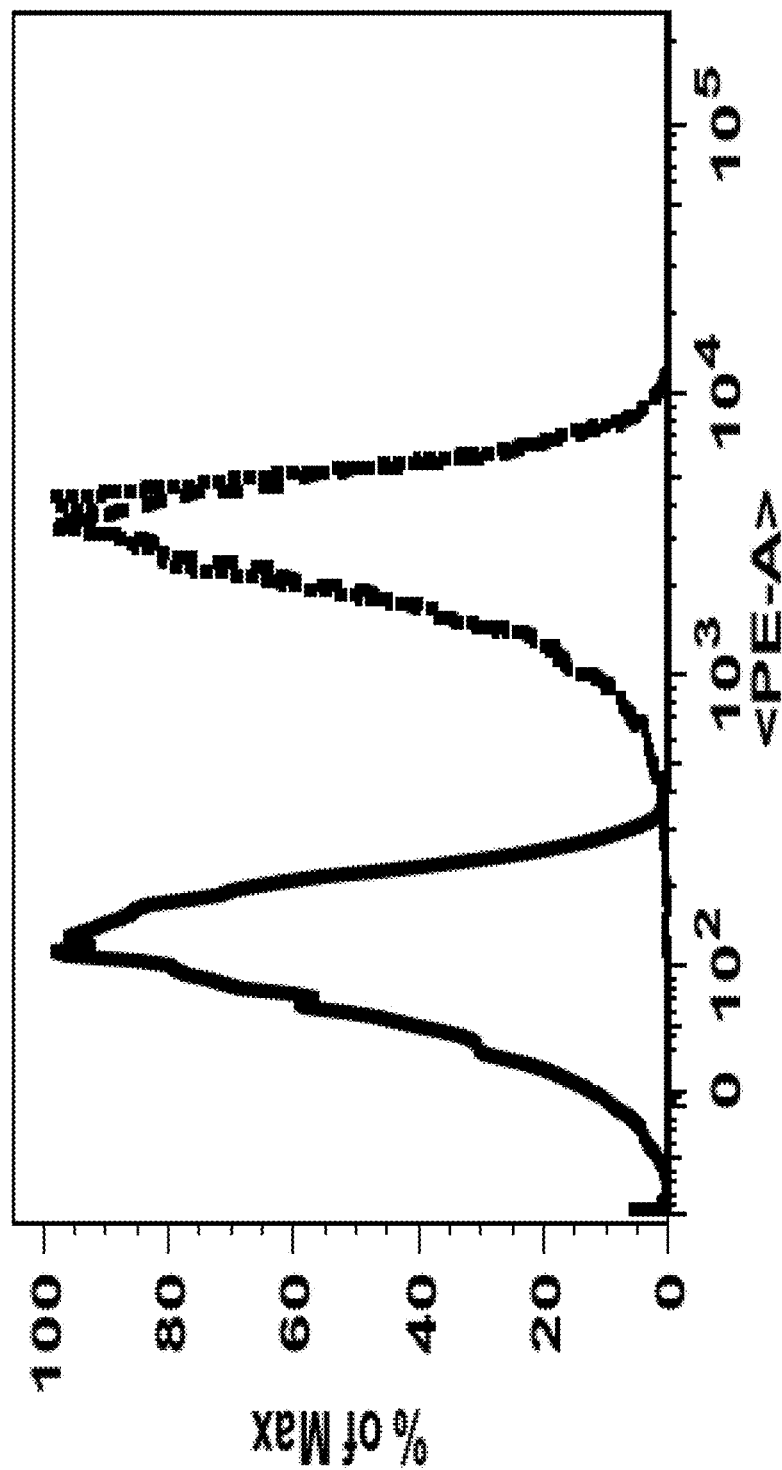
Figure 17A:
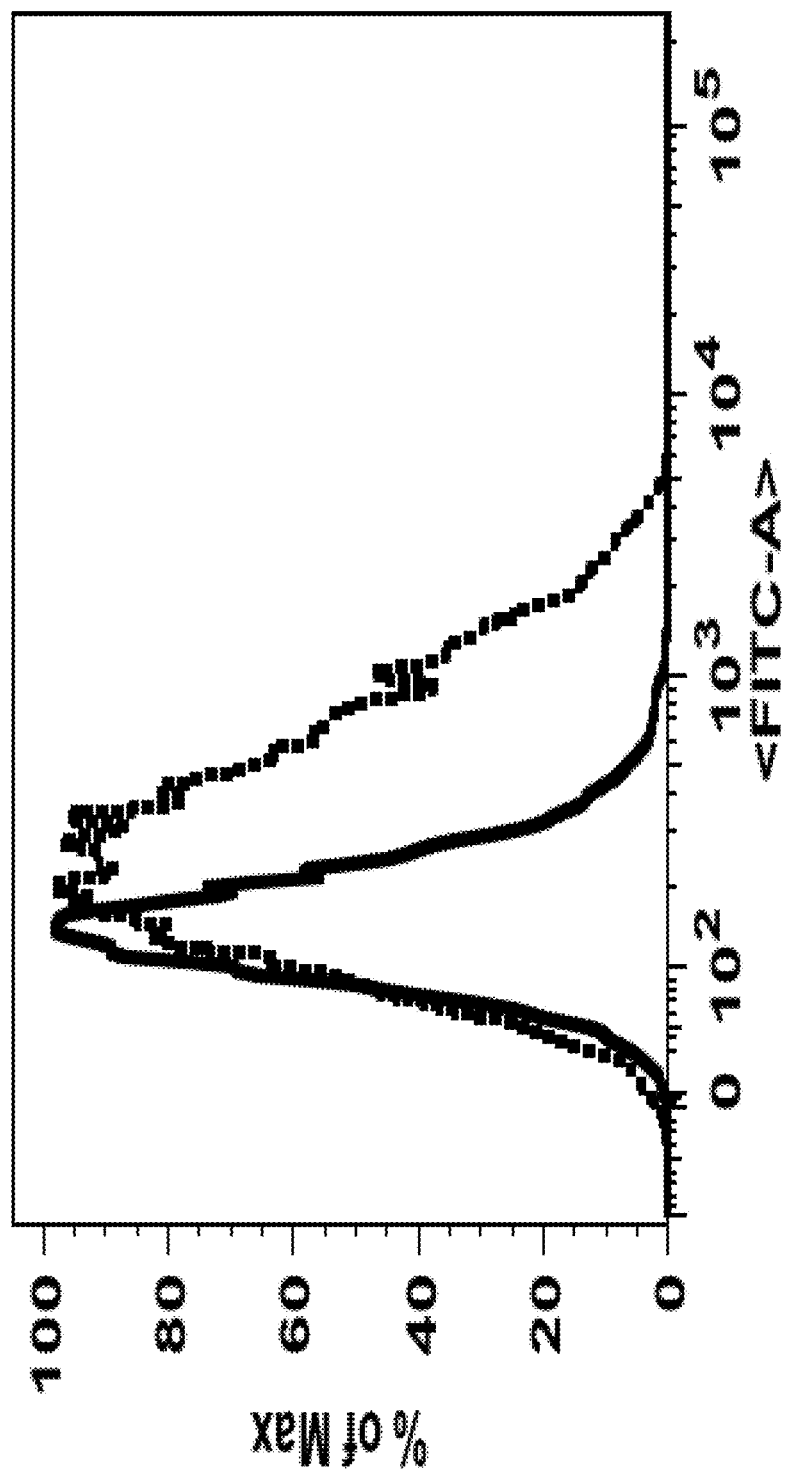
Figure 17B:
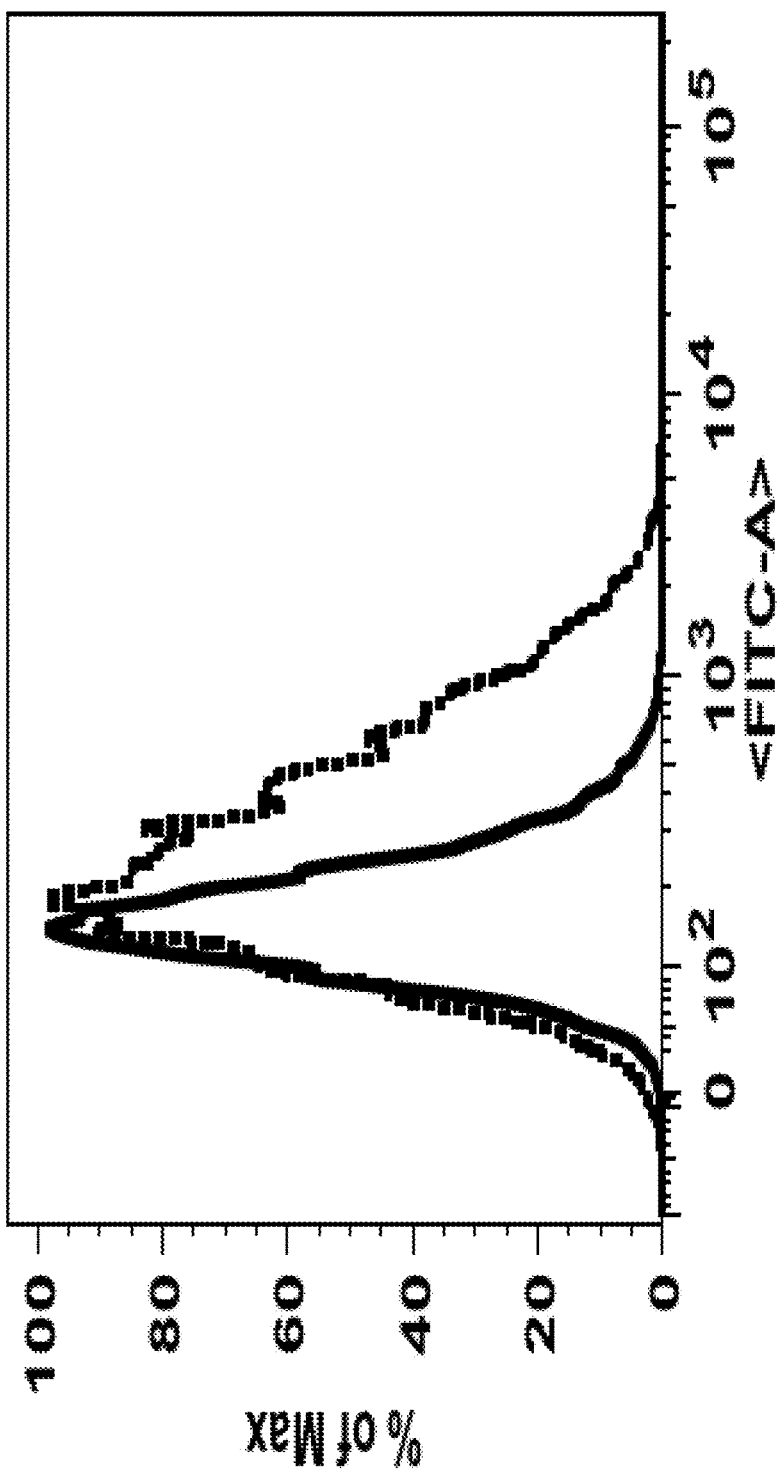
Figure 17C:
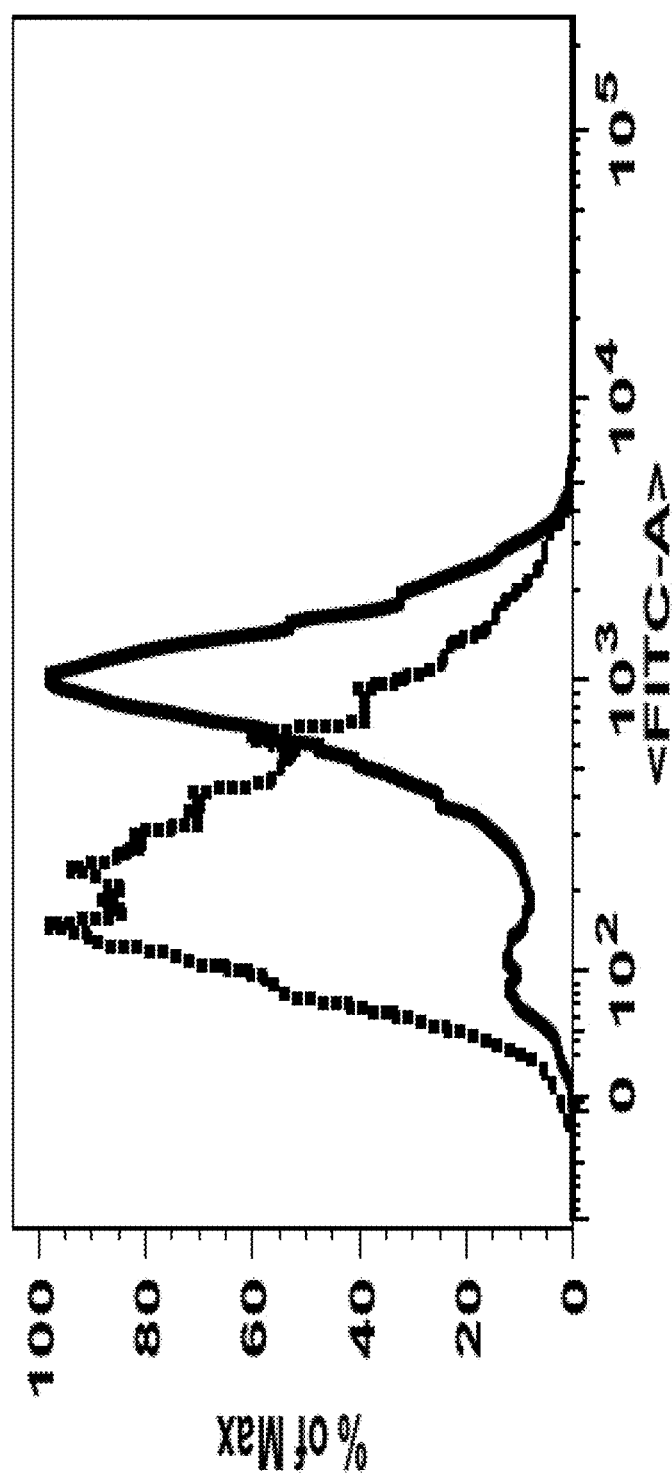
Figure 17D:
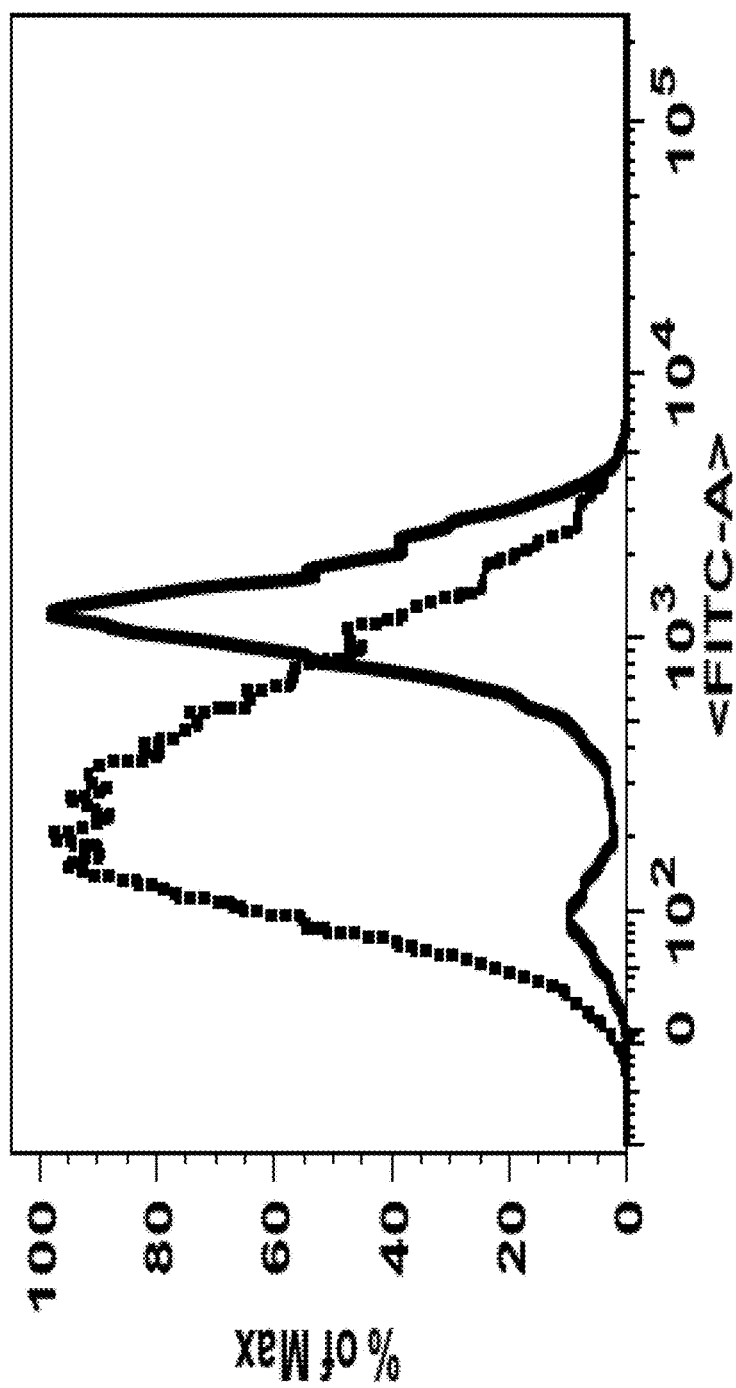
Figure 17E:
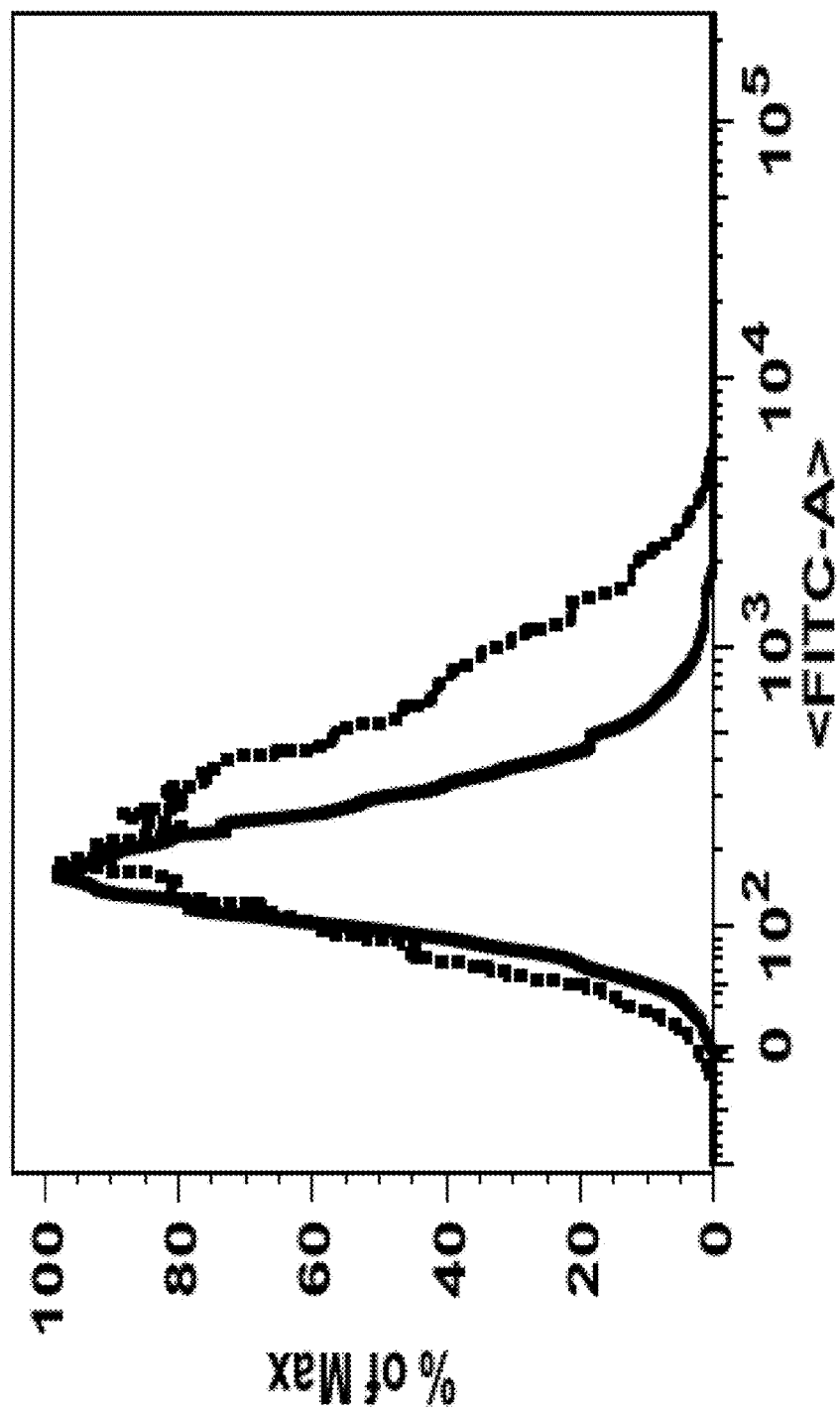
Figure 17F:
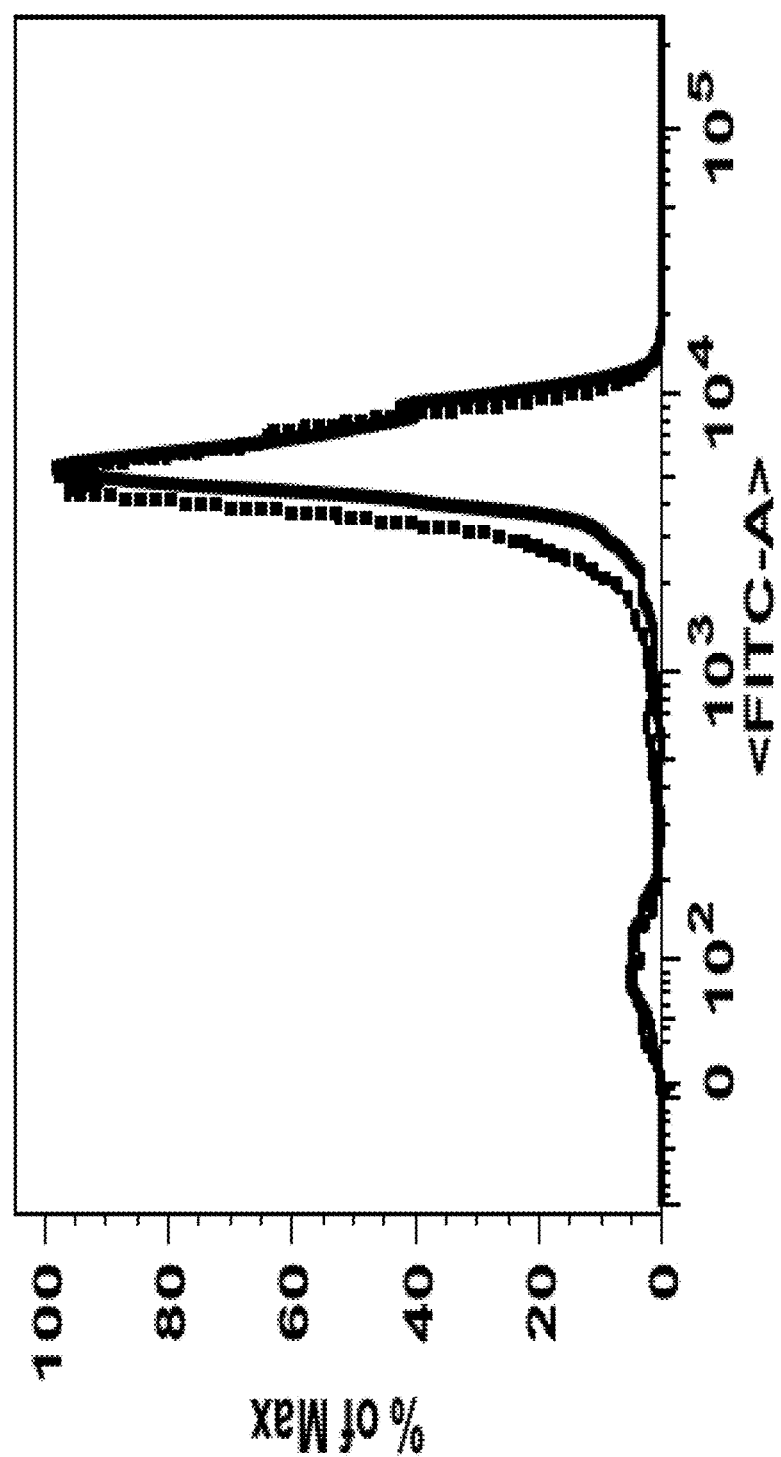

FIGS. 16A-B. Jurkat cells were incubated with (A) Delta1-myc (25 ug/ml) or (B) PE conjugated Notch 1 antibody clone MHN1-519 (EGF-N1) (5 ug/ml) with or without addition of Delta1 fused to Fc portion of human IgG1 (Delta1, small dashed curve, panels A and B; no blocker, large dashed curve, panels A and B). Delta1-myc was detected using the anti-myc antibody 9E10. The control (solid curve, panel A) for Delta 1-myc was binding buffer alone. The control (solid curve, panel B) for MHN1-519 was a non-binding mouse IgG1.

FIGS. 17A-F. CHO K1-DLL1 cells were incubated overnight with (dashed curve) or without (solid curve) Doxycycline, (1 µg/ml) to induce DLL1 and transferred to wells coated with (A) nothing, (B) immobilized human IgG (2.5 µg/ml), (C) immobilized Delta1 2.5 µg/ml, (D) immobilized Delta1 10 µg/ml, (E) immobilized Notch 1 antibody clone MHN1-519 (EGF-N1) 0.02 µg/ml, or (F) immobilized Notch 1 antibody clone MHN1-519 5 µg/ml, all with Retronectin (5 µg/ml). After 2 days, cells were harvested and YFP expression assessed by flow cytometry.

Figure 18:
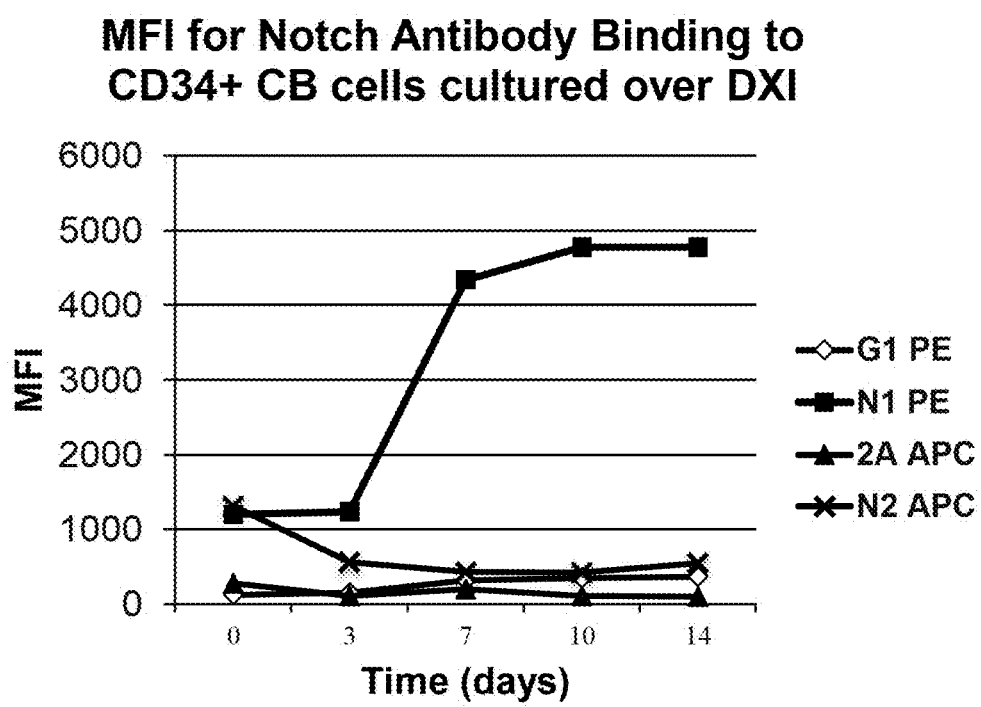

FIG. 18. Human anti-Notch 1 antibody conjugated to PE and human anti-Notch 2 antibody conjugated to APC were used to detect Notch expression on freshly isolated cord blood CD34+ cells as well as those cultured on immobilized Delta1. Mean fluorescence intensity (MFI) was measured at intervals from 0 to 14 days of culture for (i) anti-Notch 1 antibody conjugated to PE (N1, squares), (ii) anti-Notch 2 antibody conjugated to APC (N2, crosses), (iii) control IgG1 (G1, diamonds), or (iv) control IgG2a (2A, triangles).

Figure 19:
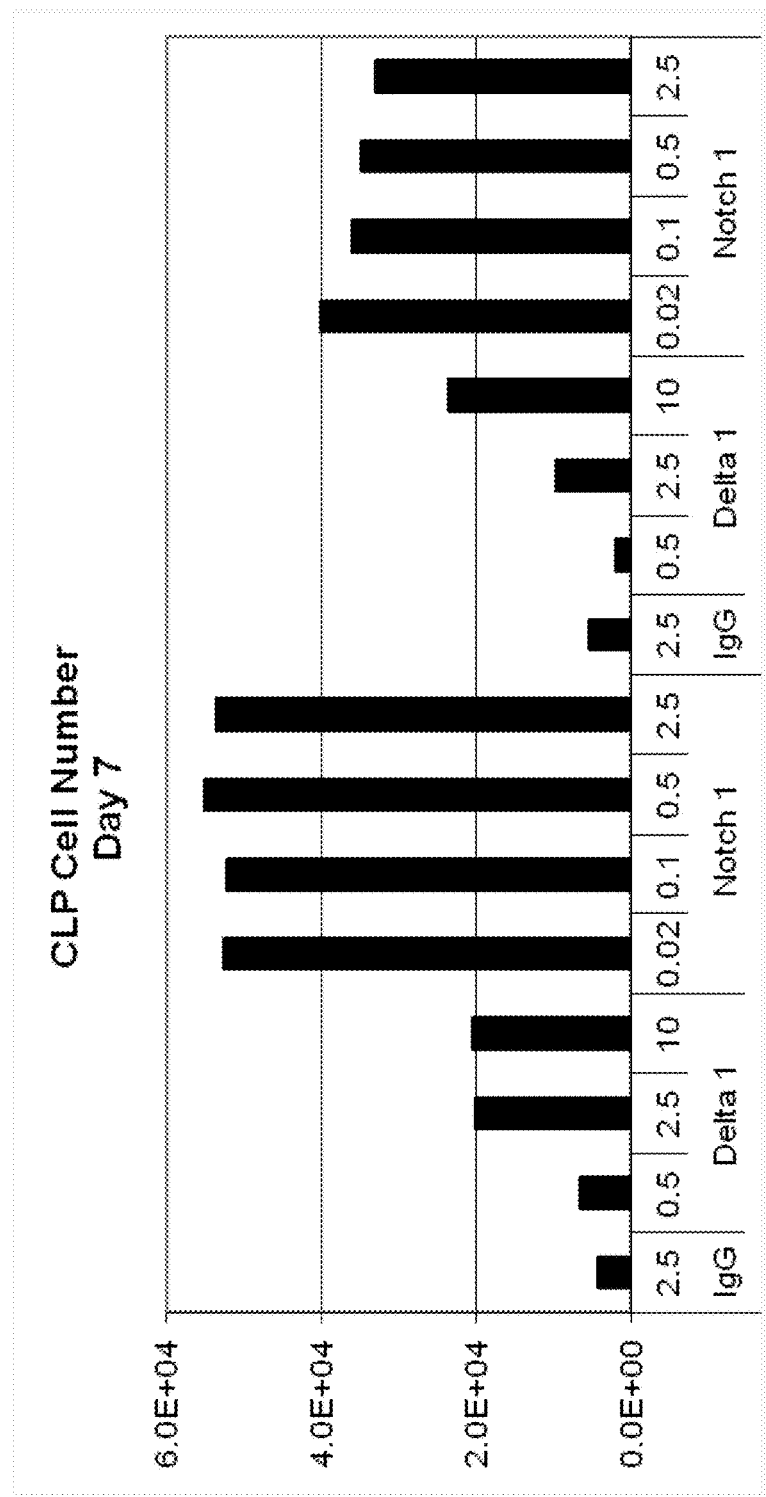

FIG. 19. Cord blood CD34$^+$ cells from two separate units were grown in the presence of immobilized retronectin 5 µg/ml and (i) immobilized control IgG (ii) immobilized Delta1 (0.5, 2.5 or 10 µg/ml), or (iii) immobilized anti-human Notch 1 (Notch 1 (0.02, 0.1, 0.5 or 2.5 µg/ml), clone MHN1-519 (commercially available from Biolegend, San Diego, Calif.)). Common Lymphoid Progenitor cells (CLP), the CD34$^+$/CD38$^-$/CD7$^+$ population, were assessed by flow cytometry. The y-axis indicates the total number of CD34$^+$/CD38$^-$/CD7$^+$ cells at day 7. Numbers on x-axis are given in µg/ml.

Figure 20A:
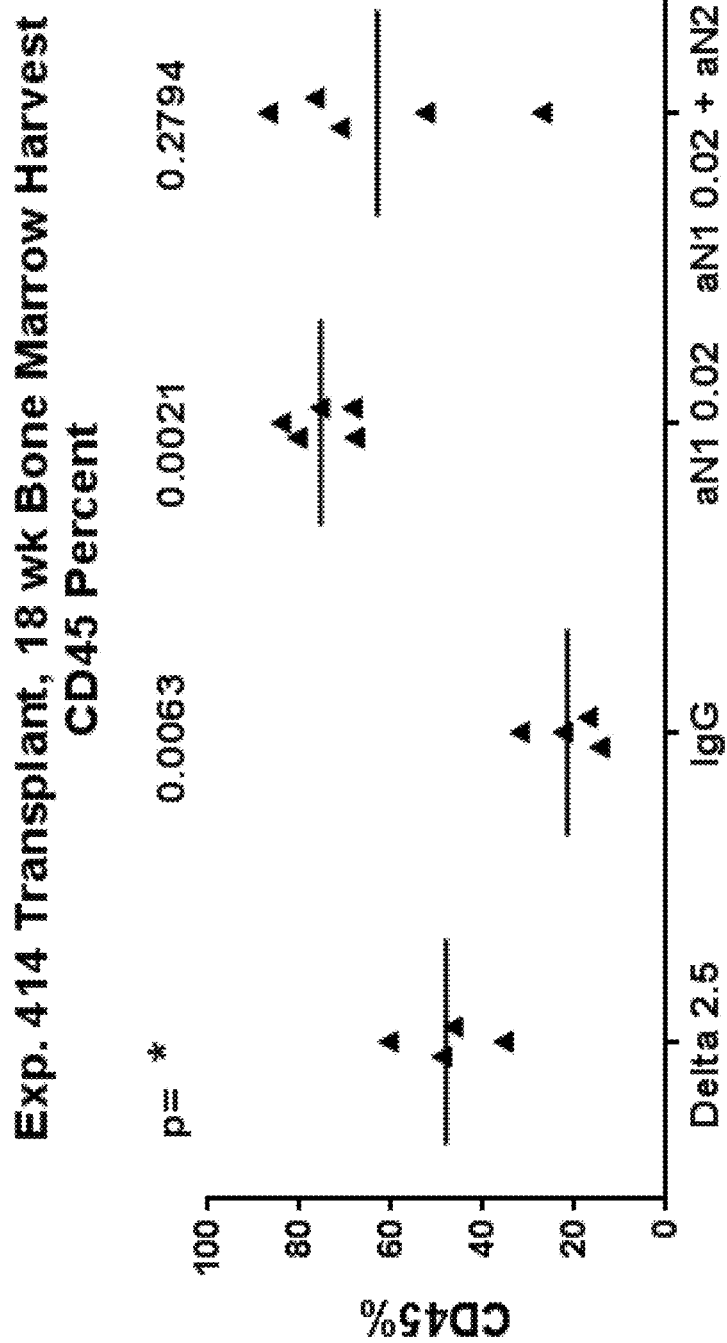
Figure 20B:
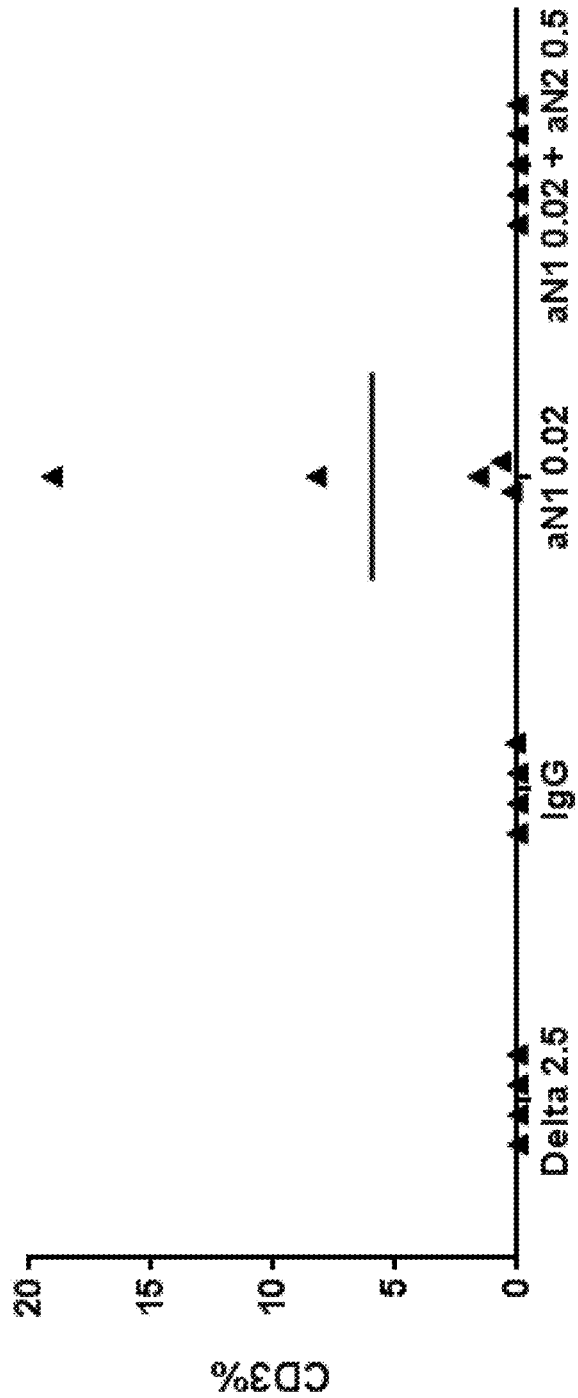

FIGS. 20A-B. Cord blood CD34$^+$ cells from a pool of two units were grown in the presence of immobilized retronectin 5 µg/ml and (i) immobilized Delta1 2.5 µg/ml, (ii) immobilized Control IgG, (iii) immobilized anti-human Notch 1 (αN1, clone MHN1-519 (commercially available from Biolegend, San Diego, Calif.)) 0.02 µg/ml, or (iv) immobilized anti-human Notch 1 0.02 µg/ml combined with anti-human Notch 2 (αN2, clone MHN2-25, (commercially available from Biolegend, San Diego, Calif.)) 0.5 µg/ml. On day 14 of culture, the expanded progeny of 10,000 cells was transplanted into each of five NSG mice per group. After 18 weeks, bone marrows were harvested and (A) total human engraftment (CD45 percent, y-axis) and (B) human T cell engraftment (CD3 percent, y-axis) were assessed by flow cytometry. Numbers on x-axis are given in µg/ml.

5. ABBREVIATIONS AND DEFINITIONS

As used herein, the following abbreviations and definitions will have the meanings indicated:

ATRA: all trans retinoic acid.

BDNF: Brain-derived neurotrophic factor

BFU-E: burst-forming unit-erythroid. An hematopoietic progenitor cell which is capable of producing a colony of erythroid progeny cells in semi-solid medium.

CFU or CFU-C: colony-forming unit or colony-forming unit cell. A cell which is capable of producing a colony of progeny cells in semi-solid medium.

CFU-E/Mega: colony-forming unit-erythrocyte, megakaryocyte. An hematopoietic progenitor cell which is capable of producing a colony composed of erythrocyte and megakaryocyte progeny in semi-solid medium.

CFU-Eo: colony-forming unit-eosinophil. An hematopoietic progenitor cell which is capable of producing a colony composed of eosinophil progeny in semi-solid medium.

CFU-G: colony-forming unit-granulocyte. An hematopoietic progenitor cell which is capable of producing a colony composed of granulocyte (or polymorphonuclear leukocyte) progeny in semi-solid medium.

CFU-GM: colony-forming unit-granulocyte, macrophage. An hematopoietic progenitor cell which is capable of producing a colony composed of granulocyte and macrophage progeny in semi-solid medium.

CFU-M: colony-forming unit-macrophage. An hematopoietic progenitor cell which is capable of producing a colony composed of macrophage progeny in semi-solid medium.

CFU-Mega: colony-forming unit-megakaryocyte. An hematopoietic progenitor cell which is capable of producing a colony composed of megakaryocyte progeny in semi-solid medium.

Megakaryocytes are the precursors of platelets.

CFU-S: colony forming unit-spleen. A multipotential stem cell with self-renewal capacity, which, upon inoculation into lethally-irradiated mice, is capable of producing a colony (nodule) on the spleen(s) containing megakaryocyte, granulocyte and erythroid precursors.

CNTF: Ciliary neurotrophic factor
EGF: Epidermal growth factor
EPO: Erythropoietin
FGF-1: Fibroblast growth factor-1/acidic FGF
FGF-2: Fibroblast growth factor-2/basic FGF
FGF-7: Fibroblast growth factor-7
Flt-3L: flt-3 ligand
GDNF: glial cell line-derived neurotrophic factor
GM-CSF: granulocyte-macrophage colony stimulating factor
HGF: Hepatocyte growth factor
HSC: hematopoietic stem cell. The definition of an HSC is functional and based upon the ability of transplanted cells to repopulate the hematopoietic system of a recipient who has undergone myeloablative treatment. HSCs represent approximately 0.01% of bone marrow cells. They can self-renew and can be assayed by their ability to regenerate the bone marrow and to give rise to long-term lympho- and myelopoiesis (Dexter and Allen, 1992, Nature 360:709-710).
HSPC: hematopoietic stem and progenitor cells
HPP-CFC or HPP-mix: high proliferative potential colony forming cell, which is an immature myeloid stem cell.
ICD: intracellular domain
IGF-1: Insulin-like growth factor-1
IL-3: interleukin-3
IL-6: interleukin-6
IL-7: interleukin-7
IL-11: interleukin-11
IRES: internal ribosomal entry site
Lymphoid stem cell: A lymphoid stem cell has limited self renewal capacity and is capable of regenerating entire lymphoid lineages and of producing a colony composed of all lymphoid cell types in semi-solid medium. Murine lymphoid stem cells are marked by their expression of CD25.
Myeloid stem cell: A myeloid stem cell has limited self renewal capacity and is capable of regenerating entire myeloid lineages and of producing a colony composed of all myeloid cell types in semi-solid medium. Murine myeloid stem cells are identified by the expression of Gr-1 and F4/80.
NGF: Nerve growth factor
NSG mice: NOD-scid IL2Rgamma null mice
PDGF: Platelet-derived growth factor
RAM: RBPJK binding domain of Notch
RAR: retinoic acid receptor
SCF: stem cell factor, also known as the c-kit ligand or mast cell growth factor
TGF-β: transforming growth factor-β
TPO: thrombopoietin

6. DETAILED DESCRIPTION

The present disclosure provides methods for expanding hematopoietic stem cells, comprising culturing the hematopoietic stem cells in the presence of one or more agonists that are (a)(i) a Notch 1 agonist, (ii) a Notch 2 agonist, or (iii) a Notch 1 agonist and a Notch 2 agonist, and (b) one or more growth factors, thereby producing an expanded hematopoietic stem cell population; wherein the Notch 1 agonist is an immobilized antibody, or an immobilized antigen-binding fragment thereof, that binds to Notch 1; and the Notch 2 agonist is an immobilized antibody, or an immobilized antigen-binding fragment thereof, that binds to Notch The methods of the invention for expanding precursor cells are carried out ex vivo.

The present disclosure provides methods for producing immortalized cell populations of non-terminally differentiated cells. Cells immortalized by the methods of the present disclosure are hereinafter referred to as Immortalized cells. In particular, the present disclosure provides methods of growing precursor cells (non-terminally differentiated cells) in culture for a period beyond which the cells would otherwise stop proliferating, differentiate and/or die, due to senescence and/or undergoing crisis leading to cell death. The methods comprise exposing the cell to a Notch 1 agonist, a Notch 2 agonist, and/or a Notch 1 agonist and a Notch 2 agonist. In particular embodiments, cells are also exposed to one or more growth factors that promote proliferation but not differentiation of the precursor cells.

The present disclosure also provides that quantitative differences in Notch signaling account for retardation of myeloid differentiation. Because quantitative rather than qualitative differences in Notch signaling are indicated, activation of either Notch 1 and/or Notch 2 can be used to generate desired levels of Notch signaling. Because Notch 1 and Notch 2 receptor expression occurs independently of each other during culture, different Notch agonists can be chosen based on changing expression levels over time. Additionally, the amounts of Notch 1 agonist, Notch 2 agonist or Notch 1 and Notch 2 agonist can be calibrated based on Notch 1 receptor expression and Notch 2 receptor expression. Accordingly, in these embodiments, Notch signaling can be due to the presence of a Notch 1 agonist, a Notch 2 agonist, or a Notch 1 agonist and a Notch 2 agonist.

As described herein, a low level of Notch signal strength in individual cells (measured, e.g., by submaximal Hes1 expression on an individual cell level) of at least a portion of the hematopoietic stem cell population should be maintained, whether through activation of Notch 1, Notch 2 or Notch 1 and Notch 2. Maintenance of a low Notch signal strength in individual hematopoietic stem cells supports methods for expanding hematopoietic stem cells as described herein whereas induction of higher Notch signal strengths induces cell differentiation toward the lymphoid lineage, such as into Thy1+ and CD25+ T cell precursors. See, for example, Dallas et al., J. Exp. Med., Vol. 201, May, 2005, pp. 1361-1366. Across a hematopoietic stem cell population, inducing both low and high Notch signal strength in different hematopoietic stem cells can be useful, to produce from the population both hematopoietic stem cells and such lymphoid precursors.

The present disclosure further provides methods for producing a desired differentiated cell type from less differentiated types, comprising immortalizing a precursor cell according to the methods of the disclosure and then exposing the Immortalized cell and/or its progeny to conditions that promote differentiation of the precursor cell into the desired cell type. A cell differentiated by the methods of the present disclosure is hereinafter referred to as a Differentiated cell.

These methods can be used to produce cells for repopulation or replenishment of a depleted cell population, for example reconstitution of hematopoietic cells following chemotherapy or T-cells following infection with the Human Immunodeficiency Virus. The cells Immortalized or Differentiated by the methods of the present disclosure can also be made recombinant, for example to deliver a desired gene product.

In certain embodiments of the present disclosure, Immortalized cells are transplanted back into the appropriate region of a subject's body, for example Immortalized HSCs into the subject's bone marrow. In another embodiment, the Immortalized cells are differentiated by activation of the Notch pathway and/or by altering the combination of growth factors in which the cells are grown, according to the methods of the present disclosure or by any method known in the art. In yet another embodiment, the precursor stem cells are concurrently immortalized and differentiated by a combination of Notch 1, Notch 2 or Notch 1 and Notch 2 activation and appropriate growth factors then transplanted back into the subject. Preferably, the Notch 1 and/or Notch 2 agonist is inactivated prior to transplantation into a subject.

The present disclosure further provides cultures and HSCs produced by the methods described herein.

The present disclosure yet further provides kits comprising reagents for immortalizing or immortalizing and differentiating cells, including but not limited to a Notch 1, a Notch 2 agonist and a growth factor which together are capable of immortalizing a precursor cell exposed to them.

6.1 Notch 1 and Notch 2 Agonists

The methods of the present disclosure encompass immortalizing precursor cells (non-terminally differentiated cells) in the presence of a Notch 1 agonist, a Notch 2 agonist or a Notch 1 agonist and a Notch 2 agonist (and, in particular embodiments, one or more growth factors) for a given period of time. A Notch 1 and/or a Notch 2 agonist is an agent that promotes, i.e., causes or increases, activation of Notch pathway function, specific for Notch 1 or Notch 2 as appropriate. As used herein, "Notch pathway function" shall mean a function mediated by the Notch signaling pathway, including but not limited to nuclear translocation of RBP-Jκ or its *Drosophila* homolog Suppressor of Hairless; activation of bHLH genes of the Enhancer of split complex, e.g. Mastermind; inhibition of *Drosophila* neuroblast segregation; and binding of Notch to Delta, Jagged/Serrate, Fringe, Deltex or RBP-Jκ/Suppressor of Hairless, or homologs or analogs thereof.

Notch activation is carried out by exposing a precursor cell to a Notch 1 agonist, a Notch 2 agonist or a Notch 1 agonist and a Notch 2 agonist. The agonist of Notch 1 and agonist of Notch 2 can be but are not limited to soluble molecules, recombinantly expressed as cell-surface molecules, on a cell monolayer to which the precursor cells are exposed, or molecules immobilized on a solid phase. In a preferred embodiment, the Notch 1 agonist and/or the Notch 2 agonist are immobilized Notch 1 and/or Notch 2 antibodies. In another embodiment, the Notch 1 agonist and/or the Notch 2 agonists can be recombinantly expressed from a nucleic acid introduced into the precursor cells.

In some embodiments, cells are expanded by culturing the cells with a Notch 1 agonist immobilized on a first solid phase and a Notch 2 agonist immobilized on a second solid phase, wherein the first and second solid phases are the same.

In some embodiments, cells are expanded by culturing the cells with a Notch 1 agonist immobilized on a first solid phase and a Notch 2 agonist immobilized on a second solid phase, wherein the second solid phase is not the first solid phase. In a specific embodiment, the first and second solid phases are different types of solid phases, selected from among any known in the art, including, but not limited to a culture dish, a culture flask, a culture plate, a bead, a particle, etc. In specific embodiments, the first solid phase is a surface of a tissue culture dish or flask, and the second solid phase is a bead, e.g. a magnetic microbead. In other specific embodiments, the first solid phase is a bead, e.g. a magnetic microbead, and the second solid phase is a surface of a tissue culture dish or flask. In an embodiment where the Notch 1 agonist and Notch 2 agonist are immobilized on different solid phases, the precursor cells can be cultured with the Notch 1 agonist and the Notch 2 agonist concurrently or sequentially.

Notch 1 and Notch 2 agonists of the present disclosure include but are not limited to Notch proteins and analogs and derivatives (including fragments) thereof, proteins that are other elements of the Notch pathway and analogs and derivatives (including fragments) thereof, antibodies thereto and fragments or other derivatives of such antibodies containing the binding region thereof, nucleic acids encoding the proteins and derivatives or analogs; as well as toporythmic proteins and derivatives and analogs thereof which bind to or otherwise interact with Notch proteins or other proteins in the Notch pathway such that Notch 1 or Notch 2 activity is promoted, as described herein. Such agonists include but are not limited to Notch proteins and derivatives thereof comprising the intracellular domain, Notch nucleic acids encoding the foregoing, and proteins comprising the Notch-interacting domain of Notch 1 or Notch 2 receptor ligands (e.g., the extracellular domain of Delta, Jagged, Serrate). Other agonists include but are not limited to RBPJK/Suppressor of Hairless or Deltex. Fringe can be used to enhance Notch activity, for example in conjunction with Delta proteins. These proteins, fragments and derivatives thereof can be recombinantly expressed and isolated or can be chemically synthesized. When the Notch 1 agonist and/or the Notch 2 agonist are expressed in the precursor cell itself, for example a dominant active form of Notch, via a recombinant nucleic acid, identification of cells expressing the Notch 1 agonist and/or the Notch 2 agonist can be facilitated by the introduction of an internal ribosome entry site (IRES) followed by an open reading frame encoding a marker protein 3' to the open reading frame of the Notch 1 agonist and/or the Notch 2 agonist in the recombinant nucleic acid construct. Preferably, a marker protein is a fluorescent protein such as green fluorescent protein (GFP; see e.g., U.S. Pat. Nos. 5,491,084 and 5,777,079); GFP modified to fluoresce at a different intensity and/or wavelength (e.g. blue GFPs, as described by Heim and Tsien, 1996, Curr. Biol. 6:178-82) or the yellow or red-orange emitter recently discovered in reef corals (Matz et al., 1999, Nature Biotechnol. 17:969-973).

In another specific embodiment, the Notch 1 agonist and/or the Notch 2 agonist is a cell which expresses a protein or fragment or derivative thereof, which agonizes Notch 1 and/or Notch 2. The cell expresses the Notch 1 agonist and/or the Notch 2 agonist in such a manner that it is made available to the precursor cells, e.g., secreted, expressed on the cell surface, etc. In yet another specific embodiment, the Notch 1 agonist and/or the Notch 2 agonist is a nucleic acid that encodes a protein or fragment or derivative thereof which agonizes Notch 1 or Notch 2; such an agonist can, for example, be employed or delivered according to the methods described in Section 4.3, infra.

In yet another specific embodiment, the agonist of Notch is a peptidomimetic or peptide analog or organic molecule that binds to a member of the Notch signaling pathway. Such an agonist can be identified by binding assays selected from those known in the art.

In a preferred embodiment the agonist is a protein consisting of at least a fragment of a protein encoded by a Notch-interacting gene which mediates binding to Notch proteins or adhesive fragments thereof. Notch interacting genes, as used herein, shall mean the genes Notch, Delta, Jagged, Serrate, RBPJK, Suppressor of Hairless and Deltex, as well as other members of the Delta/Serrate/Jagged family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g. in *Drosophila*). Adhesive fragments of Notch-binding proteins cited above are described in U.S. Pat. Nos. 5,648,464; 5,849,869; and 5,856,441).

In one embodiment, the Notch 1 agonist and/or the Notch 2 agonist is expressed from a recombinant nucleic acid. For example, expression of truncated, "activated" forms of the Notch receptor lacking the extracellular, ligand binding domain results in gain of function mutant phenotypes. Preferably, the Notch dominant active mutant is expressed by the precursor cells from an inducible promoter, such that expression can be induced for expansion and/or differentiation, with the inducer lacking in vivo in the organism from which the cells are from so that the transplanted cells can respond to their environmental cues. In another embodiment, the nucleic acid encoding the Notch 1 agonist and/or the Notch 2 agonist is flanked by Cre sites. Following expansion and/or differentiation of the precursor cell but prior to transplantation to a subject, the progeny cells comprising the nucleic acid are exposed to Lox protein, as described in Section 4.8 below. Alternatively, the FLP/FRT recombination system can be used to control the presence and expression of a Notch 1 agonist and/or the Notch 2 agonist (Brand and Perrimon, 1993, Development 118:401-415).

Alternatively, in another embodiment the agonist of Notch is not a recombinant dominant Notch active mutant. Alternatively, in another embodiment, exposure of the precursor cells to the Notch 1 agonist and/or the Notch 2 agonist is not done by incubation with other cells recombinantly expressing a the Notch 1 agonist and/or the Notch 2 agonist on the cell surface (although in other embodiments, this method can be used).

In another embodiment, the recombinantly expressed Notch 1 agonist and/or the Notch 2 agonist is a chimeric Notch protein which comprises the intracellular domain of Notch and the extracellular domain of another ligand-binding surface receptor. For example, a chimeric Notch protein comprising the EGF receptor extracellular domain and the Notch intracellular domain is expressed in a precursor cell. However, the Notch pathway will not be active unless the precursor cell expressing the chimera is exposed to the ligand of the EGF receptor, i.e., EGF. As with the inducible promoter controlling the expression of the truncated form of Notch, the activity of the chimeric Notch protein is reversible; when EGF is removed from the cells, Notch activity will cease. Notch activity can again be turned on with the addition of the ligand. Preferably, the chimeric receptor is expressed under the control of an inducible promoter which is turned off, for example by removing the inducer, prior to transplantation of the Immortalized cells, so that the transplanted cells do not respond to EGF in vivo by the activation of the Notch pathway.

In yet other embodiments, Notch 1 and Notch 2 activity can be manipulated by the binding of a Notch 1 agonist or a Notch 2 agonist to the extracellular portion of the Notch 1 or Notch 2 receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate molecules, comprising extracellular domains of the proteins or Notch-binding portions thereof, that have been immobilized on a solid surface, such as a tissue culture plate, can be used as Notch pathway agonists. Such soluble proteins can be immobilized on a solid surface by an antibody or interacting protein, for example an antibody directed to an epitope tag with which Delta or Serrate is expressed as fusion proteins (e.g., a myc epitope tag, which is recognized by the antibody 9E10) or a protein which interacts with an epitope tag with which Delta or Serrate is expressed as fusion proteins (e.g., an immunoglobulin epitope tag, which is bound by Protein A). Soluble truncated Delta or Serrate molecules which lack intracellular domains act as antagonists of the pathway, as their expression results in non-autonomous, dominant negative phenotypes in neighboring Notch-expressing cells.

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins. The peptidomimetic or peptide analog or organic molecule can be identified by the assays described above.

Notch 1 agonists and Notch 2 agonists include antibodies to Notch 1 or Notch 2, as appropriate, and antigen binding fragments thereof. "Antibodies" include, e.g., whole antibodies or single chain Fv fragments (scFv). Antigen-binding fragments of an antibody include, e.g., Fv, Fab, Fab', F(ab')$_2$, Fc, or any biologically effective fragments of an immunoglobulin that bind specifically to an extracellular domain of Notch 1 or Notch 2. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies. In certain embodiments, the Notch 1 agonist is an antibody or antigen binding fragment thereof that binds to the extracellular domain of Notch 1. In specific embodiments, the Notch 1 agonist is an antibody or antigen binding fragment thereof that binds to the extracellular EGF repeat domain of Notch 1. In more specific embodiments, the Notch 1 agonist is an antibody or antigen binding fragment thereof that binds to EGF repeats 1-6 of Notch 1. In certain embodiments, the Notch 2 agonist is an antibody or antigen binding fragment thereof that binds to the extracellular domain of Notch 2. In specific embodiments, the Notch 2 agonist is an antibody or antigen binding fragment thereof that binds to the extracellular EGF repeat domain of Notch 2. In specific embodiments, the Notch 1 agonist is the anti-Notch-1 MHN1-519 antibody (commercially available from Biolegend, San Diego, Calif.). In specific embodiments, the Notch 2 agonist is the anti- Notch-2 MHN2-25 antibody (commercially available from Biolegend, San Diego, Calif.).

As shown in the Examples, hereinafter, antibodies to Notch 1 can overcome Notch cis inhibition to provide Notch signaling pathway activation (Example 4), and antibodies to Notch 1 and antibodies to Notch 2 provide greater expansion of hematopoietic stem cells than achieved with the Notch ligand Delta (Example 3).

While not intending to be bound by any mechanism, antibodies that bind to Notch 1 or Notch 2 are believed to be useful across a range of concentrations to expand hematopoietic stem cells in a hematopoietic stem cell population, because, within the hematopoietic stem cell population, it is believed that some individual hematopoietic stem cells will be cis-inhibited, and some will not be cis-inhibited. It is believed that at relatively high levels of anti-Notch 1 or anti-Notch 2 antibody concentrations, hematopoietic stem cells that would be otherwise cis-inhibited are activated to achieve a low to intermediate level of Notch signaling pathway activation in such cells, and thus to expand to produce more hematopoietic stem cells, whereas non-cis-inhibited hematopoietic stem cells are activated to achieve a high level of Notch signaling pathway activation in such cells, to produce early T cell precursors able to migrate to the thymus and generate mature T cells. It is believed that at relatively low levels of anti-Notch 1 or anti-Notch 2 antibody concentrations, hematopoietic stem cells that are not cis-inhibited are activated to achieve a low to moderate level of Notch signaling pathway activation in such cells, and thus to expand to produce more hematopoietic stem cells. In some instances, the expansion of hematopoietic stem cells (i.e., the production from a population of hematopoietic stem cells of more hematopoietic stem cells), as well as the production of early T cell precursors able to migrate to the thymus and generate mature T cells, is desirable and is provided by the invention.

Antibodies that specifically bind an extracellular domain of Notch 1 or Notch 2 can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to an extracellular domain of Notch 1 or Notch 2. For example, binding domains may be identified by screening a Fab phage library for Fab fragments that specifically bind to an extracellular domain of Notch 1 or Notch 2 (see Hoet et al., Nat. Biotechnol. 23:344, 2005). Phage display libraries of human antibodies are also available. Additionally, traditional strategies for hybridoma development using a target of interest as an immunogen in convenient systems (e.g., mice, HuMAb Mouse®, TC Mouse™, KM-Mouse®, llamas, chicken, rats, hamsters, rabbits, etc.) can be used to develop binding domains. In particular embodiments, antibodies specifically bind to Notch 1 or Notch 2 extracellular domains and do not cross react with nonspecific components or unrelated targets. Once identified, the amino acid sequence or polynucleotide sequence coding for the antibody can be isolated and/or determined.

Finally, U.S. Pat. No. 5,780,300 further discloses classes of Notch agonist molecules (and methods of their identification) which can be used to activate the Notch pathway in the practice of the present disclosure, for example molecules that trigger the dissociation of the Notch ankyrin repeats with RBP-Jκ, thereby promoting the translocation of RBP-Jκ from the cytoplasm to the nucleus.

In certain embodiments, to determine whether a Notch binding protein, e.g., an antibody that binds Notch 1 or Notch 2, is a Notch agonist, precursor cells, e.g., hematopoietic stem cells or hematopoietic progenitor cells, are cultured in the presence of the Notch binding protein and then tested for increased Hes1 expression levels (relative to precursor cells cultured in the presence of a control molecule not having Notch agonist activity), e.g., by q-PCR, wherein increased Hes1 expression levels in the cells cultured in the presence of the Notch binding protein indicates that the Notch binding protein is a Notch agonist. In other embodiments, to determine whether a Notch binding protein, e.g., an antibody that binds Notch 1 or Notch 2, is a Notch agonist, precursor cells, e.g., hematopoietic stem cells or hematopoietic progenitor cells, are cultured in the presence of the Notch binding protein and then injected into NSG mice, wherein increased engraftment of the cells cultured in the presence of the Notch binding protein in NSG mice (relative to precursor cells cultured in the presence of a control molecule not having Notch agonist activity) indicates that the Notch binding protein is a Notch agonist.

In preferred embodiments, anti-Notch 1 antibodies provided herein bind to human Notch 1. In preferred embodiments, anti-Notch 2 antibodies provided herein bind to human Notch 2. The amino acid sequence of human Notch 1 is available, for example, as GenBank accession number P46531 or GenBank accession number NP_060087. The amino acid sequence of human Notch 2 is available, for example, as GenBank accession number Q04721 or GenBank accession number NP_077719.

6.2 Growth Factors

The present disclosure provides methods that include immortalizing and optionally differentiating precursor cells by activating the Notch pathway in the presence of selected growth factors. Wherein immortalization but not differentiation is to be achieved, the precursor cells of the disclosure are cultured in the presence of growth factors that support growth but not differentiation. The growth factor can be any type of molecule, such as a protein or a chemical compound that promotes cellular proliferation and/or survival without substantially causing differentiation.

Generally, the present disclosure provides methods of growing precursor cells (non-terminally differentiated cells) in culture for a period beyond which the cells would otherwise stop proliferating, differentiate and/or die by exposing the cell to a Notch 1 agonist, a Notch 2 agonist or a Notch 1 agonist and a Notch 2 agonist (and, in particular embodiments, one or more growth factors) that promotes proliferation but not differentiation of the precursor cells. Exposing the cells to one or more growth factors can initially be done prior to, concurrently with, or following exposure of the cells to a Notch 1 agonist, a Notch 2 agonist or a Notch 1 agonist and a Notch 2 agonist. The precursor cells are concurrently exposed to the growth factor(s) and Notch 1 agonist, Notch 2 agonist or Notch 1 agonist and Notch 2 agonist for at least a portion of the minimal culture time, most preferably the majority of this time. The minimal culture time is the amount of time at which the cell would die or stop proliferating in the absence of Notch 1 agonist, Notch 2 agonist or Notch 1 agonist and Notch 2 agonist and the selected growth factor(s). In one embodiment, the time period is at least the time period for at least 20 cell division cycles, in another embodiment the time period is at least the time period for 100 cell division cycles. In other embodiments, the time period is at least the time period for 25, 30, 40, 50, 60, 70, 80, or 90 cell division cycles. In yet other embodiments, the time period is at least the time period for 125, 150, 175 or 200 cell division cycles. The amount of time will vary according to cell type and is known to those of skill in the art. For hematopoietic cells, for example, the minimal culture time can be 3-4 weeks. In other embodiments, the culture time for hematopoietic cells is 5, 6, 7, 8, 9, or 10 weeks. In yet other embodiments, the culture time for hematopoietic cells is greater than 10 weeks, for example, 12, 15, 18, 20 or 25 weeks.

In specific exemplary embodiments, the precursor cell is a HSC. Stem cell factor (SCF), also known as the c-kit ligand or mast cell growth factor, can be used alone to immortalize a HSC or in combination with, for example, one or more of the following growth factors: Flt-3L, IL-3, IL-6, IL-11, SCF, TPO, GM-CSF, and/or G-CSF. The amount of SCF, Flt-3L, IL-6, or TPO can be in the range of 5-1000 ng/ml, more preferably about 10-500 ng/ml, most preferably about 10-300 ng/ml. In certain specific embodiments, the amount of SCF, Flt-3L, IL-6, or TPO is 10, 20, 50, 75 125, 150, 175, 200, 225, 250, 275, 300, 325, 350, 375, 400, 425, or 450 ng/ml. The amount of IL-3, IL-11 G-CSF, or GM-CSF can be in the range of 1-100 ng/ml, more preferably about 5-50 ng/ml. more preferably about 7.5-25 ng/ml, most preferably about 10-15 ng/ml. In certain specific embodiments, the amount of IL-3, IL-11, G-CSF, or GM-CSF is 5, 6, 7, 8, 9, 10, 12.5, or 15 ng/ml. In a preferred embodiment, the foregoing factors are added to HSC in serum free medium. Growth factors can also be provided in the following combination: IL-3; IL-6; TPO; SCF and Flt-3. Growth factors can also be provided in the following combinations and amounts: IL-3 (10 ng/ml); IL-6; TPO; SCF and Flt-3 (each 50 ng/ml).

In a preferred embodiment for immortalizing HSC, the cells are cultured in a tissue culture dish onto which an extracellular matrix protein is bound. In a preferred mode of the embodiment, the extracellular matrix protein is fibronectin (FN), or a fragment thereof. Such a fragment includes but is not limited to CH-296 (Dao et al., 1998, Blood 92(12): 4612-21).

In a specific embodiment for immortalizing HSC, the cells are cultured on a plastic tissue culture dish containing a Notch 1 agonist, a Notch 2 agonist or a Notch 1 agonist and a Notch 2 agonist in the presence of IL-3; IL-6; TPO; SCF and Flt-3. In another specific embodiment for immortalizing HSC, the cells are cultured on a plastic tissue culture dish containing a Notch 1 agonist, a Notch 2 agonist or a Notch 1 agonist and a Notch 2 agonist in the presence of 100 ng/ml of each of SCF, Flt-3L, TPO and IL-6 and 10 ng/ml of IL-3. In another specific embodiment for immortalizing HSC, the cells are cultured on a plastic tissue culture dish containing a Notch 1 agonist, a Notch 2 agonist or a Notch 1 agonist and a Notch 2 agonist in the presence of 100 ng/ml of each of SCF and Flt-3L and 10 mg/ml of G-CSF and GM-CSF. In another specific embodiment for immortalizing HSC, the cells are cultured on a plastic tissue culture dish containing a Notch 1 agonist, a Notch 2 agonist or a Notch 1 agonist and a Notch 2 agonist in the presence of 100 ng/ml of each of SCF, Flt-3L and TPO and 10 mg/ml of GM-CSF. In yet another specific embodiment for immortalizing HSC, the cells are cultured on a plastic tissue culture dish containing a Notch 1 agonist, a Notch 2 agonist or a Notch 1 agonist and a Notch 2 agonist in the presence of 300 ng/ml of each of SCF and Flt-3L, 100 ng/ml of each of TPO and IL-6, and 10 mg/ml of IL-3. In a highly preferred embodiment for immortalizing HSC, the cells are cultured on a plastic tissue culture dish containing a Notch 1 agonist, a Notch 2 agonist or a Notch 1 agonist and a Notch 2 agonist in the presence of 100 ng/ml of each of SCF, Flt-3L, and TPO and 10 mg/ml of each of G-CSF and GM-CSF. In alternative embodiments to the foregoing culture conditions, fibronectin or another extracellular matrix protein can be included in the tissue culture dishes.

When differentiation is desired, SCF can be used in combination with GM-CSF or interleukin-7 (IL-7) to differentiate Immortalized HSCs into myeloid stem cells or lymphoid stem cells, respectively. In other embodiments, a retinoic acid receptor (RAR) agonist, most preferably all trans retinoic acid (ATRA) is used to promote the differentiation of an immortalized HSC into a HPP-CFC.

In other embodiments, EGF can be used in conjunction with a Notch 1 agonist, a Notch 2 agonist or a Notch 1 agonist and a Notch 2 agonist to immortalize epithelial and fibroblastic cells, alone or in combination with IGF-1 and TGF-β. In another embodiment, FGF-1 can be used in conjunction with a Notch 1 agonist, a Notch 2 agonist or a Notch 1 agonist and a Notch 2 agonist to immortalize endothelial cells. In yet another embodiment, FGF-2 can be used in conjunction with a Notch 1 agonist, a Notch 2 agonist or a Notch 1 agonist and a Notch 2 agonist to immortalize mesodermal and neurectodermal cells or to differentiate adipocyte and ovarian granulosa cells. In yet other embodiments, FGF-7 can be used in conjunction with a Notch 1 agonist, a Notch 2 agonist or a Notch 1 agonist and a Notch 2 agonist for keratinocyte immortalization and/or differentiation, or prostate epithelial immortalization and/or differentiation. In another embodiment, HGF can be used in conjunction with a Notch 1 agonist, a Notch 2 agonist or a Notch 1 agonist and a Notch 2 agonist to immortalize hepatocytes. In yet another embodiment, IL-6 can be used in conjunction with a Notch 1 agonist, a Notch 2 agonist or a Notch 1 agonist and a Notch 2 agonist to differentiate keratinocytes or neuronal stem and progenitor cells. In yet another embodiment, PDGF can be used in conjunction with a Notch 1 agonist, a Notch 2 agonist or a Notch 1 agonist and a Notch 2 agonist to immortalize mesodermal and neurectodermal cells, alone or in combination with EGF and/or IGF-1. In yet other embodiments, NGF, CNTF, GDNF or BDNF can be used individually or in combination in conjunction with a Notch 1 agonist, a Notch 2 agonist or a Notch 1 agonist and a Notch 2 agonist to immortalize neuronal cells.

The growth factors utilized by the methods of the disclosure can be obtained commercially, produced by recombinant expression, or chemically synthesized. For example, ATRA, BDNF (human), CNTF (human and rat), EGF (human), FGF-1 (human and bovine), FGF-2 (human and bovine), FGF-7 (human), Flt-3L (human), GDNF (human and rat), HGF (human), IGF-1 (human), IL-6 (human and mouse), IL-11 (human), NGF (murine), PDGF (human AA, AB, and BB isoforms), SCF (human), TGF-β (human), TPO (human and murine) can be purchased from Sigma (St. Louis, Mo.). EGF (human and murine), FGF-1 (human), FGF-2 (human), GM-CSF (human and murine), IGF-1 (human), IL-6 (human and murine), IL-7 (human and murine), NGF (murine), PDGF (human AA, AB, and BB isoforms), SCF (human) and TGF-β (human) can be purchased from Life Technologies, Inc. (Rockville, Md.).

In other embodiments, the growth factors are produced by recombinant expression (e.g., as described in Section 4.3, infra), or by chemical peptide synthesis (e.g., by a peptide synthesizer). Growth factor nucleic acid and peptide sequences are generally available from GenBank. Exemplary GenBank accession numbers for growth factors (which provide both the nucleic acid sequences and the sequences of the encoded proteins) are provided below:

| Growth Factor | Accession No. of Human Gene | Accession No. of Murine Gene |
|---|---|---|
| EGF | NP_001954.1(protein)/ X04571.1(cDNA) | J00380 |
| Epo | X02158 | M12482 |
| FGF-1 | A33665 (protein)/AH004637 (cDNA) | U67610 |
| FGF-2 | NM_002006 | NM_008006 |
| FGF-7 | M60828 | NM_008008 |
| Flt-3L | U04806 | U04807 |
| GM-SCF | X03021 | X03020 |
| HGF | P14210(protein)/E03331(cDNA) | D10212 |
| IGF-1 | M29644 | NM_010512 |
| IL-3 | M20137 | K03233 |
| IL-6 | M29150 | M20572 |
| IL-7 | AH006906 | AH001973 |
| IL-11 | M57765 | U03421 |
| NGF | CAA37703 (protein)/E03589 (cDNA) | AAA37686 (protein)/ AH001904 (cDNA) |
| PDGF | X03795 (A chain) NM_002608 (B chain) | M29464 (A chain) |
| SCF | M59964 | M57647 |
| TGF-β | M60315 | M13177 |
| Tpo | U59494 | L34169 |

Preferably, but not necessarily, the growth factor used to immortalize and optionally differentiate a precursor cell in the presence of a Notch 1 agonist, a Notch 2 agonist or a Notch 1 agonist and a Notch 2 agonist by the methods of the disclosure is derived from the same species as the precursor cell. The particular growth factor(s) utilized to immortalize or differentiate a precursor cell depends on the precursor cell type, and are well known to those of skill in the art.

The amount or concentration of growth factors suitable for immortalizing a precursor cell or differentiating an immortalized precursor cell will depend on the activity of the growth factor preparation, the species correspondence between the growth factors and the precursor cell, etc. Generally, when the growth factor(s) and the precursor cell are of the same species, the total amount of growth factor in the culture medium ranges from 1 ng/ml to 5 µg/ml, more preferably from 5 ng/ml to 1 µg/ml, and most preferably from about 10 ng/ml to 200 ng/ml. In a preferred embodiment, the precursor cell is a HSC and is immortalized by exposing the cell to a Notch 1 agonist, a Notch 2 agonist or a Notch 1 agonist and a Notch 2 agonist and 100 ng/ml of SCF. In another preferred embodiment, the precursor cell is a HSC and is immortalized by exposing the cell to a Notch 1 agonist, a Notch 2 agonist or a Notch 1 agonist and a Notch 2 agonist and IL-3; IL-6; TPO; SCF and Flt-3. In another preferred embodiment, an immortalized HSC is differentiated into a lymphoid precursor cell by exposing the cell to 100 ng/ml of each of SCF and IL-7. In yet another preferred embodiment, a HSC is differentiated into a myeloid precursor cell by exposing the cell to 100 ng/ml of each of SCF and GM-CSF.

6.3 Recombinant Expression of Notch 1 and Notch 2 Agonists and Growth Factors

The present disclosure provides methods for immortalizing and optionally differentiating precursor cells, the methods comprising culturing precursor cells in the presence of a Notch 1 agonist, a Notch 2 agonist or a Notch 1 agonist and a Notch 2 agonist and selected growth factors. In specific embodiments, Notch 1 agonist and Notch 2 agonist and/or growth factor are recombinantly produced. The Notch 1 agonist and Notch 2 agonist or growth factor can be isolated for addition to the cell culture medium in which the precursor cells are cultured, recombinantly expressed in the precursor cell during the immortalization and/or differentiation period, or endogenously or recombinantly expressed in a cell that is cultured together with the precursor cell during the immortalization and/or differentiation period.

Methods for expressing Notch 1 agonist and Notch 2 agonist and growth factors are provided herein. The nucleotide sequence coding for a growth factor or growth factor pathway component, for Notch or Notch pathway component, or for a functionally active fragment or other derivative thereof, is referred to in this section as a "Nucleic Acid of Interest", and the protein it encodes the "Protein of Interest". The Nucleic Acid of Interest can be inserted into an appropriate expression vector, i.e., a vector which contains the necessary elements for the transcription and translation of the inserted protein-coding sequence. The necessary transcriptional and translational signals can also be supplied by the native gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding a Protein of Interest thereof may be regulated by a second nucleic acid sequence so that the Protein of Interest is expressed in a host transformed with the recombinant DNA molecule. For example, expression of a Protein of Interest may be controlled by any promoter/enhancer element known in the art. Promoters which may be used to control cell fate control gene or cell fate gene pathway component expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); the regulatory sequence of the heat shock protein 70 gene (Bienz and Pelham, 1986, Cell 45:753-60) prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), β-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In one embodiment, a method that makes use of a tetracycline-regulated gene expression from E. coli, referred to as the "Tet system" (Gossen et al., 1995, Science 268: 1766-1769; Gossen and Bujard, 1992, Proc. Natl. Acad. Sci. USA 89:5547-5551), is used to direct gene expression. In this case, transgenic cell lines are generated where the coding region for a tetracycline-controlled transcriptional activator (tTA) is operably fused to promoters/enhancers that direct the expression of tTA in a constitutive or inducible manner. The transgenic cell lines are generated where the coding region for the Nucleic Acid of Interest to be mis-expressed is operably fused to a promoter that possesses a tTA-responsive regulatory element. When the cell culture medium is supplemented with a sufficient amount of tetracycline, it completely blocks expression of the gene-of-interest in the resulting progeny. Expression of the gene-of-interest can be induced at will simply by removal of tetracycline from the food or cell culture media. Also, the level of expression of the gene-of-interest can be adjusted by varying the level of tetracycline in the food. Thus, the use of the Tet system as a binary control mechanism for mis-expression has the advantage of providing a means to control the amplitude and timing of mis-expression of the Nucleic Acid of Interest.

Expression vectors containing a Nucleic Acid of Interest can be identified by four general approaches: (a) nucleic acid hybridization; (b) molecular biology, (c) expression of inserted sequences; and (d) presence or absence of "marker" gene functions. In the first approach, the presence of a Nucleic Acid of Interest inserted in an expression vector can be detected by nucleic acid hybridization using probes comprising sequences that are homologous to an inserted Nucleic Acid of Interest. In the second approach, a combination of molecular biology and "marker" gene function are used to identify recombinant expression vectors containing the Nucleic Acid of Interest. For example, if the Nucleic Acid of Interest is inserted into a particular restriction site of an expression vector which codes for both antibiotic resistance, bacterial cells that take up the vector are identified by their resistance to the antibiotic, and those vectors containing the Nucleic Acid of Interest can be identified by restriction digestion of the amplified vector DNA with the particular restriction enzyme. In the third approach, recombinant expression vectors can be identified by assaying the Protein of Interest expressed by the recombinant. Such assays can be based, for example, on the physical or functional properties of the Protein of Interest. In the fourth approach, the vector/host system can be identified based upon the presence or absence of certain "marker" gene functions (e.g. thymidine kinase activity, β-galactosidase, resistance to antibiotics, transformation phenotype, occlusion body formation in baculovirus, etc.) caused by the insertion of a Nucleic Acid of Interest in the vector. For example, if the Nucleic Acid of Interest is inserted within the marker gene sequence of the vector, recombinants containing the Nucleic Acid of Interest can be identified by the absence of the marker gene function.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g. lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Protein of Interest (Notch 1 and Notch 2 agonists, for example) may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce large quantities of Notch 1 and Notch 2 agonists, as little posttranslational modification is required for their function. Expression in a eukaryotic cell will produce a glycosylated product, which is necessary for some proteins such as TPO. Expression in metazoan cells can be used to ensure "native" processing of the signal sequences of signaling molecules.

In other specific embodiments, the Protein of Interest may be expressed as a fusion, or chimeric protein product (comprising the peptide, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g. by use of a peptide synthesizer. Both cDNA and genomic sequences can be cloned and expressed.

The methods described in this section are also applicable to genes and proteins that are not components of the Notch pathway, but to genes and proteins that may be used to indirectly alter the function of a gene or protein of the Notch pathway.

6.4 Precursor Cells

The present disclosure provides methods for immortalizing and optionally differentiating precursor cells, by circumventing or delaying the entry of the precursor cells into cell cycle arrest or into a nonreplicative phase. Precursor cells for immortalization according to the disclosure are non-terminally-differentiated cells and can be from any species, including but not limited to human, animal, plant, mammal, primate, mouse, rat, dog, cat, horse, cow, fowl, insect, *Drosophila*, and *C. elegans*. Most preferably, the precursor cells are vertebrate, more preferably mammalian, and most preferably human. In a preferred embodiment, the precursor cells are have not gone through a "crisis" or "senescence" phase resulting in cell line characteristics (e.g. transformation resulting in a stable phenotypic change (see Freshney, 1994, In "Culture of Animal Cells—A manual of Basic Technique," 3rd Edition at p. 12, John Wiley & Sons, Inc.). In a preferred embodiment, the precursor cells are primary cells. The term "primary cells" indicates that the cells are have not been through a subculture following their explanation from a tissue source, such as a mammalian subject.

Generally, though not necessarily, the precursor cells are pluripotent stem cells or multipotent progenitor cells. In one embodiment, the precursor cells are stem cells. In another embodiment, the precursor cells are progenitor cells. The precursor cells can be isolated from a cell population, if desired, before or after immortalization. Activation of Notch pathway is preferably achieved by exposing the cell to a Notch 1 agonist, Notch 2 agonist or Notch 1 agonist and Notch 2 agonist e.g. immobilized on a solid surface in or recombinantly expressed on a cell surface or, or by introducing into the cell a recombinant nucleic acid expressing a dominant active Notch mutant or an activating Notch ligand, or other molecule that activates Notch 1 and/or Notch 2.

Most preferably, when the immortalized and/or differentiated progeny of the precursor cells are to be used for repopulation or gene therapy, the precursor cells are obtained directly from tissues of a subject to whom they are administered after immortalizing and, optionally, differentiating. For example, if the precursor cell is a HSC, it can be immortalized following its isolation from a subject by culturing the cell in the presence of a Notch 1 agonist, a Notch 2 agonist or a Notch 1 agonist and a Notch 2 agonist and a combination of IL-3, IL-6, TPO, SCF and Flt-3L. In another embodiment, the cell is cultured as described then exposed to SCF and either GM-CSF or IL-7 to stimulate differentiation into myeloid or lymphoid lineages, respectively, then the resulting myeloid or lymphoid cell population transplanted back to the subject. The transplantation is preferably autologous, but can also be non-autologous. For non-autologous transplantation, the recipient is preferably given an immunosuppressive drug to reduce the risk of rejection of the transplanted cell.

The following exemplary embodiments describe approaches which allow for the isolation of precursor cells and precursor cell-containing tissues, which are to be treated with a Notch 1 agonist, a Notch 2 agonist or a Notch 1 agonist and a Notch 2 agonist and growth factors according to the present disclosure. As already alluded to, isolated cell types or even mixtures of cell populations can be treated according to the method of the disclosure. If the resulting cell population is to be used for transplantation, a recombinant gene can be introduced into the cell so that it or its progeny expresses a desired gene product before transplantation. Introduction of a recombinant gene can be accomplished either before or after precursor cell expansion and/or differentiation.

In a preferred embodiment, the precursor cell populations are purified or at least highly enriched. However, in order to immortalize and/or differentiate precursor cells by the methods of the present disclosure it is not necessary that the precursor cells are a pure population. Once a mixture is treated, the desired population can be selected for and purified. Furthermore, purification may not be necessary or desirable prior to therapeutic administration in vivo.

The isolation of precursor cells for use in the present disclosure can be carried out by any of numerous methods commonly known to those skilled in the art. For example, one common method for isolating precursor cells is to collect a population of cells from a subject and using differential antibody binding, wherein cells of one or more certain differentiation stages are bound by antibodies to differentiation antigens, fluorescence activated cell sorting (FACS) is used to separate the desired precursor cells expressing selected differentiation antigens from the population of isolated cells. FACS is a well-known method for separating particles, including cells, based on the fluorescent properties of the particles (Kamarch, 1987, Methods Enzymol. 151:150-165). Laser excitation of fluorescent moieties in the individual particles results in a small electrical charge allowing electromagnetic separation of positive and negative particles from a mixture.

In another embodiment, magnetic beads can be used to isolate precursor cells from a cell population. Specifically, a magnetic activated cell sorting (MACS) technique may be used. MACS is a method for separating particles based on their ability to bind magnetic beads (0.5-100 µm diameter). Magnetic beads can be obtained from Dynal (Oslo, Norway; http://www.dynal.no). A variety of useful modifications can be performed on the magnetic microspheres, including covalent addition of antibody which specifically recognizes a cell-solid phase surface molecule or hapten. A magnetic field is then applied, to physically manipulate the selected beads. The beads are then mixed with the cells, e.g. the cell population comprising precursor cells, to allow binding. The cells are then passed through a magnetic field to separate out cells having the desired cell surface markers.

In another embodiment, the surface of a culture dish may be coated with antibodies, and used to separate cells by a method called panning. Cells can be incubated successively in separate dishes, each of which is coated with an antibody against a marker of the desired cell type, and rinsed thoroughly following each incubation. The particular combination of antibodies utilized recognizes a corresponding combination of markers that are specific to the desired cell type but not other cell types that are likely to exist in the mixed cell population. Following the final rinse step, the cells left bound to the plate will be cells of the desired cell type.

Immortalized or Differentiated cells can be diluted into separate dishes, such as microtiter dishes, for clonal isolation. Preferably, prior to dilution, cells of the desired cell type may be purified by any method known in the art. For example, the Immortalized or Differentiated cells may be purified by FACS or MACS. In addition to endogenous markers of the precursor or differentiated cell types, the Immortalized or Differentiated cells may be purified by transfecting the precursor cell with construct encoding a reporter gene under the control of a lineage-specific promoter that is activated in the desired cell type (see e.g. U.S. Pat. No. 5,639,618).

The following section describes exemplary methods for the extraction or isolation of specific types of cells. In addition, any method known in the art can be employed.

6.4.1. Hematopoietic Cells

Preferably, the precursor cells expanded according to a method described herein are hematopoietic precursor cells. The methods of the present disclosure encompass the immortalization and optionally differentiation of any non-terminally differentiated hematopoietic cell, including but not limited to HSCs, lymphoid stem cells and myeloid stem cells. Any technique which provides for the isolation of hematopoietic cells can be used in this embodiment of the disclosure.

In a preferred embodiment, the hematopoietic cell is a HSC. A hematopoietic stem cell is also referred to as a long-term marrow engrafting cell. In a preferred embodiment, the hematopoietic stem cells and/or hematopoietic progenitor cells are human hematopoietic stem cells and/or hematopoietic progenitor cells.

Techniques by which the isolation of HSCs can be accomplished include the isolation HSCs from bone marrow cells isolated from a donor, or where the progeny of the HSC are to be used for transplantation, the future host. Non-autologous HSC are used preferably in conjunction with a method of suppressing transplantation immune reactions of a future host/subject. In a particular embodiment of the present disclosure, human bone marrow cells can be obtained from the posterior iliac crest by needle aspiration (see, e.g. Kodo et al., 1984, J. Clin. Invest. 73:1377-1384). In a preferred embodiment of the present disclosure, the HSCs or their progeny can be made highly enriched or in substantially pure form. This enrichment can be accomplished before, during, or after immortalizing and/or differentiating according to the methods of the present disclosure.

Another technique for the isolation of HSCs is described by Milner et al., 1994, Blood 83:2057-2062. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that CD34+ HSCs, including the immature subset that lacks expression of individual lineage associated antigens, CD34+lin−, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for HSCs are also known in the art (e.g., spleen focus forming assays, assays that detect the ability to form progenitors after replating).

In a specific embodiment, the precursor cells are hematopoietic stem cells. In a specific embodiment, the precursor cells are hematopoietic progenitor cells. In a specific embodiment, the precursor cells are hematopoietic stem and hematopoietic progenitor cells.

In one embodiment, hematopoietic precursor cells comprise multipotent progenitor cells that are short-term marrow engrafting cells (rapidly repopulating cells).

In a specific embodiment, the precursor cells are a population of cells enriched for hematopoietic stem cells. In another embodiment, the precursor cells are a population of cells enriched for hematopoietic stem and progenitor cells.

Hematopoietic Cell Markers

The following markers of hematopoietic cell types can be used to identify hematopoietic cells and to select or enrich the desired hematopoietic cell types (in the precursor cell population or in Immortalized or Differentiated cell populations).

Groups of antibodies have been used to distinguish different cells of the hematopoietic system, based primarily on the differential expression of various cell surface antigens on different hematopoietic cell types. Monoclonal antibodies can be used in conjunction with cell sorting to enrich for hematopoietic cells of choice. For example, human HSCs were initially purified on the basis of CD34 expression and lack of CD38 expression. Using anti-CD34 antibodies, HSCs could be enriched from 1-2% of a normal bone marrow cell population (Civin et al., 1989, Report on the CD34 cluster workshop, In: Leucocyte typing IV, White Cell Differentiation Antigens. Knapp et al., Eds., Oxford University Press. Oxford, p. 818) to approximately 50-80% of the population (Ishizawa et al., In: HSCs: The Mulhouse Manual, Wunder et al., eds. AlphaMed Press, Ohio pp 171-182; Shpall et al., 1994, J. Clinical Oncology 12:28-36; Winslow et al., 1994, Bone Marrow Transplantation 14:265-271; Thomas, 1994, Cancer Research, Therapy and Control 4(2): 119-128). Any combination of antibodies known in the art can be used to identify or select for a desired hematopoietic cell type, either by selection for cells that express antigens present on the cells of interest or by depletion of cells that express unwanted antigens.

In addition to being CD34+, HSCs are preferably CD33−, CD38−, HLA DR− and Thy-1-lo (Craig et al., 1993, J. Exp. Med. 177:1331; Civin et al., 1994, J. Immunol. 133:157; Civin et al., 1987, Exp. Hematol. 15:10; Terstappen et al., 1991, Blood 77:1218). Further, human HSCs are preferably CD45Ra−, CD19− and c-kit+ (U.S. Pat. No. 5,965,437 to Scadden).

Another HSC marker which can be used to select and/or enrich for HSCs is cells the vascular endothelial growth factor receptor 2 (VEGFR2, also known as KDR; Ziegler et al., 1999, Science 285:1553-1558).

Human hematopoietic progenitor cells and human HSCs also be enriched by incubating a sample such as bone marrow extract with antibodies that recognize glycophorin A, CD3, CD24, CD16, and CD14 and separating the antibody-bound cells from non-antibody bound cells. Antibodies against CD45RA, CD36, CD56, CD2, CD19, CD66a and CD66b can also be used to refine this process. The non-antibody bound cell population is enriched for hematopoietic stem and progenitor cells (see U.S. Pat. No. 5,877,299 to Thomas and Lansdorp). In other studies, My10 and HLA-DR antibodies have been used in association with two color sorting to obtain highly enriched progenitor cell populations from human marrow (Lu et al., 1987, J. Immunol. 139(6):1823-1829). T lymphocyte depletion can also be used to enrich for hematopoietic stem or progenitor cells. In this procedure, T lymphocytes are selectively removed from the cell population by pretreating cells with a monoclonal antibody(ies), that recognize a T cell antigen, plus complement. Such a procedure has been described previously (Broxmeyer et al., 1984, J. Clin. Invest. 73:939-953).

Glycophorin A antibodies can be used to select for or against erythrocytes. Antibodies against CD14, CD16, CD66a and CD66b can be used to select for or against monocytes. Antibodies against CD24, CD3, CD19, CD20, CD56, CD2 can be used to select for or against B and T lymphocytes and NK cells. Antibodies against CD45RA and CD36 can be used to select for or against T-cells, B-cells, granulocytes, platelets, monocytes, differentiated erythroid precursors, and some committed mature progenitors. See, e.g., U.S. Pat. No. 5,877,299. Other T-cell markers include CD7, CD5, TCD-2, and either CD4 or CD8. CD7 and terminal deoxyribonucleotidyl transferase (Tdt) are markers of pre-T progenitor cells. Additional markers of pre-B progenitor cells are MHC class II antigens. Mature B cells are further characterized by the expression of CD21. See, e.g., Raska and Ponzio, 1994, In "Immunology and Inflammation: Basic Mechanisms and Clinical Consequences," Sigal and Ron, Eds., McGraw-Hill, Inc.

In specific embodiments, antibodies which are currently available and can be used in enrichment protocols include My-10 and 3C5 (which recognize CD34), or RFB-1 (which recognizes CD99 (Petty and Tippett, 1995, Vox Sang 69(3): 231-5) and identifies populations of BFU-E cells (Kannourakis and Johnson, 1988, Blood 71(3):758-65)). Other currently available antibodies against the above-mentioned hematopoietic antigens are disclosed in U.S. Pat. No. 5,877, 299. These antibodies can be used alone or in combination with procedures such as "panning" (Broxmeyer et al., 1983, J. Clin. Invest. 73:939-953) or fluorescence activated cell-sorting (FACS) (Williams et al., 1985, J. Immunol. 135: 1004; Lu et al., 1986, Blood 68(1): 126-133) to isolate those cells containing surface determinants recognized by the monoclonal antibodies.

Another method that can be used is that of separating the stem and progenitor cells by means of selective agglutination using a lectin such as soybean (Reisner et al., 1980, Proc. Natl. Acad. Sci. U.S.A. 77:1164). This procedure can be a viable alternative for separation and enrichment of stem and progenitor cells without removal of possibly necessary accessory cells (Reisner et al., 1983, Blood 61(2):341-348; Reisner et al./, 1982, Blood 59(2):360-363).

Theoretically, only one early stem cell is needed for repopulation of the entire hematopoietic system. There is laboratory evidence that under ideal conditions and when the microenvironment nurturing the stem and progenitor cells in the recipient animal is not affected, a single stem cell can entirely repopulate the defective hematopoietic system of a mouse and rescue it from the lethal complications of anemia (Boggs et al., 1982, J. Clin. Invest. 70:242-253). Doubtless, under clinical conditions in man it would generally require more than a single stem cell to rescue the hematopoietic system. Moreover, the presence of accessory or helper cells (non-stem/progenitor cells that influence the growth of stem/ progenitor cells), in addition to stem and progenitor cells, may be required (Spooncer et al., 1985, Nature (London) 316:62-64), especially if the microenvironment of the host is injured by treatments such as irradiation or chemotherapy. Thus, while there are ways to separate hematopoietic stem and progenitor cells from other cord blood cells (Leary et al., 1984, J. Clin. Invest. 74:2193-2197) and these and other methods could be used to isolate and store pure or highly enriched preparations of these cells for immortalization and eventually transplantation, caution should be used in attempts at transplanting patients with purified preparations of stem and progenitor cells.

6.4.2. Mesenchymal Stem Cells

One of the most important type of precursor cells for therapeutic applications are those derived from the mesenchyme. Mesenchymal stem cells are pluripotent cells found in the bone marrow, blood, dermis, and periosteum that are capable of differentiating into cells of various lineages (e.g., steogenic, chondrogenic, tendonogenic, adipogenic, myogenic lineages, etc.) depending on the in vitro or in vivo microenvironment. (Caplan, 1991, J. Orth. Res. 641-650). Most work to date involves the isolation and culture of cells which can differentiate into chondrocytes and osteoblasts. The systems developed to isolate the relevant progenitor cell populations were worked out first in chick embryos (Caplan, 1970, Exp. Cell. Res. 62:341-355; Caplan, 1981, 39th Annual Symposium of the Society for Developmental Biology, pp. 37-68; Caplan et al., 1980, Dilatation of the Uterine Cervix 79-98; DeLuca et al., 1977, J. Biol. Chem. 252:6600-6608; Osdoby et al., 1979, Dev. Biol. 73:84-102; Syftestad et al., 1985, Dev. Biol. 110:275-283).

Caplan et al., 1993, and Caplan et al., 1996, U.S. Pat. Nos. 5,226,914 and 5,486,359 respectively, describe exemplary methods for isolating mesenchymal stem cells from bone marrow. These isolated marrow stem cells can be immortalized using a Notch 1 agonist, a Notch 2 agonist or a Notch 1 agonist and a Notch 2 agonist and growth factors that promote proliferation but not differentiation. These precursor cells, may then be further differentiated, e.g. by growing in the presence of growth factors that promote differentiation. The cells are preferably differentiated into osteocytes, cartilage, chondrocytes, adipocytes, etc.

Several bone marrow isolation protocols have been reported and can be used to obtain precursor cells. Single cell suspensions from rat bone marrow can be prepared according to Goshima et al., 1991, Clin. Orth. and Rel. Res. 262:298-311. Human stem cell cultures from marrow can be prepared as described by Bab et al., 1988, Bone Mineral 4:373-386 as follows: Whole marrow cells are obtained from subjects. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described previously (Bab et al., 1984, Calcif. Tissue Int. 36:77-82; Ashton et al., 1984, Calcif. Tissue Int. 36:83-86) by drawing the preparation into a syringe and expelling it several times sequentially through 19, 21, 23 and 25 gauge needles. The cells are counted using a fixed volume hemocytometer and the concentration adjusted to $1-5 \times 10^8$ total marrow cells per ml suspension. Positive and negative control cell suspensions can be set as described before (Shteyer et al., 1986, Calcif. Tissue Int. 39:49-54), using rabbit whole marrow and spleen cells, respectively. 6.4.3. Fibroblasts Connective tissue comprises fibroblasts, cartilage, bone, adipose and smooth muscle cells. Fibroblasts are the least differentiated of the connective tissue cells and are dispersed in connective tissues throughout the body. They can be identified by their characteristic secretion of type I and/or type III collagen. Fibroblasts can migrate into tissue wounds and secrete a collagenous matrix that heals and isolates the wounds. Further, they can differentiate into other members of the connective tissue family, depending on their local cues. Fibroblasts can be isolated from a variety of different tissues, including but not limited to the bone marrow stroma, according to methods known to those of ordinary skill in the art.

6.4.4. Neural Stem Cells

It is generally assumed that neurogenesis in the central nervous system ceases before or soon after birth. In recent years, several studies have presented evidence indicating that at least to some degree new neurons continue to be added to the brain of adult vertebrates (Alvarez-Buylla and Lois, 1995, Stem Cells (Dayt) 13:263-272). The precursors are generally located in the wall of the brain ventricles. It is thought that from these proliferative regions, neuronal precursors migrate towards target positions where the microenvironment induces them to differentiate. Studies have been reported where cells from the sub-ventricular zone can generate neurons both in vivo as well as in vitro, reviewed in Alvarez-Buylla and Lois, 1995, Stem Cells (Dayt) 13:263-272.

The neuronal precursors from the adult brain can be used as a source of cells for neuronal transplantation (Alvarez-Buylla, 1993, Proc. Natl. Acad. Sci. USA 90:2074-2077). Neural crest cells have also been long recognized to be pluripotent neuronal cells which can migrate and differentiate into different cell neuronal cell types according to the instructions they receive from the microenvironment they find themselves in (LeDouarin and Ziller, 1993, Curr. Opin. Cell Biol. 5:1036-1043).

6.4.5. Fetal Cells

In certain embodiments of the present disclosure, precursor cells can be fetal cells, e.g., for culturing until required at a later point in life. Fetal blood can be obtained by any method known in the art. For example, fetal blood can be taken from the fetal circulation at the placental root with the use of a needle guided by ultrasound (Daffos et al., 1985, Am. J. Obstet. Gynecol. 153:655-660; Daffos et al., 1983, Am. J. Obstet. Gynecol. 146:985), by placentocentisis (Valenti, 1973, Am. J. Obstet. Gynecol. 115:851; Cao et al., 1982, J. Med. Genet. 19:81), by fetoscopy (Rodeck, 1984, in Prenatal Diagnosis, Rodeck, C. H. and Nicolaides, K. H., eds., Royal College of Obstetricians and Gynecologists, London), etc. In certain embodiments, fetal cells are obtained from umbilical cord blood, placental blood or Wharton's jelly. Wharton's jelly is a gelatinous substance found in the umbilical cord which has been generally regarded as a loose mucous connective tissue, and has been frequently described as consisting of fibroblasts, collagen fibers and an amorphous ground substance composed mainly of hyaluronic acid (Takechi et al., 1993, Placenta 14:235-45).

Alternatively, the precursor cells of the disclosure can be obtained from neonatal blood. Neonatal blood can preferably be obtained by direct drainage from the cord and/or by needle aspiration from the delivered placenta at the rot and at distended veins.

Collections should be made under sterile conditions. Immediately upon collection, the neonatal or fetal blood should be mixed with an anticoagulant. Such an anticoagulant can be any known in the art, including but not limited to CPD (citrate-phosphate-dextrose), ACD (acid citrate-dextrose), Alsever's solution (Alsever and Ainslie, 1941, N.Y. St. J. Med. 41:126), DeGowin's Solution (DeGowin et al., 1940, J. Am. Med. As. 114:850), Edglugate-Mg (Smith et al., 1959, J. Thorac. Cardiovasc. Surg. 38:573), Rous-Turner Solution (Rous and Turner, 1916, J. Exp. Med. 23:219), other glucose mixtures, heparin, ethyl biscoumacetate, etc. (See, Hurn, 1968, Storage of Blood, Academic Press, New York, pp. 26-160).

Primary cultures of human fetal brain cells can be isolated from human fetuses, obtained from legal abortions after 5 to 12 weeks of gestation. Expulsion can be done by syringe-driven gentle aspiration under echographic control.

6.4.6. Epithelial Stem Cells and Keratinocytes

Epithelial stem cells (ESCs) and keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of precursor cells within the germinal layer, the layer closest to the basal lamina. Precursor cells within the lining of the gut provide for a rapid renewal rate of this tissue. ESCs obtained from the skin or lining of the gut of a subject or donor (Rheinwald, 1980, Meth. Cell Bio. 21A:229; Pittelkow and Scott, 1986, Mayo Clinic Proc. 61:771) can be immortalized according to the methods of the present disclosure.

6.4.7. Liver Stem Cells

Liver stem cells can be isolated by methods described in PCT Publication WO 94/08598, dated Apr. 28, 1994.

6.4.8. Kidney Stem Cells

Mammalian kidney emerges from the metanephric mesenchyme which induces the uteric bud to undergo a series of morphogenetic movements ultimately forming the mature urinary collecting system (Nigam and Brenner, 1992, Curr. Opin. Nephrol. Huper 1:187-191. The uteric bud, an epithelial outgrowth of the Wolfian duct, contracts and induces condensing adjacent mesenchyme along differentiation pathways of epithelial divergence in early embryonic life. Attempts to study this process in vitro have been reported; metanephros in organ culture can be induced to form tubules using embryonic spinal cord as the inducer. While the specific transducing agents that lead to the induction of metanephric mesenchyme by the uteric bud in vivo or by spinal cord in vitro are not known, cell specific markers show that the differentiation program is induced in progenitor cells (Karp et al., 1994, Dev. Biol. 91:5286-5290).

6.5 Differentiation of Precursor Cells

The present disclosure provides methods for the differentiation of precursor cells before, after or concurrently with their immortalization according to the methods of the present disclosure. Differentiation of precursor cells is accomplished by exposing the cells to one or growth factors that promote differentiation, and growing the cells under conditions that allow differentiation to take place. The growth factors for differentiating precursor cells or their Immortalized progeny include those described in section 4.2, supra. The selection of growth factors that promote the differentiation of precursor cells depends on the precursor cell types, and are known to those of skill in the art. For example, as described in section 4.2, an Immortalized HSC is differentiated into a lymphoid stem cell by exposing the cell to 100 ng/ml of each of SCF and IL-7, and into a myeloid stem cell by exposing the cell to 100 ng/ml of each of SCF and GM-CSF. In certain instances, a growth factor may be used for both differentiation and proliferation by combining it with different growth factors; for example SCF can be used alone or in combination with IL-6, IL-11, and Flt-3L to immortalize HSCs (by exposing the HSCs to SCF (and optionally IL-6, IL-11, and Flt-3L) and a Notch 1 agonist, a Notch 2 agonist or a Notch 1 agonist and a Notch 2 agonist for a time period beyond which the HSCs would normally stop proliferating and/or die), and in combination with IL-7 or GM-CSF to promote the differentiation of Immortalized HSCs into lymphoid stem cells or myeloid stem cells, respectively.

6.6 Therapeutic Uses of the Cultured Cells of the Disclosure

The present disclosure provides methods that allow the immortalization and, optionally, differentiation of precursor cells. In certain embodiments, the resulting cells are used for cell therapy. By way of example and not limitation, the following sections describe exemplary embodiments for the treatment of hematopoietic disorders and injury to nervous tissue using the cells produced by the methods of the disclosure. However, the Immortalized or Differentiated cells may be useful for replenishing any deficient cell populations or supply therapeutic cell populations of the precursor cell type or as gene therapy vectors (see Section 4.8, infra). Additionally, precursor cells can be preserved, e.g. by freezing, prior to or following immortalization (see Section 4.7, infra).

6.6.1. Hematopoietic Disorders

Transplantation of Immortalized HSCs or Differentiated hematopoietic cells may be useful in the treatment or prevention of hematopoietic disorders and diseases. In one embodiment, the Immortalized or Differentiated cells are used to treat or prevent a hematopoietic disorder or disease characterized by a failure or dysfunction of normal blood cell production and maturation cell. In another embodiment, the Immortalized or Differentiated cells are used to treat or prevent a hematopoietic disorder or disease resulting from a hematopoietic malignancy. In yet another embodiment, the Immortalized or Differentiated cells are used to treat or prevent a hematopoietic disorder or disease resulting from immunosuppression, particularly immunosuppression in subjects with malignant, solid tumors. In yet another embodiment, the Immortalized or Differentiated cells are used to treat or prevent an autoimmune disease affecting the hematopoietic system. In yet another embodiment, the Immortalized or Differentiated cells are used to treat or prevent a genetic or congenital hematopoietic disorder or disease. The type of Differentiated cells used in the treatment of a hematopoietic disease or disorder in a subject is chosen to ameliorate the subject's condition, for example cells differentiated along the erythrocytic pathways to treat anemia.

Examples of particular hematopoietic diseases and disorders which can be treated by the Immortalized and/or by the Differentiated cells of the disclosure include but are not limited to those listed in Table 2:

DISEASES OR DISORDERS WHICH CAN BE TREATED
BY HEMATOPOIETIC RECONSTITUTION WITH NEONATAL
STEM AND PROGENITOR CELLS

I. Diseases Resulting from a Failure or Dysfunction of Normal Blood Cell Production and Maturation hyperproliferative stem cell disorders
aplastic anemia
pancytopenia
agranulocytosis
thrombocytopenia
red cell aplasia
Blackfan-Diamond syndrome due to drugs, radiation, or infection
idiopathic II. Hematopoietic malignancies acute lymphoblastic (lymphocytic) leukemia
chronic lymphocytic leukemia
acute myelogenous leukemia
chronic myelogenous leukemia
acute malignant myelosclerosis
multiple myeloma
polycythemia vera
agnogenic myelometaplasia
Waldenstrom's macroglobulinemia
Hodgkin's lymphoma
non-Hodgkin's lymphoma III. Immunosuppression in patients with malignant, solid tumors malignant melanoma
carcinoma of the stomach
ovarian carcinoma
breast carcinoma
small cell lung carcinoma
retinoblastoma
testicular carcinoma
glioblastoma
rhabdomyosarcoma
neuroblastoma
Ewing's sarcoma
lymphoma -continued DISEASES OR DISORDERS WHICH CAN BE TREATED
BY HEMATOPOIETIC RECONSTITUTION WITH NEONATAL
STEM AND PROGENITOR CELLS IV. Autoimmune diseases rheumatoid arthritis
diabetes type I
chronic hepatitis
multiple sclerosis
systemic lupus erythematosus V. Genetic (congenital) disorders anemias
familial aplastic
Fanconi's syndrome
Bloom's syndrome
pure red cell aplasia (PRCA)
dyskeratosis congenita
Blackfan-Diamond syndrome
congenital dyserythropoietic syndromes I-IV
Chwachmann-Diamond syndrome
dihydrofolate reductase deficiencies
formamino transferase deficiency
Lesch-Nyhan syndrome
congenital spherocytosis
congenital elliptocytosis
congenital stomatocytosis
congenital Rh null disease
paroxysmal nocturnal hemoglobinuria
G6PD (glucose-6-phosphate dehydrogenase) variants 1, 2, 3
pyruvate kinase deficiency
congenital erythropoietin sensitivity deficiency
sickle cell disease and trait
thalassemia alpha, beta, gamma
met-hemoglobinemia
congenital disorders of immunity
severe combined immunodeficiency disease (SCID)
bare lymphocyte syndrome
ionophore-responsive combined immunodeficiency
combined immunodeficiency with a capping abnormality
nucleoside phosphorylase deficiency
granulocyte actin deficiency
infantile agranulocytosis
Gaucher's disease
adenosine deaminase deficiency
Kostmann's syndrome
reticular dysgenesis
congenital leukocyte dysfunction syndromes VI. Others osteopetrosis
myelosclerosis
acquired hemolytic anemias
acquired immunodeficiencies
infectious disorders causing primary or secondary
immunodeficiencies
bacterial infections (e.g., Brucellosis, Listerosis, tuberculosis, leprosy)
parasitic infections (e.g., malaria, Leishmaniasis)
fungal infections
disorders involving disproportions in lymphoid cell sets and
impaired immune functions due to aging
phagocyte disorders
Kostmann's agranulocytosis
chronic granulomatous disease
Chediak-Higachi syndrome
neutrophil actin deficiency
neutrophil membrane GP-180 deficiency
metabolic storage diseases
mucopolysaccharidoses
mucolipidoses
miscellaneous disorders involving immune mechanisms
Wiskott-Aldrich Syndrome
α1-antitrypsin deficiency In one embodiment, the Immortalized or Differentiated cells are administered to a subject with a hematopoietic deficiency. In one mode of the embodiment, the Immortalized or Differentiated cells are administered prenatally to a fetus diagnosed with a hematopoietic deficiency.

Hematopoietic deficiencies whose treatment with the Immortalized or Differentiated cells of the disclosure is encompassed by the methods of the disclosure include but are not limited to decreased levels of either myeloid, erythroid, lymphoid, or megakaryocyte cells of the hematopoietic system or combinations thereof, including those listed in Table 2. The type of Differentiated cells used in the treatment or prevention of a hematopoietic disease or disorder is selected so that it complements the subject's hematopoietic deficiency; for example, Immortalized HSCs that have been differentiated along a lymphocytic pathway are used to treat an individual with AIDS.

Among conditions susceptible to treatment with the cell lines of the present disclosure is leukopenia, a reduction in the number of circulating leukocytes (white cells) in the peripheral blood. Leukopenia may be induced by exposure to certain viruses or to radiation. It is often a side effect of various forms of cancer therapy, e.g. exposure to chemotherapeutic drugs, radiation and of infection or hemorrhage.

Immortalized HSCs or Differentiated hematopoietic cells may also be useful in the treatment or prevention of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome, myelofibrosis, thrombocytopenia. Severe thrombocytopenia may result from genetic defects such as Fanconi's Anemia, Wiscott-Aldrich, or May-Hegglin syndromes and from chemotherapy and/or radiation therapy or cancer. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Thrombocytopenia may also result from marrow invasion by carcinoma, lymphoma, leukemia or fibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenyloin or carbamazepine, antithyroids such as propylthiouracil and methimazole and diuretics. Transplantation of Immortalized HSCs may be useful in preventing or treating the bone marrow suppression or hematopoietic deficiencies which often occur in subjects treated with these drugs.

Hematopoietic deficiencies may also occur as a result of viral, microbial or parasitic infections and as a result of treatment for renal disease or renal failure, e.g., dialysis. Transplantation of immortalized HSCs may be useful in treating such hematopoietic deficiency.

Various immunodeficiencies e.g., in T and/or B lymphocytes, or immune disorders, e.g., rheumatoid arthritis, may also be beneficially affected by treatment with the Immortalized HSCs. Immunodeficiencies may be the result of viral infections (including but not limited to HIV, HTLVI, HTLVII, HTLVIII), severe exposure to radiation, cancer therapy or the result of other medical treatment.

6.6.2. Treatment of Nervous System Disorders and Injuries

Nervous system disorders involving cell types that require supplementation or replacement and can be replenished by transplantation of an Immortalized or Differentiated cell can be treated by the methods of the disclosure. These include but are not limited to nervous system injuries, and diseases or disorders which result in either a disconnection of axons, a diminution or degeneration of neurons, or demyelination. Nervous system lesions which may be treated in a subject (including human and non-human mammalian subjects) according to the disclosure include but are not limited to the following lesions of either the central (including spinal cord, brain) or peripheral nervous systems: (i) traumatic lesions, including lesions caused by physical injury or associated with surgery, for example, lesions which sever a portion of the nervous system, or compression injuries; (ii) ischemic lesions, in which a lack of oxygen in a portion of the nervous system results in neuronal injury or death, including cerebral infarction or ischemia, or spinal cord infarction or ischemia; (iii) malignant lesions, in which a portion of the nervous system is destroyed or injured by malignant tissue which is either a nervous system associated malignancy or a malignancy derived from non-nervous system tissue; (iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis; (vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (vii) neurological lesions associated with systemic diseases including but not limited to diabetes (diabetic neuropathy, Bell's palsy), systemic lupus erythematosus, carcinoma, or sarcoidosis; (viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

In specific embodiments, motor neuron disorders that may be treated according to the disclosure include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

It will be understood to those skilled in the art that the above embodiments are merely exemplary; the Immortalized and/or Differentiated cells of the disclosure or the progeny thereof may be used in the treatment of disease that requires cell or tissue supplementation.

6.7 Preservation of Precursor Cells

In certain embodiments, the precursor cells of the disclosure are preserved (i) prior to immortalization and optionally differentiation, or (ii) following immortalization and optionally differentiation, while maintaining the integrity of both the cells and their genomes.

In a preferred embodiment, precursor cells are preserved by cryopreservation. Freezing is destructive to most living cells. Upon cooling, as the external medium freezes, cells equilibrate by losing water, thus increasing intracellular solute concentration. Below about 10°-15° C., intracellular freezing will occur. Both intracellular freezing and solution effects are responsible for cell injury (Mazur, 1970, Science 168:939-949). Accordingly, precursor cells are preferably cryopreserved using the methods that have been established to circumvent cellular damage upon freezing living cells, for example the use of cryoprotective agents and optimal cooling rates (Meryman et al., 1977, Cryobiology 14:287-302).

Precursor, Immortalized and Differentiated cells can also be preserved by freeze-drying (reviewed by Simione, 1992, J. Parenter. Sci. Technol. 46(6):226-32).

Because cryopreservation is less damaging that freeze-drying, master stocks are usually maintained at liquid nitrogen or comparable temperatures, while working stocks can be frozen or freeze-dried.

6.8 Genetic Engineering of Cells

The Immortalized cell populations can be genetically engineered to produce gene products beneficial upon transplantation of the genetically engineered cells to a subject. Such gene products include but are not limited to anti-inflammatory factors, e.g., anti-TNF, anti-IL-1, anti-IL-2, etc. Alternatively, the mesenchymal stem and progenitor cells can be genetically engineered to "knock out" expression of MHC in order to lower the risk of rejection. In addition, the cell populations can be genetically engineered for use in gene therapy to adjust the level of gene activity in a subject to assist or improve the results of transplantation or to treat a disease is caused by, for example, a deficiency in the recombinant gene. The cell populations are made recombinant by the introduction of a recombinant nucleic acid into the precursor cell or into the Immortalized or Differentiated cell population.

In its broadest sense, gene therapy refers to therapy performed by the administration of a nucleic acid to a subject. The nucleic acid, either directly or indirectly via its encoded protein, mediates a therapeutic effect in the subject. The present disclosure provides methods of gene therapy wherein a nucleic acid encoding a protein of therapeutic value (preferably to humans) is introduced into the precursor cells manipulated according to the methods of the disclosure, before or after manipulation and before or after immortalization, such that the nucleic acid is expressible by the precursor cells and/or their progeny, followed by administration of the recombinant cells to a subject.

The recombinant cells of the present disclosure can be used in any of the methods for gene therapy available in the art. Thus, the nucleic acid introduced into the cells may encode any desired protein, e.g. a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Lundstrom, 1999, J. Recept. Signal Transduct. Res. 19:673-686; Robbins and Ghivizzani, 1998, Pharmacol. Ther. 80:35-47; Pelegrin et al., 1998, Hum. Gene Ther. 9:2165-2175; Harvey and Caskey, 1998, Curr. Opin. Chem. Biol. 2:512-518; Guntaka and Swamynathan, 1998, Indian J. Exp. Biol. 36:539-535; Desnick and Schuchman, 1998, Acta Paediatr. Jpn. 40:191-203; Vos, 1998, Curr. Opin. Genet. Dev. 8:351-359; Tarahovsky and Ivanitsky, 1998, Biochemistry (Mosc) 63:607-618; Morishita et al., 1998, Circ. Res. 2:1023-1028; Vile et al., 1998, Mol. Med. Today 4:84-92; Branch and Klotman, 1998, Exp. Nephrol. 6:78-83; Ascenzioni et al., 1997, Cancer Lett. 118:135-142; Chan and Glazer, 1997, J. Mol. Med. 75:267-282. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant precursor cells are used in gene therapy, a gene whose expression is desired in a subject is introduced into the precursor cells such that it is expressible by the cells and/or their progeny, and the recombinant cells are then administered in vivo for therapeutic effect.

Recombinant cell populations can be used in any appropriate method of gene therapy, as would be recognized by those in the art upon considering this disclosure. The resulting action of recombinant cell populations administered to a subject can, for example, lead to the activation or inhibition of a pre-selected gene in the subject, thus leading to improvement of the diseased condition afflicting the subject.

In this embodiment, the desired gene is introduced into the precursor cell or its progeny prior to administration in vivo of the resulting recombinant cell. Such introduction can be carried out by any method known in the art, including but not limited to transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g. Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present disclosure, provided that the necessary developmental and physiological functions of the recipient cells are not disrupted. The technique should provide for the stable transfer of the gene to the cell, so that the gene is expressible by the cell and preferably heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject.

One common method of practicing gene therapy is by making use of retroviral vectors (see Miller et al., 1993, Meth. Enzymol. 217:581-599). A retroviral vector is a retrovirus that has been modified to incorporate a preselected gene in order to effect the expression of that gene. It has been found that many of the naturally occurring DNA sequences of retroviruses are dispensable in retroviral vectors. Only a small subset of the naturally occurring DNA sequences of retroviruses is necessary. In general, a retroviral vector must contain all of the cis-acting sequences necessary for the packaging and integration of the viral genome. These cis-acting sequences are: (a) a long terminal repeat (LTR), or portions thereof, at each end of the vector; (b) primer binding sites for negative and positive strand DNA synthesis; and (c) a packaging signal, necessary for the incorporation of genomic RNA into virions.

The gene to be used in gene therapy is cloned into the vector, which facilitates delivery of the gene into a precursor cell by infection or delivery of the vector into the cell. More detail about retroviral vectors can be found in Boesen et al. 1994, Biotherapy 6:291-302, which describes the use of a retroviral vector to deliver the mdrl gene to HSCs in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are also of use in gene therapy. Adenoviruses are especially attractive vehicles for delivering genes to respiratory precursor cells. Adenoviruses can also be used to deliver genes to precursor cells from the liver, the central nervous system, endothelium, and muscle. Adenoviruses have the advantage of being capable of infecting non-dividing cells. Kozarsky and Wilson, 1993, Current Opinion in Genetics and Development 3:499-503 present a review of adenovirus-based gene therapy. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234.

It has been proposed that adeno-associated virus (AAV) be used in gene therapy (Walsh et al., 1993, Proc. Soc. Exp. Biol. Med. 204:289-300). It has also been proposed that alphaviruses be used in gene therapy (Lundstrom, 1999, J. Recept. Signal Transduct. Res. 19:673-686).

Other methods of gene delivery in gene therapy include mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

A desired gene can be introduced intracellularly and incorporated within host precursor cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, the desired gene recombinantly expressed in the precursor cell or its progeny to be introduced for purposes of gene therapy comprises an inducible promoter operably linked to the coding region, such that expression of the recombinant gene is controllable by controlling the presence or absence of the appropriate inducer of transcription.

In a preferred embodiment, the desired gene recombinantly expressed in the precursor cell or its progeny, is flanked by Cre sites. When the gene function is no longer required, the cells comprising the recombinant gene are subjected to Lox protein, for example be means of supplying a nucleic acid containing the Lox coding sequences functionally coupled to an inducible or tissue specific promoter, or by supplying Lox protein functionally coupled to a nuclear internalization signal. Lox recombinase functions to recombine the Cre sequences (Hamilton et al., 1984, J. Mol. Biol. 178:481-486), excising the intervening sequences in the process, which according to this embodiment contain a nucleic acid of a desired gene. The method has been used successfully to manipulate recombinant gene expression (Fukushige et al., 1992, Proc. Natl. Acad. Sci. USA 89:7905-7909). Alternatively, the FLP/FRT recombination system can be used to control the presence and expression of genes through site-specific recombination (Brand and Perrimon, 1993, Development 118:401-415).

6.9 Methods of Transplantation

The Immortalized and/or Differentiated cell populations, whether recombinantly expressing a desired gene or not, can be transplanted into a subject for the treatment of disease or injury or for gene therapy by any method known in the art which is appropriate for the type of stem cell being transplanted and the transplant site. HSCs or more differentiated derivatives can be transplanted intravenously, as can liver cells which will locate to the liver. Neural stem cells can be transplanted directly into the brain at the site of injury or disease.

In a preferred embodiment, the cell populations comprising Immortalized or Differentiated cells for transplantation are purified or at least highly enriched. Methods describing the purification and enrichment of cell populations (e.g., FACS, MACS, etc.) described for precursor cells in Section 4.4, supra, are applicable to the purification or enrichment of cell populations for transplantation.

In one embodiment, the transplantation of Immortalized or Differentiated cells is autologous. Autologous transplantation can be performed, for example, when the Immortalized or Differentiated cell has been genetically engineered to express a gene that is otherwise deficient in the subject. Autologous transplantation of Immortalized or Differentiated cells can be carried out to reconstitute in a subject a hematopoietic cell population that has been depleted by chemotherapy. Preferably, HSCs are isolated for immortalization according to the methods of the disclosure prior to the subject's exposure to chemotherapy, and the Immortalized or Differentiated cells transplanted back to the subject following exposure to chemotherapy.

In another embodiment, the transplantation of Immortalized or Differentiated cells is non-autologous. This embodiment is practiced, for example, when a subject's own cells are absent or too low in number to establish a culture, or the subject is too sick to undergo an explant procedure. Non-autologous transplantations are used preferably in conjunction with a method of suppressing rejection.

Methods of introduction include but are not limited to intradermal, intramuscular, intraperitoneal, intravenous, subcutaneous, intranasal, and epidural routes. The cell populations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the disclosure into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the cell populations of the disclosure locally to the area in need of treatment; this may be achieved by, for example, and not by way of limitation, local infusion during surgery, topical application, e.g. in conjunction with a wound dressing after surgery, by injection, by means of a catheter, or by means of an implant, the implant being of a porous, non-porous, or gelatinous material, including membranes, such as sialastic membranes, or fibers.

By way of example, implantation of cells into the brain can be performed as follows. Implantation is done at three sites in the left putamen with a stereotactic technique (Lindvall et al., 1989, Arch. Neurol. 46:615). For each site, 20 μl of the dissociated cells is drawn into the instrument (outer diameter, 1.0 mm). The cells are injected along a 10, 12 and 14 mm linear tract, respectively, in either 2.5 μl portions for 15 to 20 seconds each. Between each injection there is a 2 minute delay, and the cannula is then retracted 1.5 to 1.7 mm. After the final injection, the cannula is left in situ for 8 minutes before being slowly withdrawn from the brain. After surgery the cell viability is assessed following the procedure of Brundin et al., 1985 (Brain. Res. 331:251).

In a preferred embodiment, the cell transplant is autologous. In another embodiment, the transplant is non-autologous. In a specific embodiment, the transplanted cells can be an organ or tissue type produced according to the methods of the disclosure.

The titer of stem cells transplanted which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances.

The subject is preferably an animal, including but not limited to animals such as cows, pigs, horses, chickens, cats, dogs, etc., and is preferably a mammal, and most preferably human.

6.10 Pharmaceutical Compositions

The disclosure provides methods of treatment by administration to a subject of a pharmaceutical (therapeutic) composition comprising a therapeutically effective amount of a recombinant or non-recombinant cell produced by the immortalizing and optionally differentiating a precursor cell according to the methods of the present disclosure. In a preferred aspect, the Immortalized or Differentiated cell is substantially purified.

The present disclosure provides pharmaceutical compositions. Such compositions comprise a therapeutically effective amount of an Immortalized cell, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, or emulsion.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

6.10.1. Pharmaceutical Kits

The disclosure also provides a pharmaceutical pack or kit comprising one or more containers filled with one or more of cell populations produced by the methods of the disclosure and/or reagents to prepare the cells, or with reagents for the genetic manipulation of the cells.

In a preferred embodiment, a kit of the disclosure comprises in one or more containers one or more purified growth factors that promote proliferation but not differentiation of a precursor cell and a purified Notch 1 agonist and/or Notch 2 agonist, which growth factors and Notch 1 agonist and/or Notch 2 agonist are together effective to immortalize a precursor cell exposed to them in culture. Optionally, the kit further comprises in a separate container one or more purified growth factors that promote the differentiation of the precursor cell. Optionally, cell culture medium is also provided. Optionally associated with such container(s) can be a notice in the form prescribed by a governmental agency regulating the manufacture, use or sale of pharmaceuticals or biological products, which notice reflects approval by the agency of manufacture, use or sale for human administration.

EXEMPLARY EMBODIMENTS

1. A method for producing an immortalized precursor cell population comprising culturing a non-immortalized precursor cell in the presence of (i) a Notch 1 agonist, a Notch 2 agonist or a Notch 1 agonist and a Notch 2 agonist and (ii) one or more growth factors, for a time period beyond which cells of the precursor cell type not in the presence of the (i) Notch 1 agonist, the Notch 2 agonist or the Notch 1 agonist and the Notch 2 agonist and (ii) the growth factors stop proliferating and differentiate or die such that the precursor cell proliferates but does not terminally differentiate during the time period, thereby producing an immortalized precursor cell population.

2. A method for producing an immortalized precursor cell population comprising culturing a non-immortalized precursor cell in the presence of (i) a Notch 1 agonist, a Notch 2 agonist or a Notch 1 agonist and a Notch 2 agonist in an amount that maintains low Notch signal strength and (ii) one or more growth factors, for a time period beyond which cells of the precursor cell type not in the presence of the (i) Notch 1 agonist, the Notch 2 agonist or the Notch 1 agonist and the Notch 2 agonist and (ii) the growth factors stop proliferating and differentiate or die such that the precursor cell proliferates but does not terminally differentiate during the time period, thereby producing an immortalized precursor cell population.

3. A method for producing an immortalized precursor cell population comprising: assessing Notch 1 receptor expression and/or Notch 2 receptor expression by a precursor cell; culturing a non-immortalized precursor cell in the presence of (i) a Notch 1 agonist, a Notch 2 agonist or a Notch 1 agonist and a Notch 2 agonist in an amount that maintains low Notch signal strength wherein the Notch 1 agonist, Notch 2 agonist or Notch 1 agonist and Notch 2 agonist is selected based on the assessing; and (ii) one or more growth factors, for a time period beyond which cells of the precursor cell type not in the presence of the (i) Notch 1 agonist, the Notch 2 agonist or the Notch 1 agonist and the Notch 2 agonist and (ii) the growth factors stop proliferating and differentiate or die such that the precursor cell proliferates but does not terminally differentiate during the time period, thereby producing an immortalized precursor cell population.

4. A method of embodiments disclosed herein wherein during the culturing the Notch 2 agonist is provided at a higher concentration than the Notch 1 agonist.

5. A method of embodiments disclosed herein wherein during the culturing the ratio of Notch 2 agonist to Notch 1 agonist is 150:1; 140:1; 130:1; 120:1; 110:1; 100:1;

90:1; 80:1; 70:1; 60:1; 50:1; 40:1; 30:1; 25:1; 24:1; 23:1; 22:1; 21:1; 20:1; 19:1; 18:1; 17:1 16:1; 15:1; 14:1; 13:1; 12:1; 11:1; 10:1; 9:1; 8:1; 7:1; 6:1; 5:1; 4:1; 3:1; 2:1; 1.5:1; or 1.25:1.

6. A method of embodiments disclosed herein wherein during the culturing the Notch 2 agonist is at a concentration of 0.1 µg/ml to 50 µg/ml.

7. A method of embodiments disclosed herein wherein during the culturing the Notch 1 agonist is at a concentration of 0.005 µg/ml to 30 µg/ml.

8. A method of embodiments disclosed herein wherein during the culturing the Notch 2 agonist is at a concentration of 20 µg/ml.

9. A method of embodiments disclosed herein wherein during the culturing the Notch 1 agonist is at a concentration of 2.5 µg/ml, 10 µg/ml or 0.15 µg/ml.

10. A method of embodiments disclosed herein wherein during the culturing the Notch 2 agonist is at a concentration of 10 µg/ml.

11. A method of embodiments disclosed herein wherein during the culturing the Notch 1 agonist is at a concentration of 0.02 µg/ml.

12. A method of embodiments disclosed herein wherein the one or more growth factors are IL-3; IL-6; TPO; SCF and Flt-3.

13. A method of embodiments disclosed herein wherein during the culturing IL-3 is at a concentration of 10 ng/ml.

14. A method of embodiments disclosed herein wherein during the culturing one or more of IL-6; TPO; SCF and Flt-3 are at a concentration of 50 ng/ml.

15. A method of embodiments disclosed herein wherein the precursor cell population does not substantially differentiate during the time period.

16. A method of embodiments disclosed herein wherein the precursor cell is a stem cell.

17. A method of embodiments disclosed herein wherein the precursor cell is a progenitor cell.

18. A method of embodiments disclosed herein wherein the stem cell is a hematopoietic stem cell (HSC).

19. A method of embodiments disclosed herein wherein the progenitor cell is a hematopoietic progenitor cell.

20. A method of embodiments disclosed herein wherein the hematopoietic stem or progenitor cell is obtained from bone marrow.

21. A method of embodiments disclosed herein wherein the hematopoietic stem or progenitor cell is obtained from fetal or neonatal blood.

22. A method of embodiments disclosed herein wherein the time period is 7-8 days.

23. A method of embodiments disclosed herein wherein the time period is at least five weeks.

24. A method of embodiments disclosed herein wherein the time period is at least six weeks.

25. A method of embodiments disclosed herein wherein a Notch 1, a Notch 2 agonist or a Notch 1 and Notch 2 agonist is selected based on Notch 1 receptor expression levels by the precursor cell during a subset of the time period.

26. A method of embodiments disclosed herein wherein the subset of the time period includes the first 24 hours of the culture period.

27. A method of embodiments disclosed herein wherein the subset of the time period includes the first 48 hours of the culture period.

28. A method of embodiments disclosed herein wherein the subset of the time period includes the first 72 hours of the culture period.

29. A method of embodiments disclosed herein wherein the subset of the time period includes the first third of the culture period.

30. A method of embodiments disclosed herein wherein the subset of the time period includes the first fourth of the culture period.

31. A method of embodiments disclosed herein wherein the subset of the time period includes the last 24 hours of the culture period.

32. A method of embodiments disclosed herein wherein the subset of the time period includes the last 48 hours of the culture period.

33. A method of embodiments disclosed herein wherein the subset of the time period includes the last 72 hours of the culture period.

34. A method of embodiments disclosed herein wherein the subset of the time period includes the last third of the culture period.

35. A method of embodiments disclosed herein wherein the subset of the time period includes the last fourth of the culture period.

36. A method of embodiments disclosed herein wherein the subset of the time period includes the middle 24 hours of the culture period.

37. A method of embodiments disclosed herein wherein the subset of the time period includes the middle 48 hours of the culture period.

38. A method of embodiments disclosed herein wherein the subset of the time period includes the middle 72 hours of the culture period.

39. A method of embodiments disclosed herein wherein the subset of the time period includes the middle third of the culture period.

40. A method of embodiments disclosed herein wherein the subset of the time period includes a middle fourth of the culture period.

41. A method of embodiments disclosed herein further comprising selecting a Notch 1, a Notch 2 agonist or a Notch 1 and Notch 2 agonist to continue culturing based on changed Notch 1 receptor expression levels by the precursor cell during the culture period.

42. A method of embodiments disclosed herein wherein low Notch signal strength is measured by assessing Hes1 expression.

43. A method of embodiments disclosed herein wherein low Notch signal strength is confirmed by lack of precursor cell differentiation into Thy1+ and CD25+ T cell precursors.

44. A method of embodiments disclosed herein wherein a Notch 1, a Notch 2 agonist or a Notch 1 and Notch 2 agonist is selected based on Notch 1 receptor expression levels by the precursor cell during the time period.

45. A method of embodiments disclosed herein wherein a Notch 1, a Notch 2 agonist or a Notch 1 and Notch 2 agonist is selected based on Notch 2 receptor expression levels by the precursor cell during the time period.

46. A method of embodiments disclosed herein further comprising selecting a Notch 1, a Notch 2 agonist or a Notch 1 and Notch 2 agonist to continue culturing based on changed Notch 2 receptor expression levels by the precursor cell during the culture period.

47. A method of embodiments disclosed herein wherein a Notch 1, a Notch 2 agonist or a Notch 1 and Notch 2 agonist is selected based on Notch 1 receptor expression levels and Notch 2 receptor expression levels by the precursor cell during the time period.

48. A method of embodiments disclosed herein further comprising selecting a Notch 1, a Notch 2 agonist or a Notch 1 and Notch 2 agonist to continue culturing based on changed Notch 2 receptor expression levels by the precursor cell during the culture period.

49. A method of embodiments disclosed herein further comprising selecting a Notch 1, a Notch 2 agonist or a Notch 1 and Notch 2 agonist to continue culturing based on changed Notch 1 receptor expression levels and Notch 2 receptor expression levels by the precursor cell during the culture period.

50. A method of embodiments disclosed herein wherein the assessing or further assessing measures Notch 1 receptor expression.

51. A method of embodiments disclosed herein wherein the assessing or further assessing measures Notch 2 receptor expression.

52. A method of embodiments disclosed herein wherein the assessing or further assessing measures Notch 1 receptor expression and Notch 2 receptor expression.

Alternative embodiments for implementing the methods and producing the cells and animals of the present disclosure will be apparent to one of skill in the art and are intended to be comprehended within the accompanying claims. The following experimental examples are offered by way of illustration and not by way of limitation.

7. EXAMPLES

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

The described examples show that maintenance of low Notch signal strength (which can be mediated by Notch 1 and/or Notch 2) leads to improved expansion and engraftment of stem cells. The results suggest that careful titration of the Notch signal in stem cells by selective paralog activation can be beneficial. The current disclosure shows that culture of murine bone marrow highly enriched stem (SK-SLAM) cells in wells with low amounts of Notch 1 agonist in combination with relatively higher amounts of Notch 2 agonist leads to 2-fold increased generation of SK-SLAM cells (Sca-1$^+$c-kit$^+$CD150$^+$CD48$^-$CD11b$^-$) following 7-8 days of culture, compared to a less than 1-fold increase in cultures with Delta1$^{ext\text{-}IgG}$, Notch 2 agonist alone, or control ligands when monoclonal antibodies specific for either Notch 1 or Notch 2 receptors are immobilized to the plastic surface. Thus, Notch paralog specific activation by use of a Notch 1 agonist, a Notch 2 agonist or a Notch 1 agonist and a Notch 2 agonist that provides low Notch signal strength provides a novel way to expand stem cells, including hematopoietic stem cells.

The present disclosure also provides that quantitative differences in Notch signaling account for retardation of myeloid differentiation. Because quantitative rather than qualitative differences in Notch signaling are indicated, activation of either Notch 1 and/or Notch 2 can be used to generate desired levels of Notch signaling. Further, because Notch 1 and Notch 2 receptor expression occurs independently of each other during culture, different Notch agonists can be chosen based on changing expression levels over time. In these embodiments, Notch signaling can be due to the presence of a Notch 1 agonist; a Notch 2 agonist; or a Notch 1 agonist and a Notch 2 agonist.

7.1 Example 1

FIG. 1. Culture with specific Notch antibodies leads to increased generation of SK-SLAM cells. Each bar represents the mean fold increased number of SK-SLAM cells in cultures with Delta1$^{ext\text{-}IgG}$ at 5 µg/ml, HuIgG at 5 µg/ml and indicated doses of immobilized monoclonal antibodies for Notch 1 [HMN1-12 (MN1)] or Notch 2 antibodies [HMN2-35 (MN2)] (Biolegend). Bars are the mean fold increase compared to the initial number of SK-SLAM placed in the culture well of 2 separate experiments+/−range.

FIG. 2. Cord blood CD34+ cells from two separate units were cultured for 14 days in Stemspan with IL-3 (10 ng/ml), IL-6, TPO, SCF and Flt-3 ligand (all 50 ng/ml). Cells were grown in the presence of immobilized retronectin 5 µg/ml and Delta1 (2.5 µg/ml), anti-human Notch 2 (clone MHN2-25, 0.5 µg/ml), anti-human Notch 2 0.5 µg/ml combined with anti-human Notch 1 (clone MHN1-519), or control IgG. Notch antibodies maintained a higher proportion of CD34+ progenitor cells and the more primitive CD34+ 90 low cells than either Delta or the control IgG. Additionally, Notch 2 antibody alone and combined with Notch 1 antibody gave a greater expansion of CD34+ CD90 low cells.

FIG. 3. After culture as above for 14 days, the expanded progeny of 10,000 cord blood CD34+ cells were transplanted into each of six NSG mice per group. Bone marrow aspirates from mice were analyzed for engraftment by flow cytometry two weeks post-transplant. The combination of Notch 1 and Notch 2 antibodies enabled significantly higher levels of human engraftment than Delta, IgG, or Notch 2 antibody alone (p=0.0024 and p=0.0225 respectively, for the two cord blood units).

In another application, these methods were applied to embryonic hematopoietic stem cells derived in vivo. The first HSC arise during development in the AGM (Aorta-Gonad-Mesonephros) region and co-express endothelial (VE-Cadherin) and hematopoietic (CD45) markers. Conditions using a combination of immobilized ligand Delta1 (2.5 µg/ml), retronectin 5 µg/ml, rmSCF, rhIL6, rhFLT3L (all at 100 ng/ml), rhTPO (20 ng/ml), and small molecule TGF-3 inhibition (10 µM) that are capable of expanding short-term and long-term repopulating HSC/progenitors from murine AGM-derived CD45+/VE-Cadherin+ cells in culture have been determined. That monoclonal antibodies specific for either Notch 1 or Notch 2 receptors immobilized to the plastic surface can substitute for Delta1 in this culture system, generating cells capable of myeloid and lymphoid engraftment in transplantation assays is now shown. Furthermore, in preliminary experiments, Notch 2-specific paralog activation with immobilized MN2 antibody generates greater number of LSK-SLAM (Sca1+c-kit+CD150+CD48−F480−Gr1−) cells (A) following 5 day culture period and results in enhanced 2 week and 6 week peripheral blood engraftment compared with immobilized Notch ligand Delta1$^{ext\text{-}IgG}$ (B). Thus, Notch paralog-specific activation can further enhance the ability to expand multilineage HSC from embryonic sources which could have applications in expanding HSC from novel sources such as embryonic stem cells and induced pluripotent stem cells.

FIG. 4. Culture of AGM-derived CD45+/VE-Cadherin+ cells on specific Notch antibodies effects generation of LSK-SLAM cells and multilineage engraftment. A. Numbers of LSK-SLAM(Sca1+c-kit+CD150+CD48−Gr1−F480−) cells by flow cytometry analysis generated following 5 days of cultures on Delta1$^{ext\text{-}IgG}$ at 2.5 µg/ml, HuIgG at 2.5 µg/ml and indicated doses of immobilized monoclonal antibodies for Notch 1 [HMN1-12 (MN1)] or Notch 2 antibodies [HMN2-35 (MN2)] (Biolegend). Cell numbers are expressed per one AGM equivalent of input starting CD45+/VE-Cadherin+ cells and error bars represent standard deviation of triplicate wells analyzed. B-D. Week 2 and 6 peripheral blood engraftment of cells cultured in panel A, transplanted at 0.5 AGM equivalent of starting cells (CD45.2) per mouse with 3×10$^4$ rescue CD45.1 bone marrow cells. Shown is % donor engraftment (CD45.2), donor myeloid engraftment (Gr1 and/or F480), and donor B lymphoid (CD19)/T lymphoid (CD3) engraftment as percentage of total CD45+ cells in peripheral blood for each mouse analyzed.

FIG. 5 and FIG. 6 provide additional data.

FIGS. 3 & 7. FIG. 7 Cord blood CD34+ cells from two separate units (Exp. 409) or a pool of two units (Exp. 414) were cultured for 14 days in Stemspan with IL-3 (10 ng/ml), IL-6, TPO, SCF and Flt-3 ligand (all 50 ng/ml). Cells were grown in the presence of immobilized retronectin 5 μg/ml and Delta1 (2.5 μg/ml), anti-human Notch 2 (clone MHN2-25, 0.5 μg/ml, Exp. 409), anti-human Notch 1 (clone MHN1-519, 0.02 μg/ml, Exp. 414) anti-human Notch 2 0.5 μg/ml combined with anti-human Notch 1 0.02 μg/ml, or control IgG.

Expanded progeny of 10,000 cells were transplanted into each of five (Exp. 414) or six (Exp. 409) NSG mice per group. Bone marrow aspirates were analyzed by flow cytometry for total human (CD45), lymphoid (CD19) and myeloid two weeks post transplant (both experiments) and 8 weeks post transplant (Exp. 414). Bone marrow was harvested and analyzed ten weeks after transplant for Exp. 409.

FIGS. 8A & 8B and 9A, 9B & 9C provide additional data.

7.2 Example 2

Qualitative Differences in the Intracellular Domain (ICD) of Individual Notch Paralogs do not Impact Lineage Determination.

As a step toward further advancing the model that lineage determination is affected by quantitative differences in Notch signal strength, qualitative differences in the signaling capacity of Notch 1 or Notch 2 were assessed to determine if they impacted cell fate determination. To assess these differences, mice were used in which the genomic coding region for the entire Notch 2-ICD was swapped into the Notch 1 locus (N1$^{12/12}$) and the Notch 1-ICD was swapped into the Notch 2 locus (N2$^{21/21}$) (Liu Z, Chen S, Boyle S, Zhu Y, Zhang A, Piwnica-Worms D R, et al. Dev Cell. 2013; 25(6):585-98). In studies of kidney development, where Notch 2, but not Notch 1, plays indispensable roles in organogenesis, development was found to be normal in N2$^{21}$/2$^1$ mice, indicating that the swapped Notch 1-ICD was functional and performed comparably to the Notch 2-ICD. With respect to hematopoiesis, the results showed that N1$^{12/12}$ and N2$^{21}$/2$^1$ mice were both able to generate T, B, and myeloid cell numbers similar to littermate controls both in vivo and in vitro (FIG. 10). This result confirms our quantitative model of Notch signaling in lineage determination.

7.3 Example 3

Notch Activation Mediated by Immobilized Paralog-Specific Antibodies Generates a Significant Increase in Rapid Repopulating Cells Compared to Immobilized Delta1 Ligand.

Dynamic changes in Notch paralog expression accompany murine hematopoiesis. Notch 2 is the predominant Notch receptor on the surface of freshly isolated LSK-SLAM (Lineage-Sca1+Kit+CD150+CD48−) and LSK cells, while Notch 1 becomes predominant following culture with high densities of Delta1, conditions that promote differentiation toward T cells at the expense of the HSPC pool (data not shown). As a result of this shift in cell-surface expression, it was investigated whether the selective activation of individual receptors using paralog-specific antibodies would limit Notch activation and enhance ex vivo generation of repopulating cells compared to immobilized Delta1. Murine bone marrow LSK-SLAM cells were cultured with immobilized Delta1 or immobilized activating antibody against the Notch 2 extracellular domain and used in a limit dilution transplantation assay. It was found that, compared to Delta1, antibody-selective Notch 2 activation generated a 3.6 fold higher frequency of repopulating cells 6 weeks post-transplant (L-calc p=0.02 for lineage repopulation at the highest cell dose tested, (data not shown)). These studies showed that a Notch paralog-specific antibody enhanced the ex vivo generation of repopulating cells to a greater degree than a Notch ligand.

In contrast to murine LSK-SLAM cells, freshly isolated cord blood (CB) CD34$^+$ cells express both Notch 1 and Notch 2 (FIG. 11). CB CD34$^+$ cells cultured for 2 weeks with immobilized antibodies specific to the extracellular domain of human Notch 1 or Notch 2 (MHN1-519 and MHN2-25, see www.Biolegend.com; Haraguchi K, Suzuki T, Koyama N, Kumano K, Nakahara F, Matsumoto A, et al. J Immunol. 2009; 182(10):6168-78) reproducibly generated substantially more CD34$^+$ and CD34$^+$CD90$^{lo}$ cells, a less mature CD34$^+$ cell subset in which repopulating cells reside than a previously published optimal dose of immobilized Delta1 (Delaney C, Varnum-Finney B, Aoyama K, Brashem-Stein C, Bernstein I D. Blood. 2005; 106(8):2693-9; Delaney C, Heimfeld S, Brashem-Stein C, Voorhies H, Manger R L, Bernstein I D. Nat Med. 2010; 16(2):232-6; CD900 cells were those cells expressing low amounts of CD90, as determined by a gated cut-off amount defined previously in Majeti R, Park C Y, Weissman I L. Cell Stem Cell 2007; 1: 635-645) (data not shown). Most importantly, compared to immobilized Delta1, CD34$^+$ cells cultured with concentrations of immobilized anti-Notch 1 or anti-Notch 2 antibodies (MHN1-519 and MHN2-25, respectively) maximizing CD34$^+$CD90$^{lo}$ cell generation induced significantly greater rapid repopulating (2-3 weeks) activity in NOD-scid IL2Rgamma null (NSG) mice (FIG. 12; p-value MHN1-519=0.0286, p-value MHN2-25=0.0460). Overall, these data point to the use of paralog-specific Notch activation to increase ex vivo derived HSPC, enhancing the generation of rapidly repopulating cells for therapeutic application.

7.4 Example 4

Paralog Specific Notch Antibodies Activate Notch Receptors Insusceptible to Ligand-Induced Activation.

As a first step toward addressing why individual receptor antibodies are more effective than ligand in inducing expansion of engraftable HSPC, it was tested whether CB CD34+ cells display a difference in the ability to immediately induce expression of the target gene Hes1 following 4 hr Notch activation by immobilized Delta1, anti-Notch 1 or anti-Notch 2 antibodies. The anti-Notch 1 antibody (MHN1-519) or anti-Notch 2 antibody (MHN2-25) (both commercially available from Biolegend, San Diego, Calif.) raised against their respective amino terminal fragments, including the EGF domains involved in ligand were compared, as well as anti-Notch 1 and anti-Notch 2 antibodies raised against their cognate juxtamembrane Negative Regulatory Region (NRR) (such antibodies being hereafter referred to as NRR-N1 and NRR-N2, respectively), which are known to inhibit Notch activation when soluble and activate when immobilized (personal communication C. Siebel, Genentech; Wu Y, Cain-Hom C, Choy L, Hagenbeek T J, de Leon G P, Chen Y, et al. Nature. 2010; 464(7291):1052-7) (FIG. 13) As shown in FIG. 14, induction with MHN1-519 led to 2-3 fold greater Hes1 expression than Delta1. In contrast, MHN2-25 resulted in approximately two-fold greater Hes1 expression than Delta1 at the lower dose tested, but was equivalent to Delta1 at the higher dose. In comparison, NRR-N1 and NRR-N2 were less effective than either respective EGF antibody at inducing Hes1 expression.

Further studies addressed whether the observed differences in agonist activation potency reflect the differential ability of Delta1 and either MHN1-519 or MHN2-25 to interact with Notch on the more primitive $CD34^+CD90^{lo}$ HSPC subset. Freshly isolated CB $CD34^+CD90^{lo}$ and $CD34^+CD90^-$ cells were incubated with either Delta1, MHN1-519 or control IgG for 4 hrs and Hes1 expression was determined by qPCR. Compared to $CD34^+CD90^-$ cells, a trend toward greater Notch activation following exposure of the $CD34^+CD90^{lo}$ population to MHN1-519 was observed, compared to exposure to Delta1 (FIG. 15A). These data correlate with results of ligand binding assays in $CD34^+CD90^{lo}$ cells, where MHN1-519 and MHN2-25 were able to bind to their respective paralog, while Delta1 showed little or no binding (data not shown). Following differentiation of these cells by culture with cytokines, equivalent levels of Notch activation were found with either immobilized Delta1 or MHN1-519, as measured by Hes1 expression (FIG. 15B). Taken together, these studies suggest that MHN1-519 and MHN2-25 are more effective in generating $CD34^+CD90^{lo}$ cells due to their ability to bind to receptors initially insusceptible to Delta1 binding and activation.

One mechanism capable of suppressing trans-expressed ligand activation of Notch receptors is cis-inhibition mediated by endogenously expressed ligand. Recent studies have shown that cis-expressed ligand can interact with the same Notch receptor interface as ligand bound in trans (Luca V C, Jude K M, Pierce N W, Nachury M V, Fischer S, Garcia K C. Science. 2015; 347(6224):847-53). It was hypothesized that Notch antibody agonists are able to induce activation of their cognate receptor in the context of cis-expressed ligand because the antibody-receptor interface is distinct from the ligand-receptor interface. To test this hypothesis cross-blocking assays in Jurkat cells were utilized. It was found that the addition of Delta1 blocked binding of myc-tagged Delta1, but not binding of MHN1-519 (FIG. 16). These studies suggest that MHN1-519 binds an epitope on Notch 1 distinct from the site of Delta1 binding. It was further found that a polypeptide encompassing Notch 1 EGF-like repeats 7-14, including EGF-like repeats 11 and 12 involved in ligand binding, inhibited the binding of Delta1 to Notch 1 but did not alter interactions of MHN1-519 with Notch 1 (data not shown), providing further evidence that agonist antibody and ligand interaction interfaces are unique. Furthermore, as the immunogen used to generate the MHN1-519 antibody encompassed Notch 1 EGF-like repeats 1-13, simple subtraction suggests that the antibody epitope likely resides in the Notch 1 membrane-distal EGF-like repeats 1-6, which are N-terminal to the ligand binding site.

To determine whether antibody is able to activate otherwise cis-inhibited ligand, a previously developed Notch reporter system in CHO-K1 cells expressing a Notch1 variant was used, in which the ICD of Notch1 is replaced with yeast Gal4 along with a UAS-driven YFP reporter. Using this system, it was shown that Notch receptor stimulation by exogenous Delta1 leads to the accumulation of YFP (Sprinzak D, Lakhanpal A, Lebon L, Santat L A, Fontes M E, Anderson G A, et al. Nature. 2010; 465(7294):86-90). However, the co-expression of a stably integrated tetracycline inducible Delta1 gene leads to cis-inhibition, preventing the activation of Notch by trans-ligand, reducing YFP accumulation. These cells thus provide a validated model for analysis of cis inhibition and Notch activation. Using this system, it was observed that both MHN1-519 and Delta1 are capable of inducing YFP in a dose dependent manner when presented exogenously in the absence of cis-ligand (FIG. 17). As shown previously upon induction of cis-expressed ligand, trans-Delta is unable to activate Notch. However, when presented with MHN1-519, the Notch 1 is able to signal, regardless of cis-ligand state. Taken together, these data suggest that MHN1-519, through a Notch 1 interface distinct from that of Delta1, is capable of activating Notch receptors normally insusceptible due to ligand cis-inhibition.

To assess the possibility that cis-inhibition by endogenous ligand expression accounted for the superiority of antibody in our human CB studies, it was determined whether CB $CD34^+CD90^{lo}$ cells express canonical (DLL1, DLL3, DLL4, JAG1 and JAG2) or non-canonical (DLK1 and DLK2) ligands using quantitative RT-PCR and FACS analyses. PCR assessment revealed expression of Jag2, Dll1, Dll4 and Dlk1 (data not shown). Using FACS analysis, the cell-surface expression of Jag2 was confirmed on the primitive $CD34^+CD90^{lo}$ subset known to contain repopulating cells, but not on the $CD34^+CD90^-$ subset (data not shown).

Using MHN1-519 and MHN2-25, the cell surface expression of Notch 1 and Notch 2 was assessed for CB derived $CD34^+$ cells before and during a two-week expansion on immobilized Delta1 (FIG. 18). While freshly sorted CB $CD34^+$ cells express relatively the same amounts of Notch 1 and Notch 2, time in culture shows dynamic changes in cell surface expression, with Notch 1 continually increasing and Notch 2 decreasing and then remaining constant

7.5 Example 5

Paralog Specific Notch 1 Antibody Produces Higher Number of Lymphoid Progenitor Cells than Delta.

Cord blood $CD34^+$ cells from two separate units were cultured for 7 days in Stemspan with IL-3 (10 ng/ml), IL-6, TPO, SCF and Flt-3 ligand (all 50 ng/ml). Cells were grown in the presence of immobilized retronectin 5 μg/ml and (i) immobilized control IgG (ii) immobilized Delta1, 0.5, 2.5 or 10 μg/ml), or (iii) immobilized anti-human Notch 1 antibody ((0.02, 0.1, 0.5 or 2.5 μg/ml, clone MHN1-519 (commercially available from Biolegend, San Diego, Calif.)). Common Lymphoid Progenitor cells (CLP), the $CD34^+/CD38^-/CD7^+$ population, were assessed by flow cytometry. The results are shown in FIG. 19. Growth of cells with anti-Notch 1 antibody produced a higher number of CLP than Delta 1.

7.6 Example 6

Cord Blood $CD34^+$ Cells Cultured with Immobilized Notch 1 Antibody Result in T Cell Engraftment when Transplanted into NSG Mice.

Cord blood $CD34^+$ cells from a pool of two units were cultured for 14 days in Stemspan with IL-3 (10 ng/ml), IL-6, TPO, SCF and Flt-3 ligand (all 50 ng/ml). Cells were grown in the presence of immobilized retronectin 5 μg/ml and (i) Delta1 2.5 μg/ml, (ii) Control IgG, (iii) anti-human Notch 1 antibody 0.02 μg/ml (clone MHN1-519 (commercially available from Biolegend, San Diego, Calif.)), or (iv) anti-human Notch 1 0.02 μg/ml combined with anti-human Notch 2 0.5 μg/ml (clone MHN2-25, (commercially available from Biolegend, San Diego, Calif.)).

On day 14 of culture, the expanded progeny of 10,000 cells was transplanted into each of five NSG mice per group. After 18 weeks, bone marrows were harvested and total human engraftment (CD45 percent, FIG. 20A) and human T cell engraftment (CD3 percent, FIG. 20B) were assessed by flow cytometry. Cells cultured with anti-Notch 1 antibody grew T cells in 4 of 5 mice. Human T cells (CD3$^+$) formed only in mice receiving cells cultured with anti-Notch 1 antibody (FIG. 20B), suggesting that a higher Notch signal was induced in a portion of cells sufficient to induce differentiation towards the T cell lineage and give rise to cells that migrate to and engraft in the thymus where they mature into CD3$^+$ T cells.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in expansion or engraftment of HSPC.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; +19% of the stated value; ±18% of the stated value; +17% of the stated value; +16% of the stated value; +15% of the stated value; ±14% of the stated value; +13% of the stated value; +12% of the stated value; ±11% of the stated value; +10% of the stated value; +9% of the stated value; +8% of the stated value; +7% of the stated value; +6% of the stated value; +5% of the stated value; +4% of the stated value; ±3% of the stated value; ±2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

Various references such as patents, patent applications, and publications are cited herein, the disclosures of which are hereby incorporated by reference herein in their entireties.

What is claimed is:

1. A method for expanding hematopoietic stem/progenitor cells, comprising culturing the hematopoietic stem/progenitor cells in the presence of
   (a) a Notch 1 paralog-specific agonist which is an antibody or an antigen-binding fragment thereof that specifically binds to an extracellular EGF repeat domain of Notch 1,
   (b) a Notch 2 paralog-specific agonist which is an antibody or an antigen-binding fragment thereof that specifically binds to an extracellular EGF repeat domain of Notch 2, and
   (c) growth factors,
thereby producing an expanded hematopoietic stem/progenitor cell population.

2. The method of claim 1, further comprising detecting Notch 1expression by the hematopoietic stem/progenitor cells before and/or during the culturing; and calibrating an amount of the Notch 1 paralog-specific agonist in the culture based on the detecting.

3. The method of claim 1, wherein the hematopoietic stem/progenitor cells are obtained from umbilical cord blood.

4. The method of claim 1, wherein during the culturing the Notch 2 paralog-specific agonist is at a concentration of 0.1 μg/ml to 50 μg/ml.

5. The method of claim 1, wherein during the culturing the Notch 1 paralog-specific agonist is at a concentration of 0.005 μg/ml to 30 μg/ml.

6. The method of claim 1, wherein the growth factors are interleukin-3 (IL-3), interleukin-6 (IL-6), thrombopoietin (TPO), stem cell factor (SCF), and Flt-3 ligand.

7. The method of claim 1, wherein a period of culturing is from seven days to six weeks.

8. The method of claim 1, wherein the Notch 1 paralog-specific agonist and/or the Notch 2 paralog-specific agonist is immobilized on a first solid phase.

9. The method of claim 8, wherein the Notch 1 paralog-specific agonist is immobilized on a first solid phase and the Notch 2 paralog-specific agonist is immobilized on a second solid phase.

10. The method of claim 8, wherein the first solid phase is the surface of a tissue culture dish or flask or a bead.

11. The method of claim 9, wherein (i) the first solid phase is the surface of a tissue culture dish or flask, and the second solid phase is a bead, or (ii) the first solid phase is a bead and the second solid phase is a tissue culture dish or flask.

12. The method of claim 1, wherein the hematopoietic stem/progenitor cells are (i) hematopoietic stem cells, (ii) hematopoietic progenitor cells, or (iii) hematopoietic stem and progenitor cells.

13. The method of claim 1, wherein the method further produces early T cell stem/progenitor able to migrate to the thymus and generate mature T cells.

14. A method for expanding hematopoietic stem/progenitor cells, comprising culturing the hematopoietic stem/progenitor cells in the presence of
   (a) a Notch 1 paralog-specific agonist which is an antibody or an antigen-binding fragment thereof that specifically binds to an extracellular EGF repeat domain of Notch 1 and activates Notch 1,
   (b) a Notch 2 paralog-specific agonist which is an antibody or an antigen-binding fragment thereof that specifically binds to an extracellular EGF repeat domain of Notch 2 and activates Notch 2, and
   (c) growth factors,
   wherein the Notch 1 activation and the Notch 2 activation overcome cis-inhibition caused by endogenous expression of a Notch ligand,
   thereby producing an expanded hematopoietic stem/progenitor cell population.

15. The method of claim 1, further comprising detecting Notch 2 expression by the hematopoietic stem/progenitor cells before and/or during the culturing; and
   calibrating an amount of the Notch 2 paralog-specific agonist in the culture based on the detecting.

16. The method of claim 1, further comprising detecting Notch 1 expression and Notch 2 expression by the hematopoietic stem/progenitor cells before and/or during the culturing; and
   calibrating an amount of the Notch 1 paralog-specific agonist and an amount of the Notch 2 paralog-specific agonist in the culture based on the detecting.

17. The method of claim 1, wherein the antigen-binding fragment thereof of the Notch 1 paralog-specific agonist and of the Notch 2 paralog-specific agonist are selected from an Fv, Fab, Fab', F(ab')$_2$, or single chain Fv fragment (scFv).

18. The method of claim 14, wherein the antigen-binding fragment thereof of the Notch 1 paralog-specific agonist and of the Notch 2 paralog-specific agonist are selected from an Fv, Fab, Fab', F(ab')$_2$, or single chain Fv fragment (scFv).

* * * * *